(12) United States Patent
Takemura et al.

(10) Patent No.: US 10,197,914 B2
(45) Date of Patent: Feb. 5, 2019

(54) POSITIVE PHOTOSENSITIVE RESIN COMPOSITION, PHOTO-CURABLE DRY FILM AND METHOD FOR PRODUCING THE SAME, PATTERNING PROCESS, AND LAMINATE

(71) Applicant: SHIN-ETSU CHEMICAL CO., LTD., Tokyo (JP)

(72) Inventors: Katsuya Takemura, Jyoetsu (JP); Masashi Iio, Jyoetsu (JP); Hiroyuki Urano, Jyoetsu (JP); Takashi Miyazaki, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/432,127

(22) Filed: Feb. 14, 2017

(65) Prior Publication Data

US 2017/0255097 A1    Sep. 7, 2017

(30) Foreign Application Priority Data

Mar. 4, 2016    (JP) ................ 2016-042250

(51) Int. Cl.

| | | |
|---|---|---|
| *G03F 7/075* | (2006.01) | |
| *G03F 7/039* | (2006.01) | |
| *H01L 21/027* | (2006.01) | |
| *C08L 83/14* | (2006.01) | |
| *C08G 77/12* | (2006.01) | |
| *C07C 39/21* | (2006.01) | |
| *C08G 77/52* | (2006.01) | |
| *G03F 7/20* | (2006.01) | |

(Continued)

(52) U.S. Cl.
CPC .............. *G03F 7/039* (2013.01); *C07C 39/21* (2013.01); *C08G 77/04* (2013.01); *C08G 77/06* (2013.01);
(Continued)

(58) Field of Classification Search
CPC ...... G03F 7/0757; G03F 7/168; G03F 7/2002; G03F 7/2037; G03F 7/32; G03F 7/38;
(Continued)

(56) References Cited

U.S. PATENT DOCUMENTS 3,159,601 A    12/1964 Ashby
3,159,662 A    12/1964 Ashby
(Continued)

FOREIGN PATENT DOCUMENTS

EP    1 953 183 A2    8/2008
EP    2 602 661 A1    6/2013
(Continued)

OTHER PUBLICATIONS

Aug. 4, 2017 Extended Search Report issued in European Patent Application No. 17 00 0284.

*Primary Examiner* — Amanda C. Walke
(74) *Attorney, Agent, or Firm* — Oliff PLC

(57) ABSTRACT

The present invention provides a positive photosensitive resin composition containing (A) a polymer compound containing a siloxane chain, the polymer compound having a repeating unit shown by the general formula (1) and a weight average molecular weight of 3,000 to 500,000, (B) a photosensitive material capable of generating an acid by light and increasing a dissolution rate in an aqueous alkaline solution, (C) a crosslinking agent, and (D) a solvent. There can be provided a positive photosensitive resin composition that can remedy the problem of delamination caused on a metal wiring such as Cu and Al, an electrode, and a substrate, especially on a substrate such as SiN, and can form a fine pattern having a forward tapered shape without (Continued)

generating a scum and a footing profile in the pattern bottom and on the substrate when a widely used 2.38% TMAH aqueous solution is used as the developer.

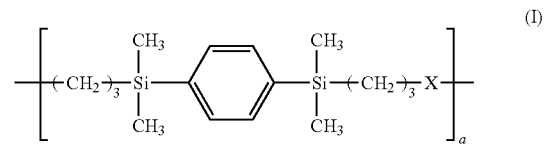

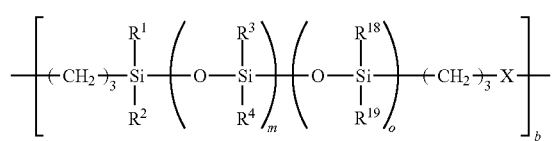

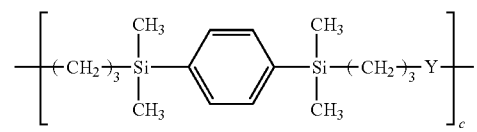

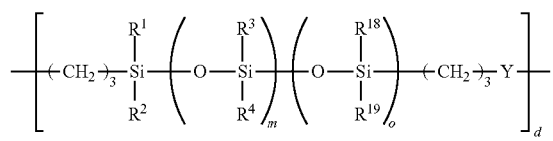

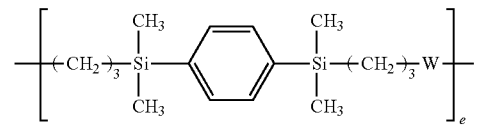

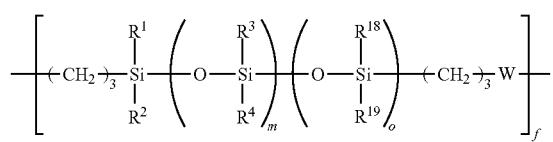

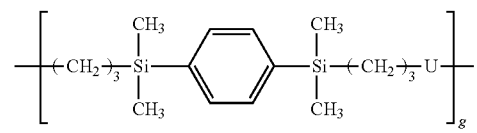

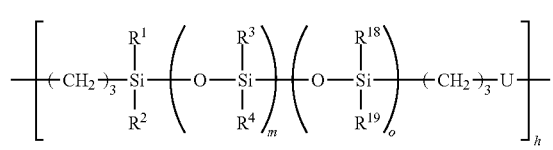

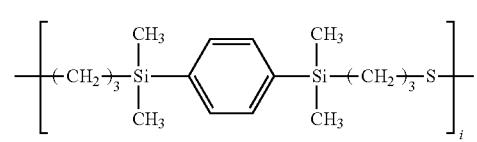

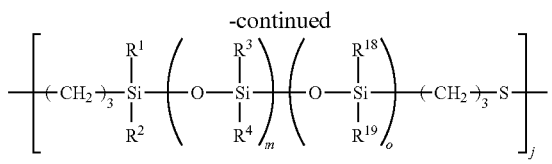

20 Claims, 1 Drawing Sheet

(51) Int. Cl.
  *C09D 183/14*    (2006.01)
  *H01L 21/311*    (2006.01)
  *C08G 77/04*    (2006.01)
  *C08G 77/06*    (2006.01)
  *G03F 7/004*    (2006.01)
  *G03F 7/11*    (2006.01)
  *G03F 7/16*    (2006.01)
  *G03F 7/32*    (2006.01)
  *G03F 7/38*    (2006.01)
  *G03F 7/40*    (2006.01)
(52) U.S. Cl.
  CPC ............ *C08G 77/12* (2013.01); *C08G 77/52* (2013.01); *C08L 83/14* (2013.01); *C09D 183/14* (2013.01); *G03F 7/0045* (2013.01); *G03F 7/0757* (2013.01); *G03F 7/11* (2013.01); *G03F 7/162* (2013.01); *G03F 7/168* (2013.01); *G03F 7/2002* (2013.01); *G03F 7/2037* (2013.01); *G03F 7/322* (2013.01); *G03F 7/38* (2013.01); *G03F 7/40* (2013.01); *H01L 21/0271* (2013.01); *H01L 21/311* (2013.01)
(58) Field of Classification Search
  CPC .......... G03F 7/40; G03F 7/038; G03F 7/0382; G03F 7/09; G03F 7/11; C08G 77/52; C08G 77/12; C09D 183/14; C08L 83/14; H01L 21/311; C07C 39/21
  USPC .............................................. 430/285.1, 271.1
  See application file for complete search history.

(56) References Cited

U.S. PATENT DOCUMENTS

| | | | |
|---|---|---|---|
| 3,220,972 A | 11/1965 | Lamoreaux | |
| 3,775,452 A | 11/1973 | Karstedt | |
| 7,785,766 B2* | 8/2010 | Kato | C08G 77/52 430/270.1 |
| 8,796,410 B2* | 8/2014 | Sugo | C08G 73/0638 528/35 |
| 9,377,689 B2* | 6/2016 | Takemura | C07C 39/21 |
| 2003/0211407 A1 | 11/2003 | Watanabe et al. | |
| 2008/0182087 A1 | 7/2008 | Kato et al. | |
| 2009/0215222 A1 | 8/2009 | Arai et al. | |
| 2015/0056545 A1* | 2/2015 | Urano | G03F 7/038 430/18 |
| 2016/0097973 A1* | 4/2016 | Urano | C09D 183/14 428/138 |

FOREIGN PATENT DOCUMENTS

| | | |
|---|---|---|
| EP | 2 980 172 A1 | 2/2016 |
| EP | 3 002 308 A1 | 4/2016 |
| JP | 2008-184571 A | 8/2008 |
| JP | 2009-200315 A | 9/2009 |

\* cited by examiner

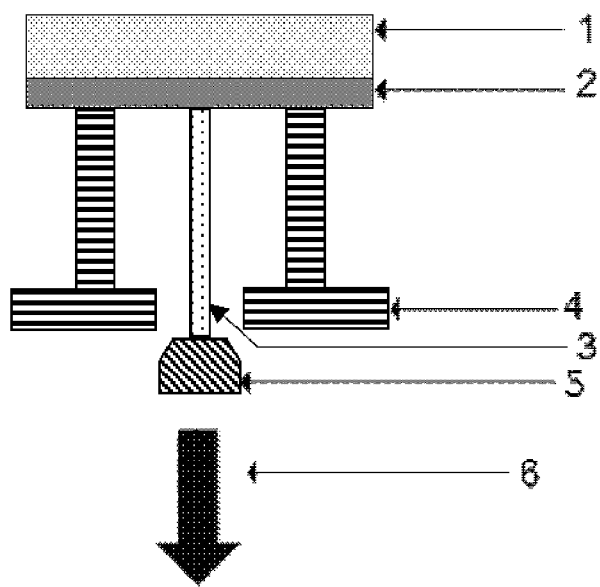

POSITIVE PHOTOSENSITIVE RESIN COMPOSITION, PHOTO-CURABLE DRY FILM AND METHOD FOR PRODUCING THE SAME, PATTERNING PROCESS, AND LAMINATE

BACKGROUND OF THE INVENTION

Field of the Invention

The present invention relates to a positive photosensitive resin composition using a silicone-skeleton-containing polymer compound, a photo-curable dry film formed by the positive photosensitive resin composition and a method for producing the same, patterning processes using the positive photosensitive resin composition or the photo-curable dry film, and a laminate obtained by laminating the photo-curable dry film on a substrate.

Description of the Related Art

As various electronic devices including a personal computer, a digital camera, and a mobile phone progress toward downsizing and higher performance, requirements are rapidly increasing for further downsizing, thinning, and densifying in semiconductor devices. Accordingly, it is desired to develop a photosensitive insulating material that can accommodate not only an increase in surface area of a substrate for the sake of higher productivity, but also a structure having fine concavity and convexity with high aspect ratio on a substrate, in high density mounting technologies including a chip size package or a chip scale package (CSP) and a three-dimensional lamination.

As the photosensitive insulating material, there has been proposed a photo-curable resin composition that can be applied with a wide range of film thickness by a spin coating method, which is commonly used in the semiconductor device fabrication, can be processed into a fine pattern with a wide range of wavelength, and can be post-cured at low temperature to form a top coat having excellent flexibility, heat resistance, electric characteristics, adhesiveness, reliability, and chemical resistance to protect electric and electronic parts (Patent Document 1). The spin coating method has an advantage of easily forming a film on a substrate.

The photo-curable resin composition for providing a top coat to protect electric and electronic parts is used with a film thickness of 1 to 100 μm on a substrate. Unfortunately, the photo-curable resin composition has a practical limit of forming a film on a substrate by the spin coating method due to an increase in viscosity when the film thickness exceeds 30 μm.

Additionally, when the photo-curable resin composition is applied onto a substrate having an uneven surface by the spin coating method, the composition is difficult to coat the substrate uniformly. This easily causes voids in the photo-curable resin layer on an uneven portion of the substrate. It would therefore be desirable to improve planarity and step coverage. As an alternative coating method of the spin coating method, a spray coating method has been proposed (Patent Document 2). However, in principle, this method easily causes defects such as height difference due to unevenness of a substrate, film loss at pattern edge, and a pinhole in a recess bottom. Thus, the problems of planarity and step coverage still remain unsolved.

The recent high density mounting technology including a chip size package or a chip scale package (CSP) and a three-dimensional lamination has greatly expanded its emphasis in a technology that allows one to form a fine pattern having a high aspect ratio on a substrate and cover the pattern with metal such as copper for rewiring from a chip. As the chip advances toward higher density and higher integration, it is strongly desired in the rewiring technology to reduce the line width of the pattern and the size of a contact hole for connection between substrates. To obtain a fine pattern, lithography is commonly used. Above all, a negative photosensitive resin composition is suitable to obtain a fine pattern. The pattern used for rewiring is curable and permanently exists between chips or device chips, and is required to function as a top coat excellent in flexibility, heat resistance, electric characteristics, adhesiveness, reliability, and chemical resistance to protect electric and electronic parts. Thus, the resist composition for providing the pattern is preferably of a negative type.

However, if the negative photosensitive resin composition is used to form a contact hole for connecting substrates, wirings, or circuits in the three-dimensional lamination as a through electrode, the contact hole tends to be formed in a reversed tapered shape such that the upper aperture diameter is smaller than the lower aperture diameter, or to be formed in an overhang shape such that the upper aperture is extremely small. The reversed tapered shape and the overhang shape make it difficult to form a metal film by sputtering and to fill the hole with metal by plating for conductive connection between wirings. The preferable shape of the contact hole for the through electrode is a forward tapered shape such that the upper aperture is larger than the lower aperture.

Moreover, it is concerned that the negative photosensitive resin composition reaches a limit of resolution in accordance with the pattern miniaturization expected to further progress in future. That is, the negative photosensitive resin composition may cause pattern deterioration such as undissolved residues and a scum in the pattern bottom and a footing profile in the pattern on the substrate, e.g. when a coating film formed of the photosensitive resin composition on the substrate is thick. These scum and footing profile are likely to cause disconnection or interruption of an electric circuit and wiring during the rewiring process, so that it is necessary to inhibit generation of such problems. However, it cannot be denied that these scum and footing profile are difficult to be resolved since the miniaturization further progresses in the negative photosensitive resin composition.

On the other hand, the negative photosensitive resin composition capable of forming a fine pattern to be used for the rewiring process and useful for a top coat to protect electric and electronic parts occasionally covers a Cu wiring that has been previously processed on a substrate or an Al electrode on a substrate. In addition, the substrate provided with a wiring and an electrode includes an insulator substrate such as SiN, which needs to be widely covered. However, adhesion between such a substrate and a coating layer formed of the negative photosensitive resin composition is still insufficient, so that there often occurs a problem in which the coating layer of the negative photosensitive resin composition is delaminated from the substrate.

In addition, an organic solvent is commonly used as a developer in patterning with the negative photosensitive resin composition useful for a top coat to protect electric and electronic parts. In this case, an exposed part becomes insoluble in the organic solvent developer by a crosslinking reaction or the like, while an unexposed part is readily soluble in the organic solvent developer, providing a pattern.

However, there is an idea that the organic solvent development is not desirable in view of the disposal of waste liquid after development, load to an environment, and so forth. Moreover, the organic solvent developer is expensive. Thus, development with an aqueous alkaline solution such as a 2.38% tetramethylammonium hydroxide (TMAH) aqueous solution, which is inexpensive and widely used in lithography patterning, is preferred.

In the development with an aqueous alkaline solution of a 2.38% tetramethylammonium hydroxide (TMAH) aqueous solution, some negative photosensitive resin compositions used in recent years have small difference in solubility between an exposed part and an unexposed part with respect to the developer. In other words, a so-called dissolution contrast therebetween is sometimes small. When the dissolution contrast is small, it cannot be always expected to form a good pattern satisfying a demand of a fine pattern. Moreover, when the dissolution contrast is small, there is fear that a pattern cannot be formed on a substrate accurately according to a mask used for transferring and forming a pattern by exposure. Therefore, the photosensitive resin composition requires dissolution contrast as high as possible, i.e., improvement of resolution in use of an aqueous alkaline developer.

Accordingly, the photosensitive composition is desired to be capable of forming a fine pattern in the rewiring technology with the trends to higher density and higher integration of chips and to be useful for a top coat to protect electric and electronic parts as well as to have dramatically improved adhesiveness to a substrate. Moreover, it is desired that the contact hole for forming a through electrode connecting a metal wiring has a forward tapered shape. Furthermore, wanted is prompt building up of the system in which patterning is possible by a widely used alkaline developer such as a 2.38% TMAH aqueous solution, further improvement of resolution can be expected, and a scum and a footing profile are not generated in the pattern bottom.

PRIOR ART DOCUMENTS

Patent Documents

Patent Document 1: Japanese Patent Laid-Open Publication No. 2008-184571
Patent Document 2: Japanese Patent Laid-Open Publication No. 2009-200315

SUMMARY OF THE INVENTION

The present invention was accomplished in view of the above-described problems. It is an object of the present invention to provide a positive photosensitive resin composition that can remedy the problem of delamination caused on a metal wiring such as Cu and Al, an electrode, and a substrate, especially on a substrate such as SiN, and can form a fine pattern having a forward tapered shape without generating a scum and a footing profile in the pattern bottom and on the substrate when a widely used 2.38% TMAH aqueous solution is used as the developer.

Another object of the present invention is to provide a patterning process in which the above-mentioned positive photosensitive resin composition is easily applied on a substrate by the spin coating method to form a fine pattern.

Further object of the present invention is to provide a photo-curable dry film using the positive photosensitive resin composition, a method for producing the same, a laminate having the photo-curable dry film laminated on a substrate, and a patterning process in which a resist layer having a wide range of film thickness is formed even on an uneven substrate by using the photo-curable dry film to form a fine pattern.

To achieve this object, the present invention provides a positive photosensitive resin composition comprising:

(A) a polymer compound containing a siloxane chain, the polymer compound having a repeating unit shown by the following general formula (1) and a weight average molecular weight of 3,000 to 500,000;

(B) a photosensitive material capable of generating an acid by light and increasing a dissolution rate in an aqueous alkaline solution;

(C) one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group and shown by the following formula (C-2); and (D) a solvent,

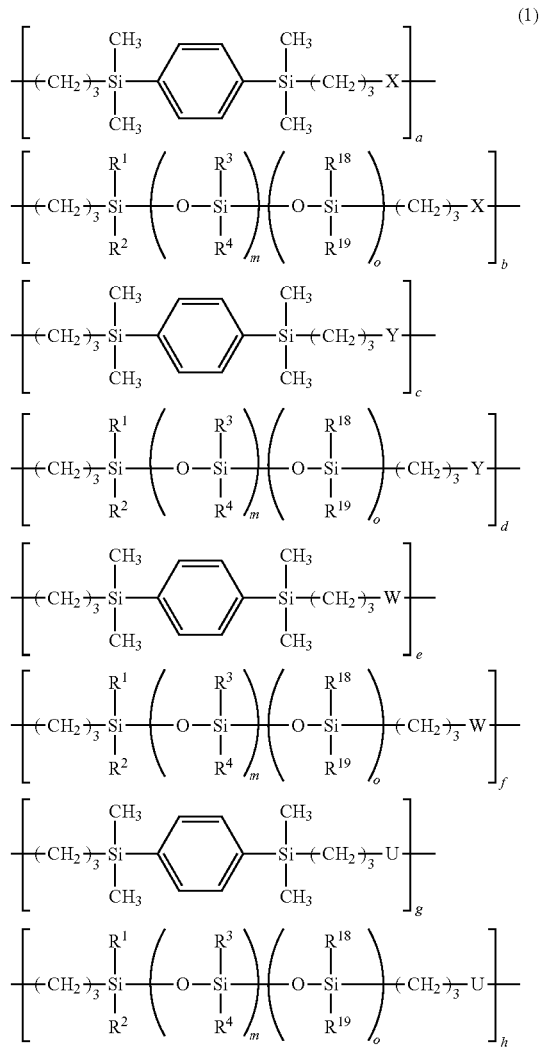

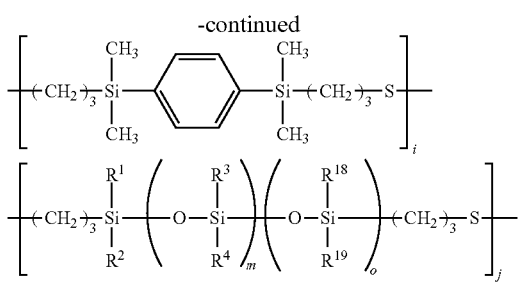

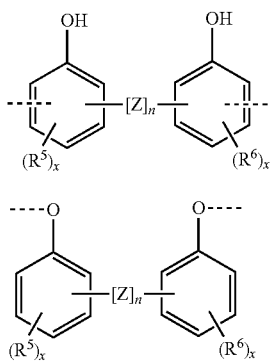

wherein $R^1$ to $R^4$ are the same or different and represent a monovalent organic group having 1 to 15 carbon atoms and optionally containing an oxygen atom; $R^{18}$ and $R^{19}$ are the same or different and represent a monovalent organic group having 1 to 28 carbon atoms and optionally containing an oxygen atom; "m" represents an integer of 1 to 100; "o" represents an integer of 0 to 100; "a", "b", "c", "d", "e" "f", "g", "h", "i", and "j" are each 0 or a positive number, provided that when "g" and "h" are 0, "i" and "j" are a positive number, and when "i" and "j" are 0, "g" and "h" are a positive number; a+b+c+d+e+f+g+h+i+j=1; X represents a divalent organic group shown by the following general formula (2) or the following general formula (3); Y represents a divalent organic group shown by the following general formula (4); W represents a divalent organic group shown by the following general formula (5); U represents a divalent organic group shown by the following general formula (6); and S represents a divalent organic group shown by the following general formula (7),

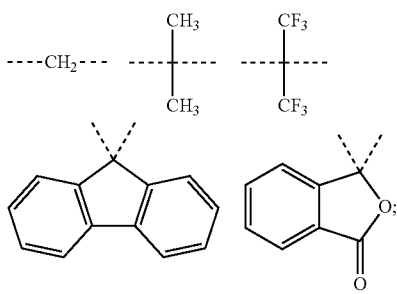

wherein Z represents a divalent organic group selected from any of the dotted line represents a bond; "n" represents 0 or 1; $R^5$ and $R^6$ each represent an alkyl group or alkoxy group having 1 to 4 carbon atoms and are the same or different from each other; and "x" represents 0, 1, or 2;

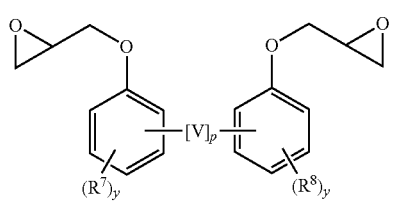

wherein V represents a divalent organic group selected from any of

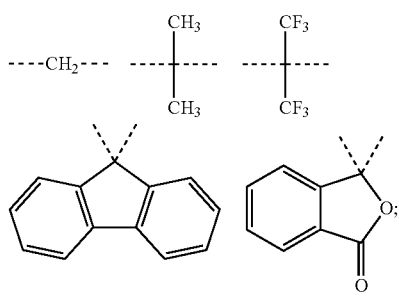

the dotted line represents a bond; "p" represents 0 or 1; $R^7$ and $R^8$ each represent an alkyl group or alkoxy group having 1 to 4 carbon atoms and are the same or different from each other; and "y" represents 0, 1, or 2;

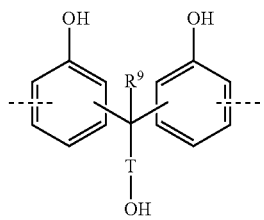

wherein the dotted line represents a bond; T represents an alkylene group having 1 to 10 carbon atoms or a divalent aromatic group; and $R^9$ represents a hydrogen atom or a methyl group;

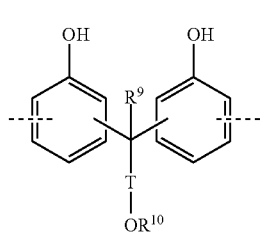

wherein the dotted line represents a bond; T and $R^9$ have the same meanings as defined above; and $R^{10}$ represents a monovalent carboxyl-containing organic group,

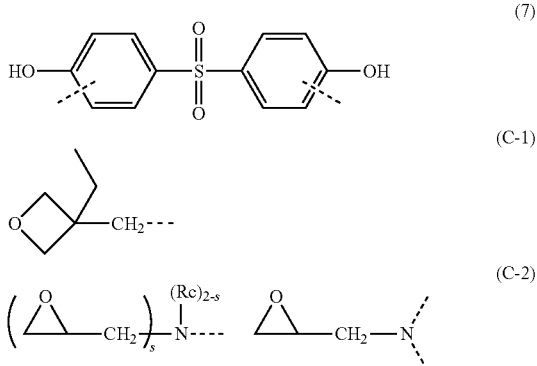

(7)

(C-1)

(C-2)

wherein the dotted line represents a bond; Rc represents a linear, branched, or cyclic alkyl group having 1 to 6 carbon atoms; and "s" represents 1 or 2.

This positive photosensitive resin composition can remedy the problem of delamination caused on a metal wiring such as Cu and Al, an electrode, and a substrate, especially on a substrate such as SiN, and can form a fine pattern having a forward tapered shape without generating a scum and a footing profile in the pattern bottom and on the substrate when a widely used 2.38% TMAH aqueous solution is used as the developer.

In this composition, $R^{10}$ in the general formula (6) is preferably a monovalent carboxyl-containing organic group shown by the following general formula (8),

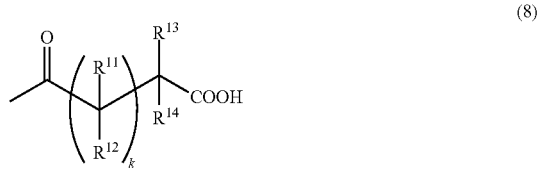

(8)

wherein the dotted line represents a bond; $R^{11}$ to $R^{14}$ are the same or different and represent a hydrogen atom, a halogen atom, a linear, branched, or cyclic alkyl group having 1 to 12 carbon atoms, or an aromatic group; $R^{11}$ and $R^{13}$ are optionally respectively bonded to $R^{12}$ and $R^{14}$ to form a substituted or unsubstituted ring structure having 1 to 12 carbon atoms; and "k" is any of 1 to 7.

The positive photosensitive resin composition containing such component (A) can improve the effect of the present invention.

Preferably, in the general formula (1), 0≤a≤0.5, 0≤b≤0.3, 0≤c≤0.5, 0≤d≤0.3, 0≤e≤0.8, 0≤f≤0.5, 0≤g≤0.8, 0≤h≤0.5, 0≤i≤0.8, and 0≤j≤0.5.

More preferably, in the general formula (1), a=0, b=0, c=0, d=0, 0≤e≤0.3, 0≤f≤0.2, 0≤g≤0.8, 0≤h≤0.5, 0≤i≤0.8, and 0≤j≤0.5.

The positive photosensitive resin composition containing such component (A) can further improve the effect of the present invention.

Preferably, in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

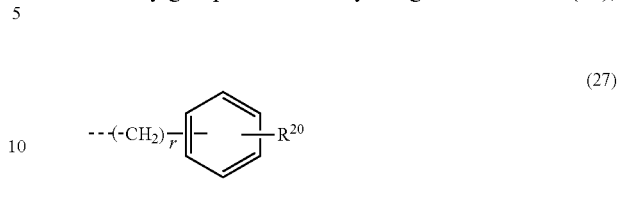

(27)

wherein "r" represents an integer of 0 to 10; and $R^{20}$ represents a hydroxyl group or a linear, branched, or cyclic alkoxy group having 1 to 12 carbon atoms.

The positive photosensitive resin composition using such component (A) as the base resin can improve crosslinking reactivity at an unexposed part after patterning. By improving the crosslinking reactivity at an unexposed part, a cured film excellent in adhesiveness, heat resistance, electric characteristics, mechanical strength, chemical resistance, reliability, and crack resistance can be obtained.

The phenyl substituent shown by the general formula (27) is preferably one group, or two or more groups selected from the following formulae (28),

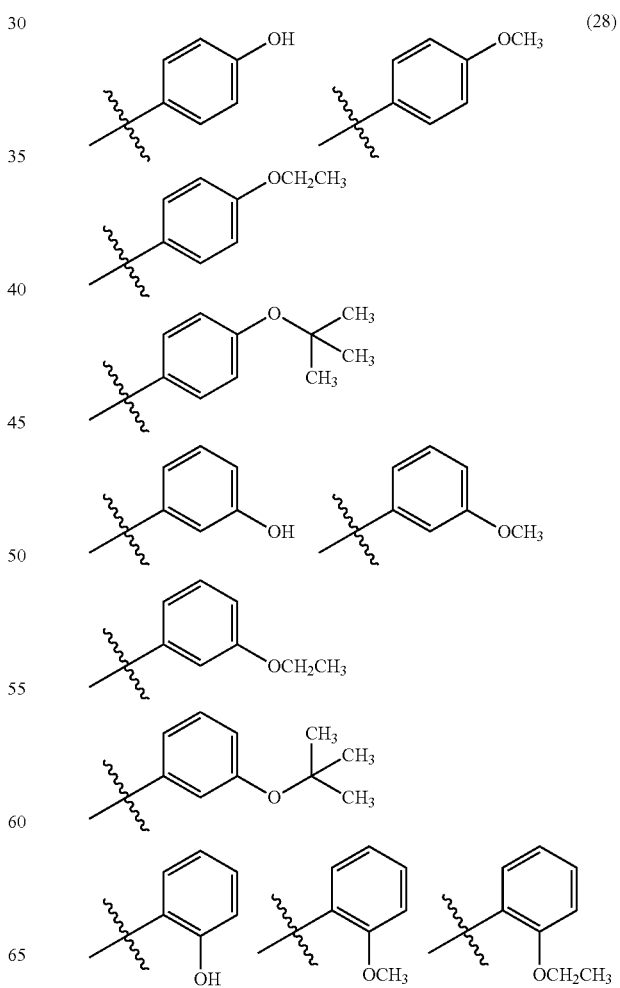

(28)

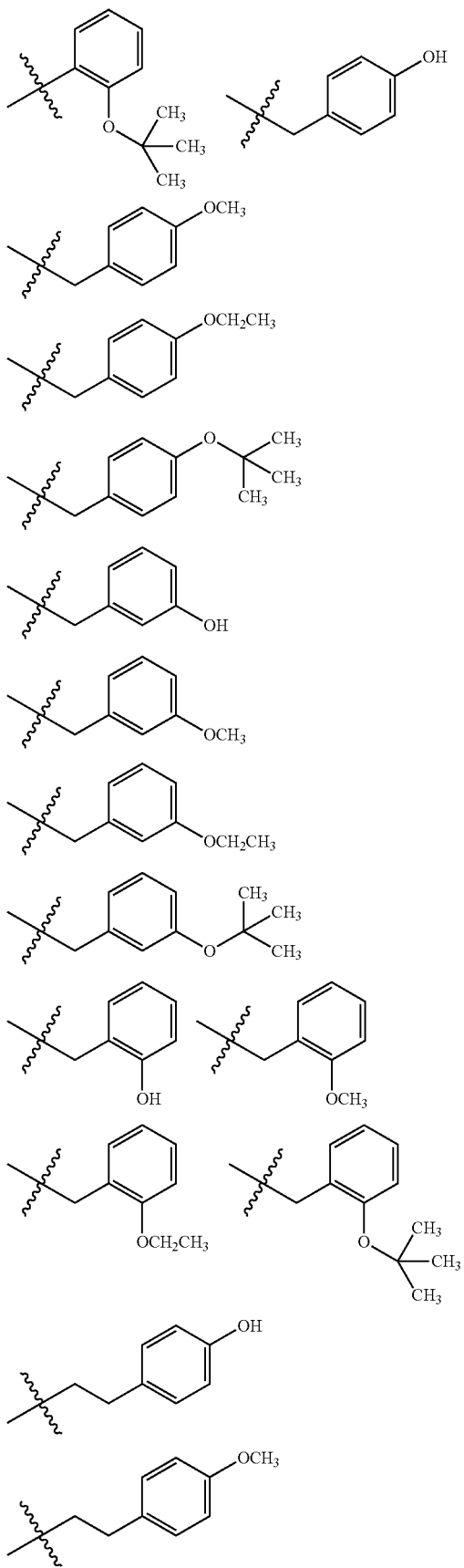
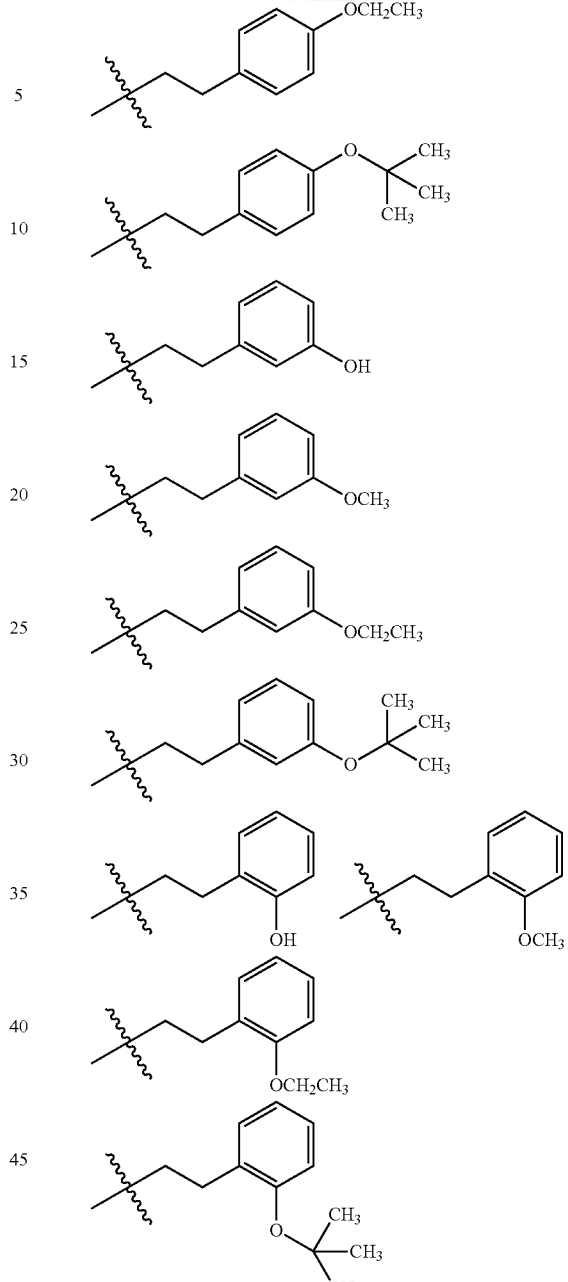

wherein the line with a wavy line represents a bonding arm.

The positive photosensitive resin composition using such component (A) as the base resin can more greatly improve the crosslinking reactivity at an unexposed part after patterning. By more greatly improving the crosslinking reactivity at an unexposed part, a cured film more excellent in adhesiveness, heat resistance, electric characteristics, mechanical strength, chemical resistance, reliability, and crack resistance can be obtained.

Furthermore, the present invention provides a photo-curable dry film comprising a supporting film, a protective film, and a photo-curable resin layer having a thickness of 10 to 100 μm and sandwiched between the supporting film and the protective film, wherein the photo-curable resin layer is formed of the above-mentioned positive photosensitive resin composition.

This photo-curable dry film can form a fine pattern in wide ranges of film thickness and wavelength, and can be post-cured at low temperature to give a cured film having excellent flexibility, heat resistance, electric characteristics, adhesiveness, reliability, and chemical resistance.

Furthermore, the present invention provides a method for producing a photo-curable dry film, comprising:

(I) continuously applying the above-mentioned positive photosensitive resin composition onto a supporting film to form a photo-curable resin layer, (II) continuously drying the photo-curable resin layer, and further (III) laminating a protective film on the photo-curable resin layer.

This producing method is suitable for providing the above-mentioned photo-curable dry film.

Furthermore, the present invention provides a patterning process comprising:

(1) applying the above-mentioned positive photosensitive resin composition onto a substrate to form a photosensitive material film;

(2) exposing the photosensitive material film to a high energy beam having a wavelength of 190 to 500 nm or an electron beam via a photomask after a heat treatment; and (3) performing development with a developer after a heat treatment.

This patterning process can remedy the problem of delamination caused on a metal wiring such as Cu and Al, an electrode, and a substrate, especially on a substrate such as SiN, and can easily form an extremely fine pattern having a forward tapered shape without generating a scum and a footing profile in the pattern bottom and on the substrate when a widely used 2.38% TMAH aqueous solution is used as the developer. Moreover, the positive photosensitive resin composition can be applied by the spin coating method.

Furthermore, the present invention provides a patterning process comprising:

(i) separating the protective film from the above-mentioned photo-curable dry film and bringing the photo-curable resin layer thereby uncovered into close contact with a substrate;

(ii) exposing the photo-curable resin layer to a high energy beam having a wavelength of 190 to 500 nm or an electron beam via a photomask either through the supporting film or after removing the supporting film;

(iii) performing a heat treatment after the exposure; and (iv) performing development with a developer.

This patterning process can remedy the problem of delamination caused on a metal wiring such as Cu and Al, an electrode, and a substrate, especially on a substrate such as SiN, and can easily form an extremely fine pattern having a forward tapered shape without generating a scum and a footing profile in the pattern bottom and on the substrate when a widely used 2.38% TMAH aqueous solution is used as the developer.

The patterning process preferably further comprises post-curing a patterned film formed by the development at 100 to 250° C. after the development.

The cured film thus obtained has excellent flexibility, adhesiveness to a substrate, heat resistance, electric characteristics, mechanical strength, and chemical resistance to a soldering flux liquid. Thus, a semiconductor device having such a cured film as the top coat has excellent reliability, and especially can be prevented from causing cracks during a thermal cycle test.

The substrate preferably includes a trench and/or a hole having an aperture width of 10 to 100 μm and a depth of 10 to 120 μm.

The photo-curable dry film of the present invention allows a resist layer with a wide range of thickness and then a fine pattern to be formed on an uneven substrate.

Furthermore, the present invention provides a laminate comprising a substrate including a trench and/or a hole having an aperture width of 10 to 100 μm and a depth of 10 to 120 μm, and the above-mentioned photo-curable resin layer of the photo-curable dry film laminated on the substrate.

This laminate allows the above-mentioned pattern to be adequately filled and is excellent in various properties.

As mentioned above, the present invention can provide a positive photosensitive resin composition that can dramatically remedy the problem of delamination caused on a metal wiring such as Cu and Al, an electrode, and a substrate, especially on a substrate such as SiN. This positive photosensitive resin composition allows a fine pattern having a forward tapered shape to be easily formed without generating a scum and a footing profile in a wide range of wavelength; thus, this composition is suitable for patterning in the rewiring technology with the trends to higher density and higher integration of chips. Moreover, this positive photosensitive resin composition can be developed with an aqueous alkaline solution such as a 2.38% TMAH aqueous solution, thus providing a photo-curable dry film using the positive photosensitive resin composition and a patterning process using the same. By post-curing a pattern obtained by such a patterning process at low temperature, a substrate protected by a cured film excellent in flexibility, adhesiveness, heat resistance, electric characteristics, mechanical strength, chemical resistance, reliability, and crack resistance can be obtained.

BRIEF DESCRIPTION OF THE DRAWING

FIG. 1 is an explanatory view showing an adhesiveness measurement method in Examples.

DETAILED DESCRIPTION OF THE PREFERRED EMBODIMENTS

As mentioned above, it is desired to develop a positive photosensitive resin composition that can remedy the problem of delamination caused on a metal wiring such as Cu and Al, an electrode, and a substrate, especially on a substrate such as SiN, can easily form an extremely fine pattern having a forward tapered shape without generating a scum and a footing profile in the pattern bottom and on the substrate by using a widely used 2.38% TMAH aqueous solution, and can provide a cured film excellent in mechanical strength, chemical resistance, reliability, and so forth.

The present inventors have earnestly investigated to achieve the above object and consequently found that a polymer compound containing alcoholic or phenolic hydroxyl groups (a silicone-skeleton-containing polymer compound) can be obtained by polymerization reaction of a phenol compound having two allyl groups as shown by the following formula (15) with a hydrogensilphenylene shown by the following formula (10), a dihydroorganosiloxane shown by the following formula (11), a phenol compound having two allyl groups as shown by the following formula (12) or (13), a phenol compound having two allyl groups as shown by the following formula (14), and a compound having two allyl groups as shown by the following formula

(20) in the presence of a catalyst, and then a carboxyl group can be introduced to the silicone skeleton by reacting a part or all of the alcoholic or phenolic hydroxyl groups of the resulting polymer compound with dicarboxylic anhydride, whereby a polymer compound having a repeating unit shown by the general formula (1) can be obtained.

Moreover, the present inventors found that a positive photosensitive resin composition containing the following components (A) to (D), in which the component (A), a siloxane-chain-containing polymer compound having a repeating unit shown by the general formula (1), is used as the base resin, can form a fine pattern with good shape and can dramatically remedy the problem of delamination caused on a metal wiring such as Cu and Al, an electrode, and a substrate, especially on a substrate such as SiN, thus dramatically improving the adhesiveness to substrate. Furthermore, they found that a cured film obtained by post-curing a pattern formed with the above-mentioned positive photosensitive resin composition is excellent as a top coat to protect electric and electronic parts, thereby bringing the present invention to completion.

That is, the present invention is a positive photosensitive resin composition comprising:

(A) a polymer compound containing a siloxane chain, the polymer compound having a repeating unit shown by the general formula (1) and a weight average molecular weight of 3,000 to 500,000;

(B) a photosensitive material capable of generating an acid by light and increasing a dissolution rate in an aqueous alkaline solution;

(C) one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the formula (C-1), and a compound containing two or more nitrogen atoms having a glycidyl group and shown by the formula (C-2); and (D) a solvent.

Hereinafter, the present invention will be described in detail, but the present invention is not limited thereto.

[Positive Photosensitive Resin Composition]

The positive photosensitive resin composition of the present invention contains the following components (A) to (D).

<Component (A)>

The component (A) used as the base resin of the positive photosensitive resin composition of the present invention is a polymer compound (silicone-skeleton-containing polymer compound) containing a siloxane chain, having a repeating unit shown by the following general formula (1) and a weight average molecular weight of 3,000 to 500,000,

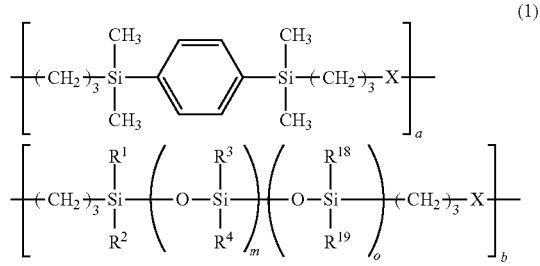

(1)

-continued

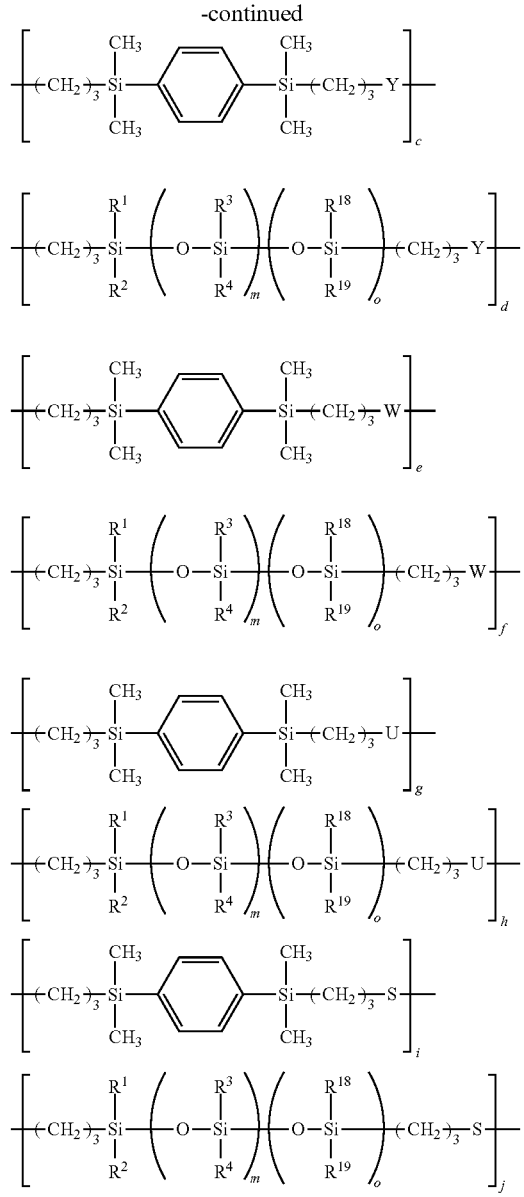

wherein $R^1$ to $R^4$ are the same or different and represent a monovalent organic group having 1 to 15 carbon atoms and optionally containing an oxygen atom; $R^{18}$ and $R^{19}$ are the same or different and represent a monovalent organic group having 1 to 28 carbon atoms and optionally containing an oxygen atom; "m" represents an integer of 1 to 100; "o" represents an integer of 0 to 100; "a", "b", "c", "d", "e" "f", "g", "h", "i", and "j" are each 0 or a positive number, provided that when "g" and "h" are 0, "i" and "j" are a positive number, and when "i" and "j" are 0, "g" and "h" are a positive number; a+b+c+d+e+f+g+h+i+j=1; X represents a divalent organic group shown by the following general formula (2) or the following general formula (3); Y represents a divalent organic group shown by the following general formula (4); W represents a divalent organic group shown by the following general formula (5); U represents a divalent organic group shown by the following general formula (6); and S represents a divalent organic group shown by the following general formula (7),

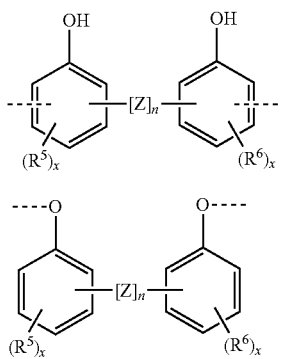

(2)

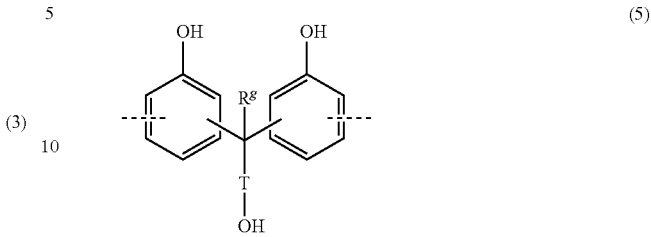

(5)

wherein the dotted line represents a bond; T represents an alkylene group having 1 to 10 carbon atoms or a divalent aromatic group; and $R^9$ represents a hydrogen atom or a methyl group;

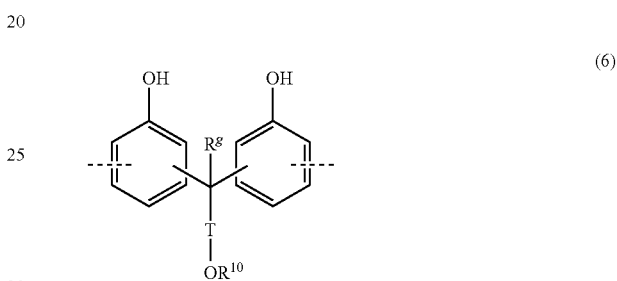

(6)

wherein the dotted line represents a bond; T and $R^9$ have the same meanings as defined above; and $R^{10}$ represents a monovalent carboxyl-containing organic group,

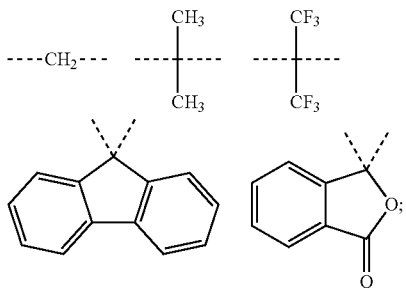

(3)

wherein Z represents a divalent organic group selected from any of

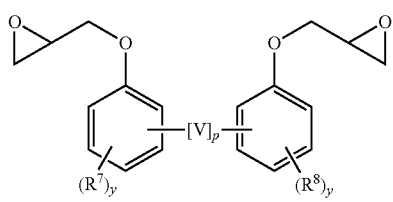

the dotted line represents a bond; "n" represents 0 or 1; $R^5$ and $R^6$ each represent an alkyl group or alkoxy group having 1 to 4 carbon atoms and are the same or different from each other; and "x" represents 0, 1, or 2;

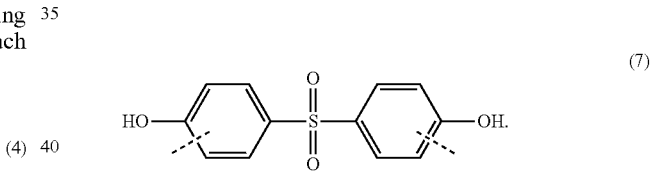

(7)

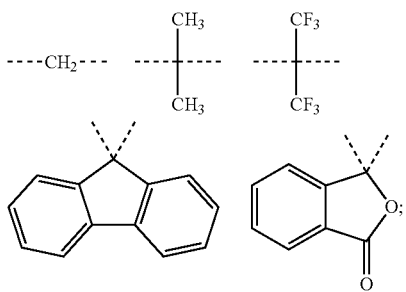

(4)

wherein V represents a divalent organic group selected from any of the dotted line represents a bond; "p" represents 0 or 1; $R^7$ and $R^8$ each represent an alkyl group or alkoxy group having 1 to 4 carbon atoms and are the same or different from each other; and "y" represents 0, 1, or 2;

In the general formula (1), $R^1$ to $R^4$ are the same or different and represent a monovalent organic group having 1 to 15 carbon atoms, preferably 1 to 10 carbon atoms, and optionally containing an oxygen atom; and $R^{18}$ and $R^{19}$ are the same or different and represent a monovalent organic group having 1 to 28 carbon atoms, preferably 1 to 15 carbon atoms, more preferably 1 to 10 carbon atoms, and optionally containing an oxygen atom. Illustrative examples thereof include linear, branched or cyclic alkyl groups such as a methyl group, an ethyl group, a propyl group, an isopropyl group, a n-butyl group, a tert-butyl group, and a cyclohexyl group; linear, branched or cyclic alkenyl groups such as a vinyl group, an allyl group, a propenyl group, a butenyl group, a hexenyl group, and a cyclohexenyl group; aryl groups such as a phenyl group and a tolyl group; and aralkyl groups such as a benzyl group, a phenethyl group, and a methoxyphenethyl group.

In view of the compatibility with a later-described cross-linking agent and photosensitive material, and in view of photo-curability, "m" represents an integer of 1 to 100, preferably 1 to 80. "o" represents an integer of 0 to 100.

"a", "b", "c", "d", "e", "f", "g", "h", "i", and "j" are each 0 or a positive number, provided that when "g" and "h" are 0, "i" and "j" are a positive number, and when "i" and "j" are 0, "g" and "h" are a positive number; and a+b+c+d+e+f+ g+h+i+j=1. The polymer compound satisfying that when "g" and "h" are 0, "i" and "j" are a positive number, and when "i" and "j" are 0, "g" and "h" are a positive number means that the polymer compound used in the positive photosensitive resin composition according to the present invention contains either the divalent organic group (U) shown by the general formula (6) or the divalent organic group (S) shown by the general formula (7). This polymer compound is soluble in an aqueous alkaline developer used for patterning.

In the above formula, "a", "b", "c", "d", "e", "f", "g", "h", "i", and "j" preferably satisfy 0≤a≤0.5, 0≤b≤0.3, 0≤c≤0.5, 0≤d≤0.3, 0≤e≤0.8, 0≤f≤0.5, 0≤g≤0.8, 0≤h≤0.5, 0≤i≤0.8, and 0≤j≤0.5.

In particular, "a", "b", "c", "d", "e", "f", "g", "h", "i", and "j" more preferably satisfy:
i. 0≤a≤0.5, 0≤b≤0.3, 0≤c≤0.5, 0≤d≤0.3, 0≤e≤0.8, 0≤f≤0.5, 0<g≤0.8, 0<h≤0.5, 0≤i≤0.8, and 0≤j≤0.5;
ii. 0≤a≤0.5, 0≤b≤0.3, 0≤c≤0.5, 0≤d≤0.3, 0≤e≤0.8, 0≤f≤0.5, 0≤g≤0.8, 0≤h≤0.5, 0<i≤0.8, and 0<j≤0.5;
iii. 0≤a≤0.5, 0≤b≤0.3, c=0, d=0, 0≤e≤0.8, 0≤f≤0.5, 0≤g≤0.8, 0<h≤0.5, 0≤i≤0.8, and 0≤j≤0.5;
iv. 0≤a≤0.5, 0≤b≤0.3, c=0, d=0, 0≤e≤0.8, 0≤f≤0.5, 0≤g≤0.8, 0≤h≤0.5, 0<i≤0.8, and 0<j≤0.5;
v. a=0, b=0, 0≤c≤0.5, 0≤d≤0.3, 0≤e≤0.8, 0≤f≤0.5, 0≤g≤0.8, 0<h≤0.5, 0≤i≤0.8, and 0≤j≤0.5;
vi. a=0, b=0, 0≤c≤0.5, 0≤d≤0.3, 0≤e≤0.8, 0≤f≤0.5, 0≤g≤0.8, 0≤h≤0.5, 0<i≤0.8, and 0<j≤0.5;
vii. a=0, b=0, c=0, d=0, 0≤e≤0.3, 0≤f≤0.2, 0≤g≤0.8, 0<h≤0.5, 0≤i≤0.8, and 0≤j≤0.5;
viii. a=0, b=0, c=0, d=0, 0≤e≤0.3, 0≤f≤0.2, 0≤g≤0.8, 0≤h≤0.5, 0<i≤0.8, and 0<j≤0.5;
ix. a=0, b=0, c=0, d=0, e=0, f=0, 0<g≤0.8, 0<h≤0.5, 0≤i≤0.8, and 0≤j≤0.5;
x. a=0, b=0, c=0, d=0, e=0, f=0, 0≤g≤0.8, 0≤h≤0.5, 0<i≤0.8, and 0<j≤0.5.

In this case, preferable range of "e" is 0≤e≤0.8, more preferably 0≤e≤0.6, much more preferably 0≤e≤0.3.

Moreover, preferable range of "f" is 0<f≤0.5, more preferably 0<f≤0.3. When "f" is 0.5 or less, there is no fear that the polymer compound is difficult to dissolve in an aqueous alkaline developer at patterning with the aqueous alkaline developer, which is object of the present invention. When "f" is 0.5 or less, there is no fear that a formed film is so viscous that its processability is lowered; and there is no fear that when the inventive photo-curable dry film having a layer sandwiched between a supporting film and a protective film is produced, the protective film cannot be separated, and thus the product cannot be used as the photo-curable dry film.

Moreover, when "i" is 0, preferable range of "g" is 0<g≤0.8, more preferably 0.2≤g≤0.8. When "g" is 0.2 or more, the solubility in an aqueous alkaline developer is not lowered, so that a good pattern can be obtained. That is, when "g" is 0.2 or more and thus an exposed part of a positive pattern has excellent solubility in an aqueous alkaline developer, the pattern deterioration such as undissolved residues and scum in the pattern bottom and a footing profile in the pattern on the substrate can be prevented even if the positive photosensitive resin composition forms a thick coating film on the substrate. In addition, a fine pattern can be formed.

Preferable range of "h" is 0<h≤0.5, more preferably 0<h≤0.3.

Similarly, when "g" is 0, preferable range of "i" is 0<i≤0.8, more preferably 0.2≤i≤0.8. When "i" is 0.2 or more, the solubility in an aqueous alkaline developer is not lowered, so that a good pattern can be obtained. That is, when "i" is 0.2 or more and thus an exposed part of a positive pattern has excellent solubility in an aqueous alkaline developer, the pattern deterioration such as undissolved residues and scum in the pattern bottom and a footing profile in the pattern on the substrate can be prevented even if the positive photosensitive resin composition forms a thick coating film on the substrate. In addition, a fine pattern can be formed.

Preferable range of "j" is 0<j≤0.5, more preferably 0<j≤0.3.

In the general formula (1), X represents a divalent organic group shown by the following general formula (2) or the following general formula (3); Y represents a divalent organic group shown by the following general formula (4); W represents a divalent organic group shown by the following general formula (5); U represents a divalent organic group shown by the following general formula (6); and S represents a divalent organic group shown by the following general formula (7),

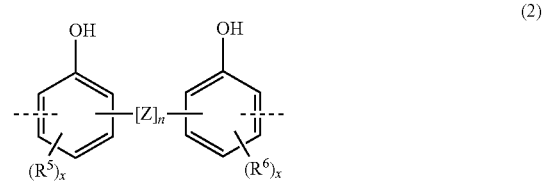

(2)

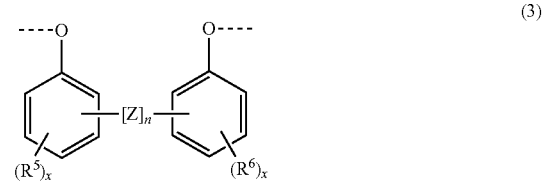

(3)

wherein Z represents a divalent organic group selected from any of

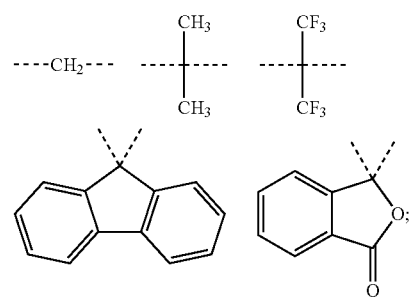

the dotted line represents a bond; "n" represents 0 or 1; $R^5$ and $R^6$ each represent an alkyl group or alkoxy group having 1 to 4 carbon atoms and are the same or different from each other; and "x" represents 0, 1, or 2;

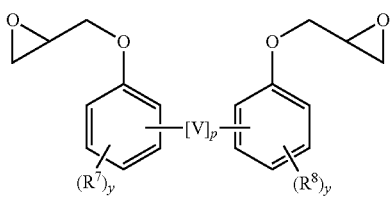
(4)

wherein V represents a divalent organic group selected from any of

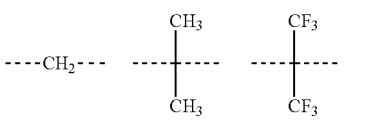

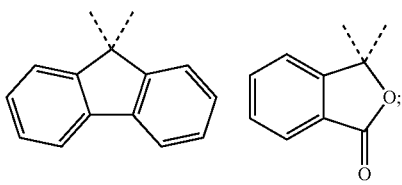

the dotted line represents a bond; "p" represents 0 or 1; $R^7$ and $R^8$ each represent an alkyl group or alkoxy group having 1 to 4 carbon atoms and are the same or different from each other; and "y" represents 0, 1, or 2;

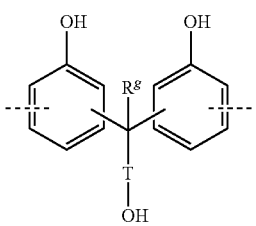
(5)

wherein the dotted line represents a bond; T represents an alkylene group having 1 to 10 carbon atoms or a divalent aromatic group; and $R^9$ represents a hydrogen atom or a methyl group;

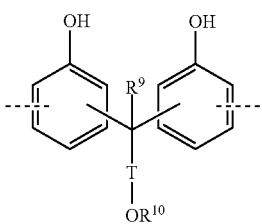
(6)

wherein the dotted line represents a bond; T and $R^9$ have the same meanings as defined above; and $R^{10}$ represents a monovalent carboxyl-containing organic group,

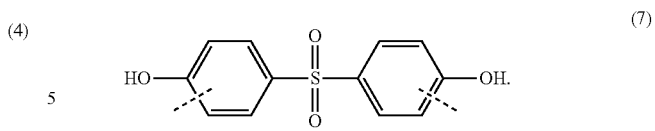
(7)

In the general formula (6), $R^{10}$ is preferably a monovalent carboxyl-containing organic group shown by the following general formula (8),

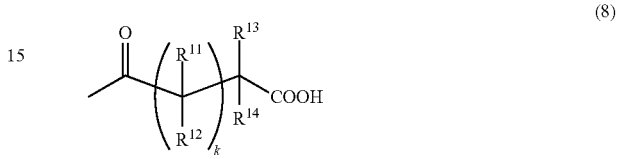
(8)

wherein the dotted line represents a bond; $R^{11}$ to $R^{14}$ are the same or different and represent a hydrogen atom, a halogen atom, a linear, branched, or cyclic alkyl group having 1 to 12 carbon atoms, or an aromatic group; $R^{11}$ and $R^{13}$ are optionally respectively bonded to $R^{12}$ and $R^{14}$ to form a substituted or unsubstituted ring structure having 1 to 12 carbon atoms; and "k" is any of 1 to 7.

In addition, it is preferred that in the general formula (1), "o" is an integer of 1 to 100, preferably 1 to 80; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms, preferably a monovalent hydrocarbon group having 1 to 8 carbon atoms, and optionally containing an oxygen atom, or $R^{19}$ is the same as or different from $R^{18}$ and represents a phenyl substituent containing a hydroxyl group or an alkoxy group and shown by the general formula (27),

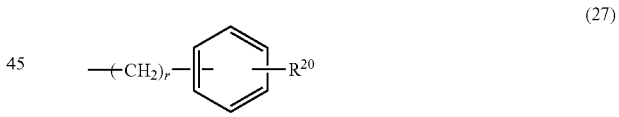
(27)

wherein "r" represents an integer of 0 to 10; and $R^{20}$ represents a hydroxyl group or a linear, branched, or cyclic alkoxy group having 1 to 12 carbon atoms.

In the phenyl substituent shown by the general formula (27), the hydroxyl group or the alkoxy group may be substituted in any of o-, m-, and p-positions. When $R^{20}$ represents the alkoxy group, the number of carbon atoms is 1 to 12, preferably 1 to 4.

Illustrative examples of the phenyl substituent shown by the general formula (27) include groups shown by the formulae (28). In the formulae (28), the line with a wavy line:

represents a bonding arm.
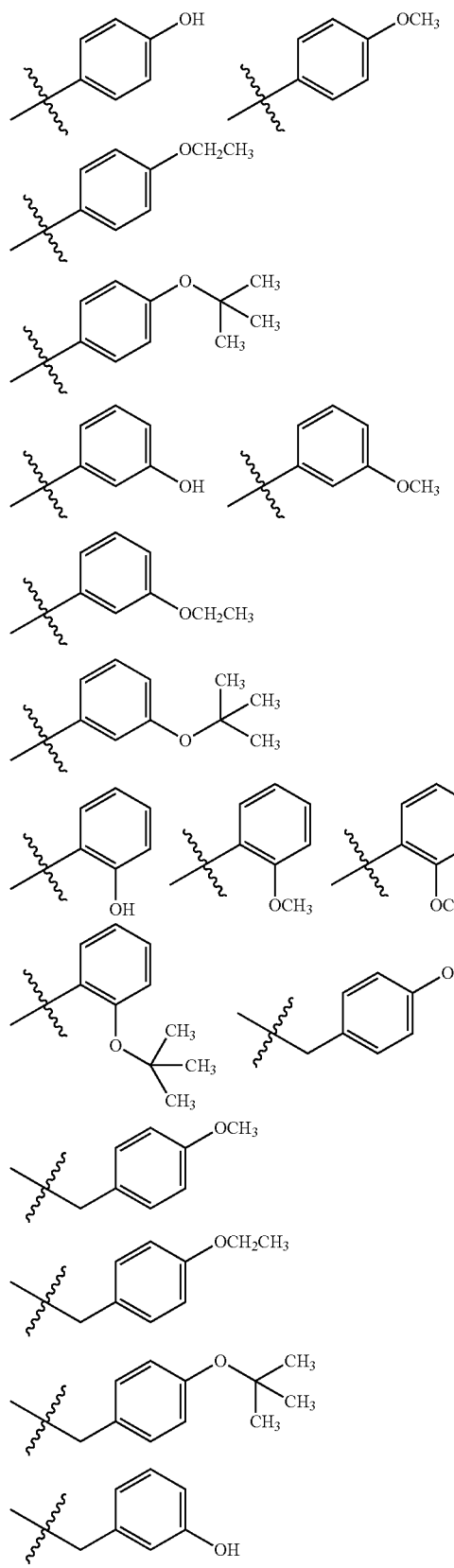
(28)
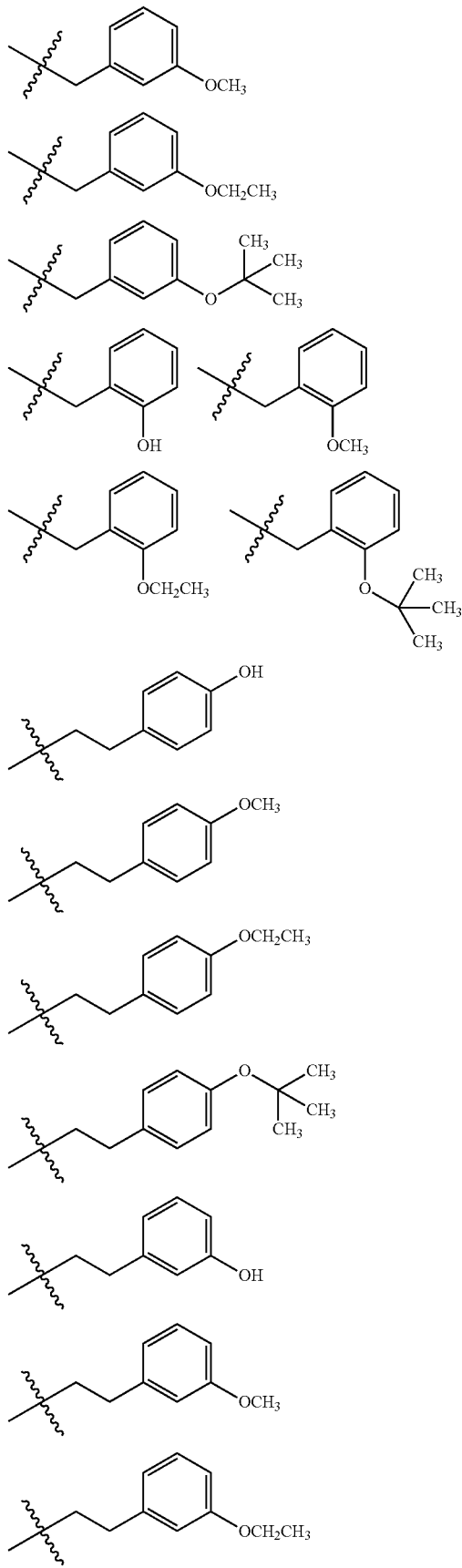

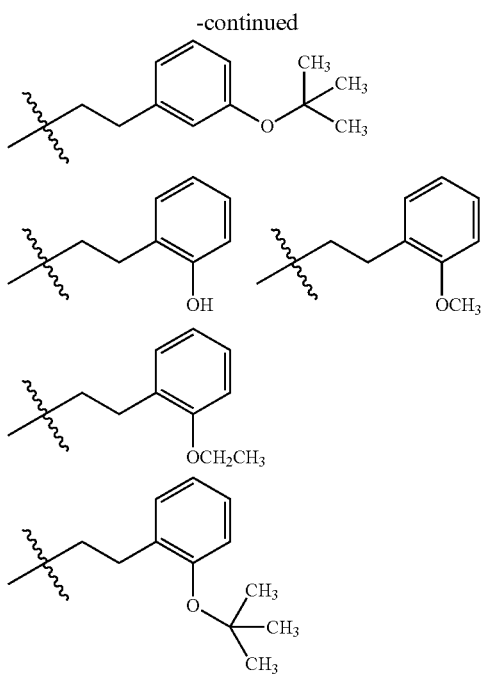

The positive photosensitive resin composition using the polymer compound having the phenyl substituent shown by the general formula (27) as the base resin can improve the crosslinking reactivity at an unexposed part after patterning. The reason is that crosslinking points in the polymer compound is remarkably increased due to the additional crosslinking points on the siloxane, thus progressing the reaction with a later-described crosslinking agent more greatly. By improving the crosslinking reactivity at an unexposed part, a cured film excellent in adhesiveness, heat resistance, electric characteristics, mechanical strength, chemical resistance, reliability, and crack resistance can be obtained.

Examples of the usable polymer compound of component (A) include a compound having a repeating unit shown by the following general formula (24) and a weight average molecular weight of 3,000 to 500,000,

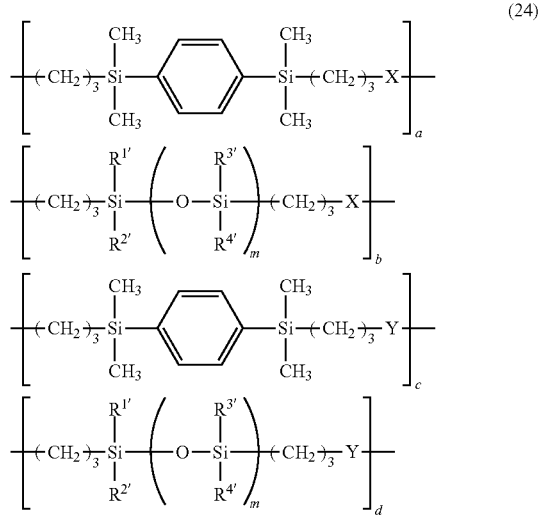

(24)

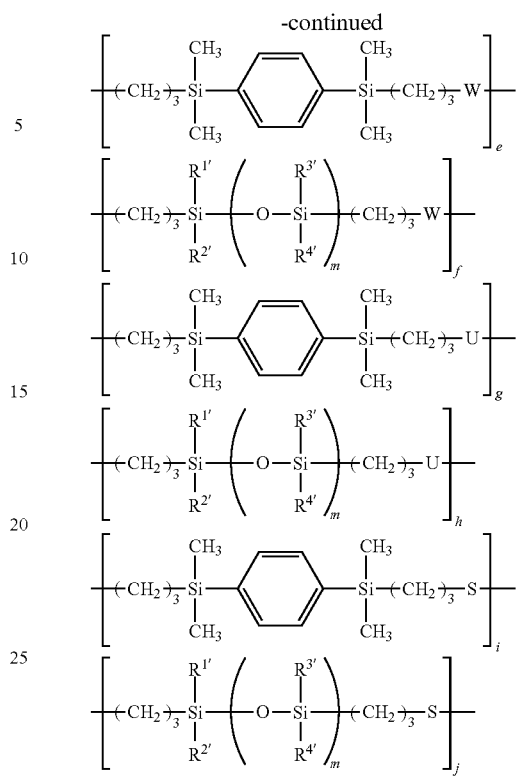

wherein "a", "b", "c", "d", "e", "f", "g", "h", "i", "j", "m", X, Y, W, U, and S have the same meanings as defined above; and $R^{1'}$ to $R^{4'}$ are the same or different and represent a monovalent hydrocarbon group having 1 to 8 carbon atoms.

Illustrative examples thereof include linear, branched or cyclic alkyl groups such as a methyl group, an ethyl group, a propyl group, an isopropyl group, a n-butyl group, a tert-butyl group, and a cyclohexyl group; linear, branched or cyclic alkenyl groups such as a vinyl group, an allyl group, a propenyl group, a butenyl group, a hexenyl group, and a cyclohexenyl group; aryl groups such as a phenyl group and a tolyl group; and aralkyl groups such as a benzyl group and a phenethyl group.

The component (A) in the present invention has a weight average molecular weight of 3,000 to 500,000, preferably 5,000 to 300,000, more preferably 10,000 to 50,000 in view of the compatibility and the photo-curability of the positive photosensitive resin composition of the present invention, and in view of mechanical characteristics of a cured product obtained from the positive photosensitive resin composition. Herein, the weight average molecular weight is determined by gel permeation chromatography (GPC) in terms of polystyrene.

Then, a method for producing the polymer compound of component (A) will be described.

The polymer compound of component (A) can be produced by reacting a part or all of alcoholic or phenolic hydroxyl groups of a polymer compound (a silicone-skeleton-containing polymer compound) having a repeating unit shown by the following general formula (9) with dicarboxylic anhydride to introduce a carboxyl group into the polymer compound.

In the method for producing the polymer compound of component (A), the polymer compound having a repeating unit shown by the general formula (9) may be used as an intermediate raw material.

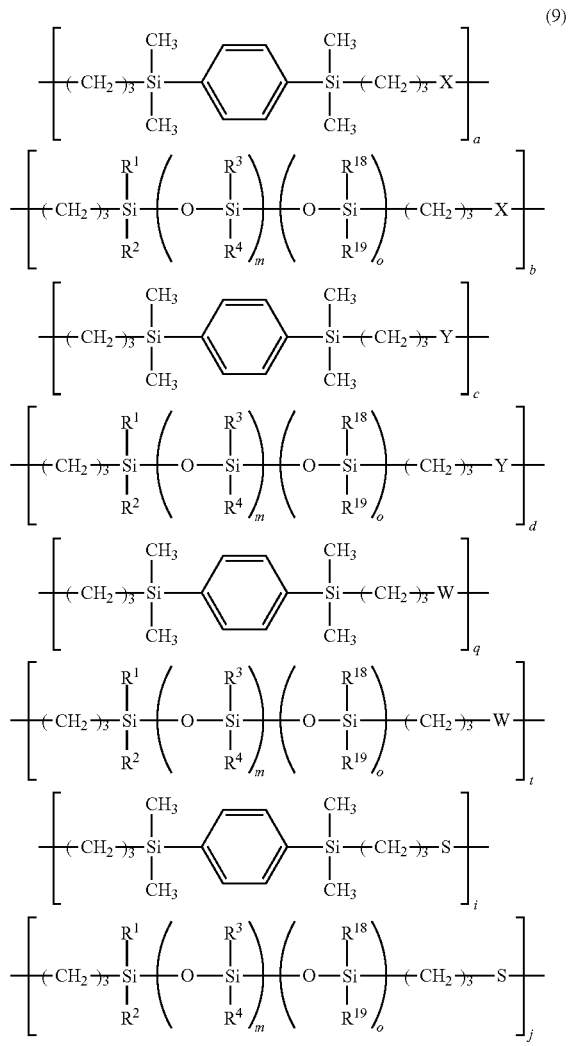

wherein $R^1$ to $R^4$, $R^{18}$ and $R^{19}$, "a", "b", "c", "d", "i", "j", "m", "o", X, Y, W, and S have the same meanings as defined above; "q" and "t" are each a positive number satisfying q=e+g and t=f+h; and "e", "f", "g", and "h" have the same meanings as defined above.

When the weight average molecular weight of the polymer compound having a repeating unit shown by the general formula (9) which is used as an intermediate raw material is decreased, the average molecular weight of the objective polymer compound of component (A) is also decreased, resulting in the positive photosensitive resin composition with a low viscosity. Thus, the viscosity of a resin layer formed from the positive photosensitive resin composition using this polymer compound of component (A) is also decreased. Moreover, in the molecule of the polymer compound of component (A), when the proportion of the molecular units containing a linear polysiloxane (i.e. "b", "d", "f", "h", and "j" in the general formula (1)) is increased, the proportion of the molecular units containing an aromatic compound such as silphenylene (i.e. "a", "c", "e", "g", and "i" in the general formula (1)) is relatively decreased, resulting in the polymer compound of component (A) with a low viscosity. Thus, the viscosity of a resin layer formed from the positive photosensitive resin composition using this polymer compound of component (A) is also decreased.

Furthermore, in the molecule of the polymer compound of component (A), when the molecular chain length of the linear polysiloxane is increased, i.e., when the value of "m" in the general formula (1) is increased, the viscosity of the polymer compound of component (A) is decreased. Thus, the viscosity of a resin layer formed from the positive photosensitive resin composition using this polymer compound of component (A) is also decreased.

The polymer compound having a repeating unit shown by the general formula (9) can be obtained, in the presence of a catalyst, by so-called "hydrosilylation" polymerization reaction of:

a hydrogensilphenylene (1,4-bis(dimethylsilyl)benzene) shown by the structural formula (10) or a mixture of this hydrogensilphenylene and a dihydroorganosiloxane shown by the general formula (11)

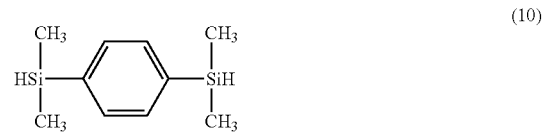

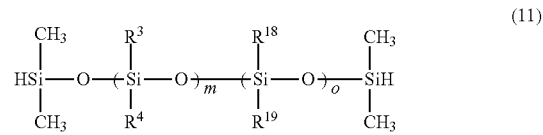

wherein $R^3$, $R^4$, $R^{18}$, $R^{19}$, "m", and "o" have the same meanings as defined above;

either or both of a phenol compound having two allyl groups and shown by the general formula (12) or (13) and a compound having two allyl groups and shown by the general formula (14),

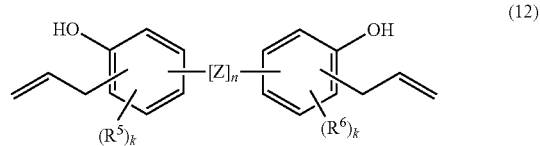

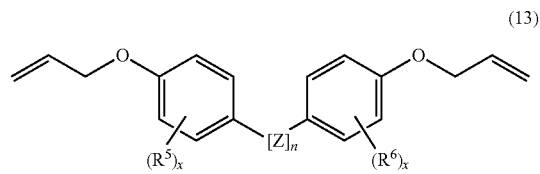

wherein Z, $R^5$, $R^6$, "n" and "x" have the same meanings as defined above,

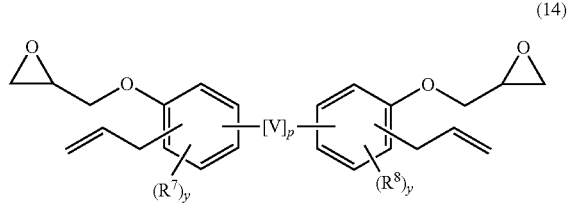

wherein V, $R^7$, $R^8$, "p" and "y" have the same meanings as defined above;

a phenol compound having two allyl groups and shown by the general formula (15),

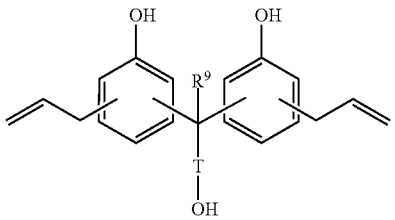

wherein T and $R^9$ have the same meanings as defined above; and a compound having two allyl groups and shown by the formula (20),

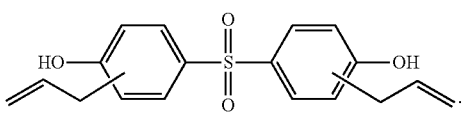

The phenol compound having two allyl groups and shown by the general formula (15) is preferably a compound shown by the general formula (16) or a compound shown by the general formula (17),

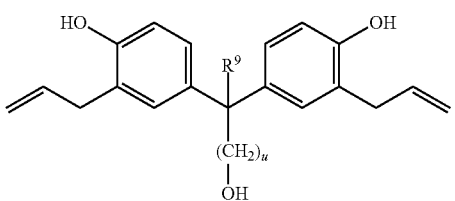

wherein $R^9$ has the same meaning as defined above, and "u" represents a positive number of 1 to 12,

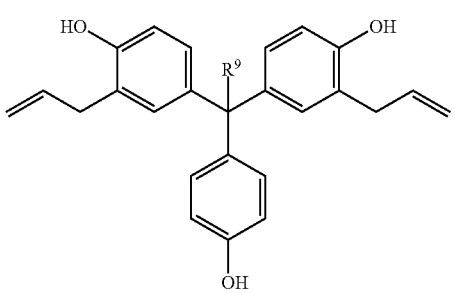

wherein $R^9$ has the same meaning as defined above.

Firstly, explanation is given about preferable conditions of the "hydrosilylation" polymerization reaction in the presence of a catalyst between the hydrogensilphenylene shown by the structural formula (10) and/or the dihydroorganosiloxane shown by the general formula (11), the phenol compound having two allyl groups as shown by the general formula (12) or (13) and/or the compound having two allyl groups and a glycidyl group as shown by the general formula (14), the phenol compound having two allyl groups as shown by the general formula (15) (preferably, the compound having two allyl groups and an alcoholic hydroxyl group as shown by the general formula (16) or the phenolic compound having two allyl groups as shown by the general formula (17)), and the compound having two allyl groups as shown by the formula (20).

Secondly, explanation is given about preferable method for synthesizing the phenol compound having two allyl groups as shown by the general formula (15), particularly, the compound having two allyl groups and an alcoholic hydroxyl group as shown by the general formula (16) or the phenol compound having two allyl groups as shown by the general formula (17).

Then, explanation is given about the reaction to introduce a carboxyl group by reacting a part or all of alcoholic or phenolic hydroxyl groups of the polymer compound that has been prepared by the hydrosilylation polymerization reaction with dicarboxylic anhydride.

First, the preferable conditions of the "hydrosilylation" polymerization reaction in the presence of a catalyst will be described.

Here, the weight average molecular weight of the polymer compound of component (A) can be easily controlled by adjusting a ratio of the total number of allyl groups in the phenol compound having two allyl groups of formula (12) or (13), the compound having two allyl groups of formula (14), the compound having two allyl groups of formula (15), and the compound having two allyl groups of formula (20) to the total number of hydrosilyl groups in the hydrogensilphenylene of formula (10) and the dihydroorganosiloxane of formula (11) (i.e., total allyl groups/total hydrosilyl groups). Alternatively, the weight average molecular weight can be easily controlled by polymerization of a specific epoxy-containing compound having two allyl groups, a specific phenol compound having two allyl groups, a specific isocyanuric-acid-skeleton-containing compound having two allyl groups, hydrogensilphenylene, and dihydroorganosiloxane while using a monoallyl compound (e.g., o-allylphenol), a monohydrosilane (e.g., triethylhydrosilane) or monohydrosiloxane as a molecular weight modifier.

Examples of the catalyst used in the polymerization reaction include platinum group metal elements such as platinum (including platinum black), rhodium, and palladium; platinum chloride, chloroplatinic acid, and chloroplatinic acid salts such as $H_2PtCl_4 \cdot xH_2O$, $H_2PtCl_6 \cdot xH_2O$, $NaHPtCl_6 \cdot xH_2O$, $KHPtCl_6 \cdot xH_2O$, $Na_2PtCl_6 \cdot xH_2O$, $K_2PtCl_4 \cdot xH_2O$, $PtCl_4 \cdot xH_2O$, $PtCl_2$, $Na_2HPtCl_4 \cdot xH_2O$, where x is preferably an integer of 0 to 6, particularly preferably 0 or 6; alcohol-modified chloroplatinic acid (U.S. Pat. No. 3,220,972); complexes of chloroplatinic acid with olefins (U.S. Pat. No. 3,159,601, U.S. Pat. No. 3,159,662, and U.S. Pat. No. 3,775,452); platinum group metals such as platinum black and palladium on supports such as alumina, silica and carbon; rhodium-olefin complexes; chlorotris(triphenylphosphine)rhodium (so-called Wilkinson's catalyst); and complexes of platinum chloride, chloroplatinic acid, or chloroplatinic acid salts with vinyl-containing siloxanes (particularly, vinyl-containing cyclic siloxanes).

The amount thereof to be used is a catalytic amount. In general, the amount is preferably 0.001 to 0.1 mass % as a platinum group metal with respect to the total amount of the reaction polymer.

In the polymerization reaction, a solvent may be used, if necessary. Preferable examples of the solvent include hydrocarbon solvents such as toluene and xylene.

With respect to polymerization conditions, the polymerization temperature is preferably in the range of 40 to 150° C., more preferably 60 to 120° C. since the catalyst is not deactivated and the polymerization can be brought to completion in a short time.

Although the polymerization time depends on the kind and the amount of a desired polymer, polymerization is preferably completed within about 0.5 to 100 hours, more preferably about 0.5 to 30 hours, in order to prevent moisture entry into the polymerization system. After completion of the polymerization, the solvent is distilled off if the solvent is used. In this way, a polymer compound having a repeating unit shown by the general formula (9) can be prepared.

In the following, the preferable method for synthesizing a bis(4-hydroxy-2-allylphenyl) derivative having an alcoholic hydroxyl group as shown by the general formula (15) or (16) will be described.

As one method for synthesizing the compound shown by the general formula (15), a compound having ketone and alcoholic hydroxyl group as shown by the following general formula (18-1) may be used as a starting material,

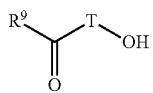
(18-1)

wherein $R^9$ and T have the same meanings as defined above.

First, the compound having ketone and alcoholic hydroxyl group as shown by the general formula (18-1) is condensed with two-equivalent phenol under acidic condition to obtain a bisphenol derivative having an alcoholic hydroxyl group as shown by the general formula (18-2),

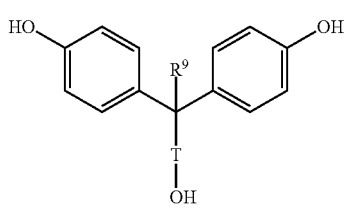
(18-2)

wherein $R^9$ and T have the same meanings as defined above.

Then, the bisphenol derivative having an alcoholic hydroxyl group as shown by the general formula (18-2) is reacted with two-equivalent halogenated allyl in a non-protic polar solvent under basic condition with potassium carbonate to obtain a compound in which hydrogen atoms of phenolic hydroxyl groups are substituted with allyl groups as shown by the general formula (18-3),

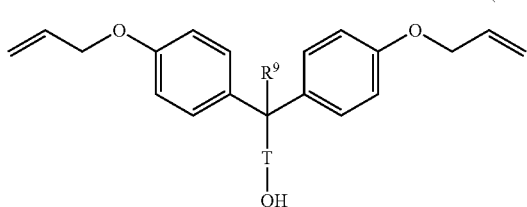
(18-3)

wherein $R^9$ and T have the same meanings as defined above.

The compound in which hydrogen atoms of phenolic hydroxyl groups are substituted with allyl groups as shown by the general formula (18-3) is then dissolved in high-boiling point solvent such as dimethylaniline and heated at a high temperature about 180° C. to initiate Claisen rearrangement reaction. This yields a desired bis(4-hydroxy-2-allylphenyl) derivative having an alcoholic hydroxyl group as shown by the general formula (15), in which the allyl group migrates to 2-position of the phenol.

As other preferable method, the compound shown by the general formula (15) can be synthesized by using a compound having ketone and carboxylic acid as shown by the general formula (18-4) as a starting material,

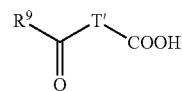
(18-4)

wherein $R^9$ has the same meaning as defined above; and T' represents a single bond or an alkylene group having 1 to 9 carbon atoms.

The compound having ketone and carboxylic acid as shown by the general formula (18-4) is condensed with two-equivalent phenol under acidic condition in the same manner as above. This yields a bisphenol derivative having carboxylic acid as shown by the general formula (18-5),

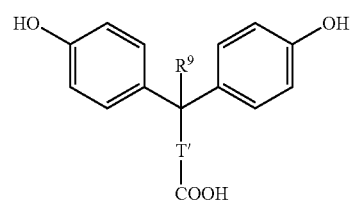
(18-5)

wherein $R^9$ and T' have the same meanings as defined above.

Further, the compound shown by the general formula (18-5) is reacted with three-equivalent halogenated allyl under the same condition as in the aforementioned method for providing allyl ether, to obtain a compound shown by the general formula (18-6). At this time, 2-equivalent halogenated allyl of the 3-equivalent halogenated allyl serves to substitute hydrogen atoms of the phenolic hydroxyl groups in the compound shown by the general formula (18-5) with allyl groups, while the other 1-equivalent halogenated allyl serves to substitute a hydrogen atom of the carboxylic acid in the compound shown by the general formula (18-5) with an allyl group. The compound shown by the general formula (18-6), a carboxylic acid allyl ester, can be thus obtained,

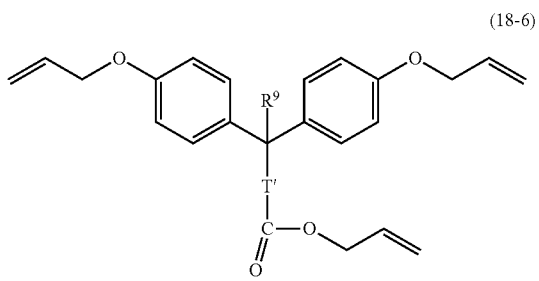

(18-6)

wherein R⁹ and T' have the same meanings as defined above.

Further, the compound shown by the general formula (18-6) is dissolved in a non-protic polar solvent such as tetrahydrofuran and toluene, and 1 or more equivalent, preferably 1 to 1.5-equivalent of a Red-Al solution is added and stirred at 0 to 30° C., preferably 0 to 15° C. to readily perform reduction reaction of the carboxylic acid portion. This yields a compound shown by the general formula (18-7) equivalent to the compound shown by the general formula (18-3),

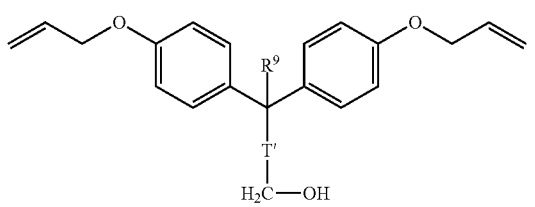

(18-7)

wherein R⁹ and T' have the same meanings as defined above.

Subsequently, the compound shown by the general formula (18-7) is subjected to Claisen rearrangement reaction in the same manner as above. This yields a derivative shown by the general formula (18-8) equivalent to a desired bis(4-hydroxy-2-allylphenyl) derivative having an alcoholic hydroxyl group as shown by the general formula (15), in which the allyl group migrates to 2-position of the phenol,

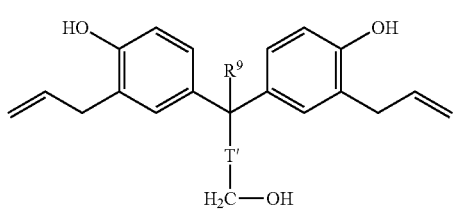

(18-8)

wherein R⁹ and T' have the same meanings as defined above.

In a series of the methods for providing the bis(4-hydroxy-2-allylphenyl) derivative having an alcoholic hydroxyl group as shown by the general formula (15), a diphenolic acid (a compound shown by the general formula (18-9)) is preferably used as the bisphenol derivative having carboxylic acid as shown by the general formula (18-5). That is, the diphenolic acid is a preferred starting material since it is industrially inexpensive and readily available.

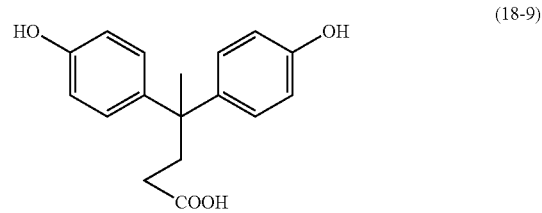

(18-9)

In the case that the diphenolic acid, which is a preferred raw material, is used, a bis(4-hydroxy-2-allylphenyl) derivative having an alcoholic hydroxyl group as shown by the formula (18-10) can be obtained, which is most preferably used for the "hydrosilylation" polymerization reaction.

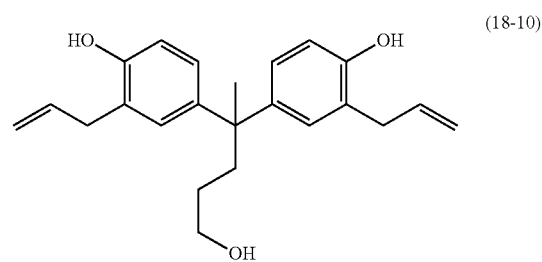 [SMILES: C=CCc1cc(C(C)(CCCO)c2ccc(O)c(CC=C)c2)ccc1O]

(18-10)

As to the phenol compound having two allyl groups as shown by the general formula (17), a compound having ketone as shown by the general formula (18-1) wherein T is a benzene ring may be similarly used as the starting material. This yields the compound having two allyl groups and a phenolic hydroxyl group as shown by the general formula (17). Preferable example of the compound shown by the general formula (18-1) used as the starting material include 4-hydroxyphthaldehyde and 4-hydroxyacetophenone. By the condensation of such starting materials with two-equivalent 2-allylphenol under acidic condition, the bis(4-hydroxy-2-allylphenyl) derivative having a phenolic hydroxyl group as shown by the general formula (17) can be obtained.

(18-1)

wherein R⁹ and T have the same meanings as defined above,

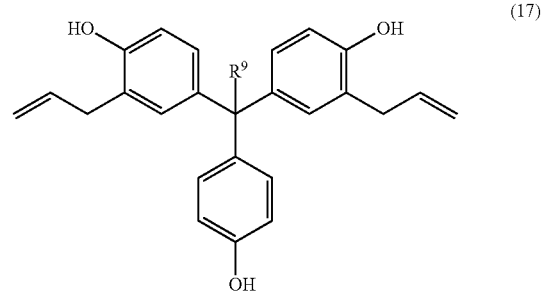

(17)

wherein R⁹ has the same meaning as defined above.

Next, explanation is given about the reaction for introducing a carboxyl group by reacting a part or all of hydroxyl groups of the polymer compound having alcoholic or phenolic hydroxyl groups that has been obtained by the hydrosilylation polymerization reaction with dicarboxylic anhydride.

Indeed, it has been considered that the polymer compound of component (A) can be obtained by the hydrosilylation using a bis(4-hydroxy-2-allylphenyl) derivative having carboxylic acid as shown by the general formula (18-11). However, when the bis(4-hydroxy-2-allylphenyl) derivative having carboxylic acid as shown by the general formula (18-11) is used, Si—H groups of the hydrogensilphenylene shown by the structural formula (10) and the dihydroorganosiloxane shown by the general formula (11) can react with the carboxylic acid during the hydrosilylation polymerization reaction, so that the desired polymer compound of component (A) cannot be obtained. Accordingly, the most preferable procedure is to prepare a polymer compound having alcoholic or phenolic hydroxyl groups as an intermediate and then introduce a carboxyl group thereto by reacting a part or all of the alcoholic or phenolic hydroxyl groups of the intermediate with dicarboxylic anhydride as described above. In this manner, the polymer compound of component (A) can be obtained.

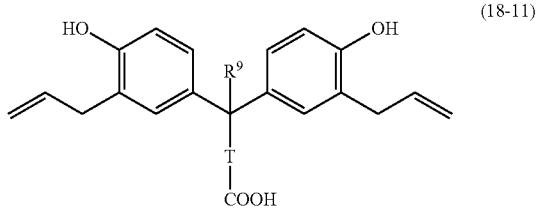

(18-11)

wherein $R^9$ and T have the same meanings as defined above.

For the reaction of a part or all of hydroxyl groups of the polymer compound having alcoholic or phenolic hydroxyl groups obtained by the hydrosilylation polymerization reaction with dicarboxylic anhydride, first, the obtained polymer compound is dissolved in a solvent having a weight 4 times as much as the polymer compound. Then, an appropriate molar equivalent of dicarboxylic anhydride is added depending on "q" and "t", which mean the mole ratio of W, i.e., the unit having alcoholic or phenolic hydroxyl groups in the general formula (9), and 1-equivalent triethylamine is added to the unit having alcoholic or phenolic hydroxyl groups. The resulting mixture is stirred at a temperature ranging from room temperature to 50° C. for several hours to initiate the reaction, whereby a carboxyl group can be introduced into the polymer compound. The equivalent of the dicarboxylic anhydride to be reacted corresponds to a ratio of repeating units of formula (1) to repeating units of formula (9), i.e., (g+h)/(q+t). For example, if the dicarboxylic anhydride to be reacted is 1-equivalent, carboxyl groups are introduced to all alcoholic hydroxyl groups of W unit in the general formula (9), which leads to the general formula (1) wherein e=0 and f=0. The introducing ratio of carboxyl groups, i.e., the preferable ranges of "g" and "h" in the general formula (1) are as described above.

The carboxylic acid thus introduced is shown by U in the general formula (1), and U is shown by the general formula (6). Furthermore, $R^{10}$ in the general formula (6) can be shown by the general formula (8),

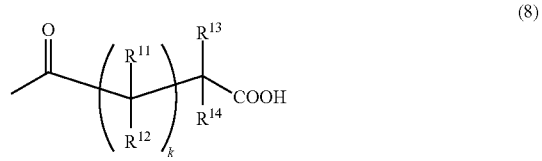

(8)

wherein the dotted line represents a bond; $R^{11}$ to $R^{14}$ are the same or different and represent a hydrogen atom, a halogen atom, a linear, branched, or cyclic alkyl group having 1 to 12 carbon atoms, or an aromatic group; $R^{11}$ and $R^{13}$ are optionally respectively bonded to $R^{12}$ and $R^{14}$ to form a substituted or unsubstituted ring structure having 1 to 12 carbon atoms; and "k" is any of 1 to 7.

The dicarboxylic anhydride to be reacted with a part or all of hydroxyl groups of the polymer compound having alcoholic or phenolic hydroxyl groups can be shown by the general formula (19),

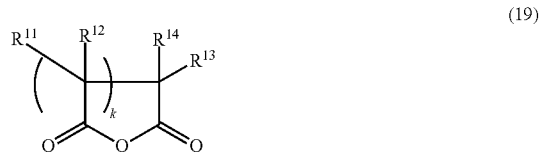

(19)

wherein $R^{11}$ to $R^{14}$ and "k" have the same meanings as defined above.

Preferable examples of the dicarboxylic anhydride include succinic anhydride, phthalic anhydride, maleic anhydride, itaconic anhydride, glutaric anhydride, adipic anhydride, pimelic anhydride, suberic anhydride, azelaic anhydride, sebacic anhydride, and compounds having the following structure.

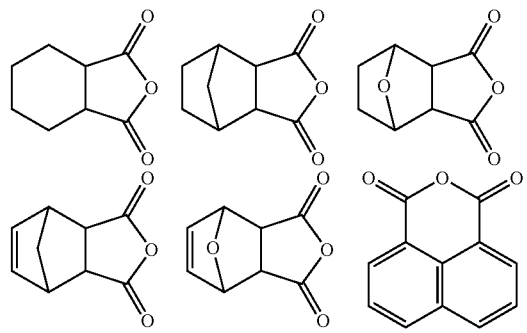

The polymer compound having the structure shown by the general formula (6) thus obtained is suitable for the base resin of the positive photosensitive resin composition, and can remedy the problem of delamination caused on a metal wiring such as Cu and Al, an electrode, and a substrate, especially on a substrate such as SiN. The reason why the delamination is improved is considered that the structural part shown by the general formula (6), which has been introduced to the polymer compound, can improve the interaction with a substrate.

On the other hand, the introduction of the structural part shown by the general formula (6) into the polymer compound can improve the solubility in an aqueous alkaline developer such as a tetramethylammonium hydroxide (TMAH) aqueous solution, which is widely used for the positive photosensitive resin composition. The positive photosensitive resin composition requires high solubility in a developer at an exposed part. That is, if the exposed part has low solubility in a developer during development of a fine pattern, undissolved residues in the pattern bottom and a footing profile between the pattern and the substrate may occur. However, when the positive photosensitive resin composition of the present invention is used to form a pattern, the solubility of the exposed part in an aqueous alkaline developer is improved, and thus the problems such as the occurrence of undissolved residues in the pattern bottom and a footing profile can be resolved, as described above.

As described above, when the polymer compound of component (A) is used as the base resin of the positive photosensitive resin composition, the solubility of the exposed part in a developer can be improved, and thus a fine pattern formation can be expected. That is, the polymer compound of component (A) is suitable for the base resins of the positive photosensitive resin composition.

<Component (B)>

Next, the photosensitive material capable of generating an acid by light and increasing a dissolution rate in an aqueous alkaline solution, which is the component (B) used in the positive photosensitive resin composition of the present invention, will be described.

The photosensitive material of component (B) may be a compound having a 1,2-naphthoquinone diazide sulfonyl group.

Examples of the 1,2-naphthoquinone diazide sulfonyl group include structures shown by the following general formula (30) or (31).

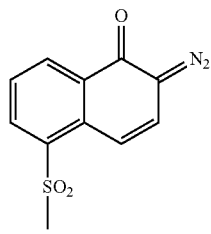

(30)

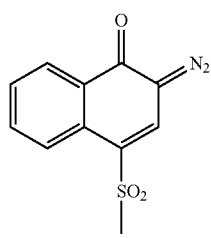

(31)

Preferable examples of a parent compound into which the 1,2-naphthoquinone diazide sulfonyl group will be introduced include trihydroxybenzophenone, tetrahydroxybenzophenone, a ballast molecule having a phenolic hydroxyl group as shown by the general formula (32), and a novolac resin having a repeating unit shown by the formula (37) and a weight average molecular weight of 2,000 to 20,000, preferably 3,000 to 10,000. That is, a compound obtained by substituting a hydrogen atom of a hydroxyl group of the following resin or compound having the phenolic hydroxyl group with a 1,2-naphthoquinone diazide sulfonyl group is preferably used as the photosensitive material of component (B).

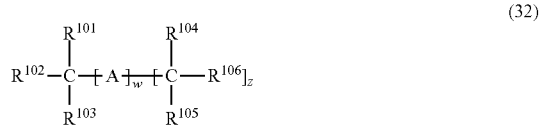

(32)

In the above formula, $R^{101}$ to $R^{106}$ independently represent a hydrogen atom, a methyl group, a group shown by the formula (33), or a group shown by the formula (34). "w" represents an integer of 0 to 2 and "z" represents an integer of 0 to 2, provided that when "z" is 0, "w" is 1 or 2. When "z" is 0 and "w" is 1, A is a hydrogen atom, a methyl group, or a group shown by the formula (33). When "z" is 0 and "w" is 2, one A is a methylene group or a group shown by the formula (35) and the other A is a hydrogen atom, a methyl group, or a group shown by the formula (33). When "z" is 1, A is a methylene group or a group shown by the formula (35). When "z" is 2 and "w" is 1, A is a methine group or a group shown by the formula (36). When "z" is 2 and "w" is 2, one A is a methylene group or a group shown by the formula (35) and the other A is a methine group or a group shown by the formula (36).

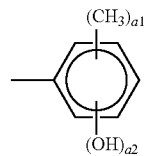

(33)

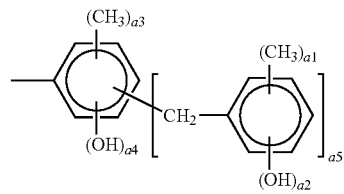

(34)

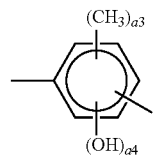

(35)

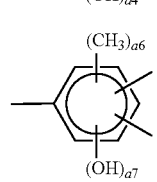

(36)

wherein a1, a2, a3, a4, a5, a6, a7 each represent an integer of 0 to 3, and a1+a2≤5, a3+a4≤4, a6+a7≤3.

In this case, the low nuclear compound (ballast molecule) shown by the formula (32) is preferably designed such that the number of benzene rings is 2 to 20, more preferably 2 to 10, much more preferably 3 to 6, and a ratio of the number of benzene rings to the number of phenolic hydroxyl groups ranges from 0.5 to 2.5, more preferably from 0.7 to 2.0, much more preferably from 0.8 to 1.5.

Examples of the low nuclear compound (ballast molecule) include the following compounds.
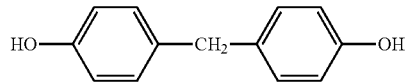 (B-1)
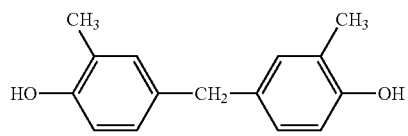 (B-2)
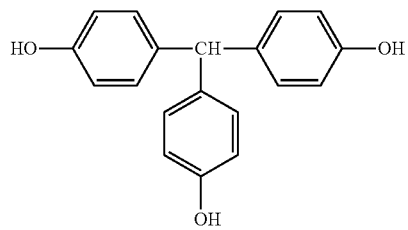 (B-3)
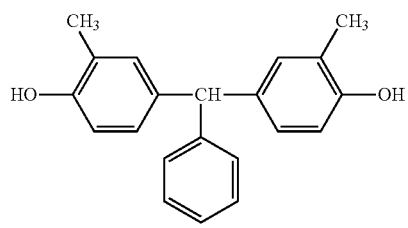 (B-4)
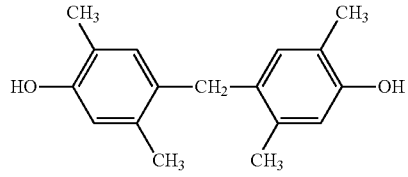 (B-5)
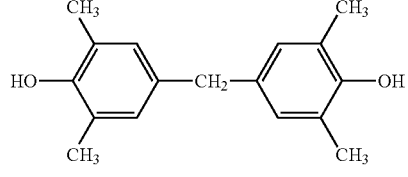 (B-6)
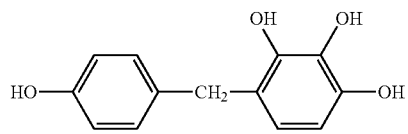 (B-7)
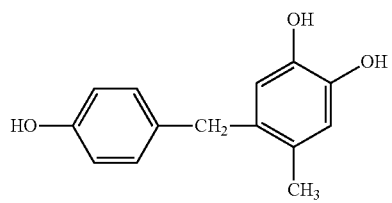 (B-8)
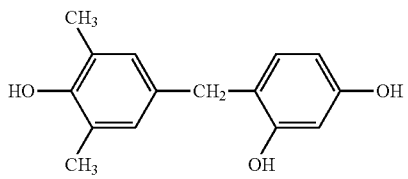 (B-9)
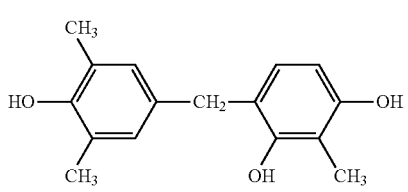 (B-10)
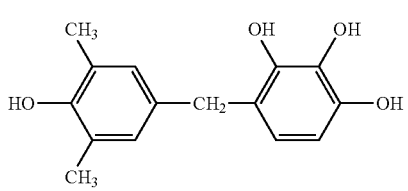 (B-11)
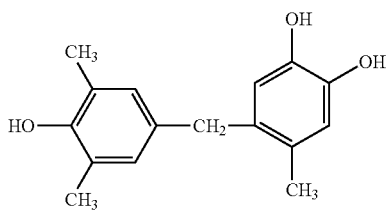 (B-12)
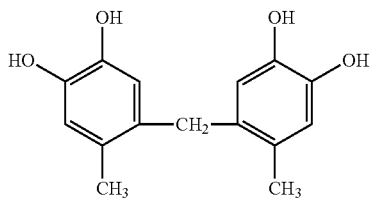 (B-13)
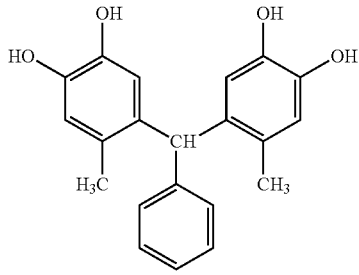 (B-14)
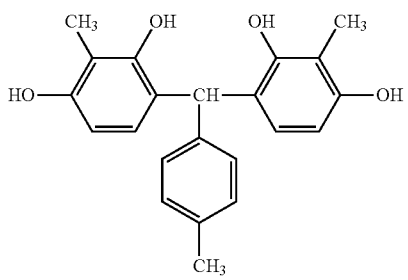 (B-15)

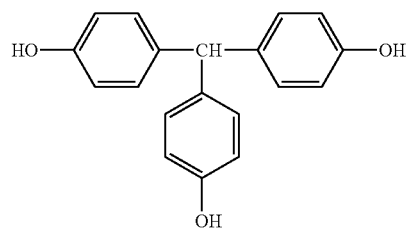
(B-16)
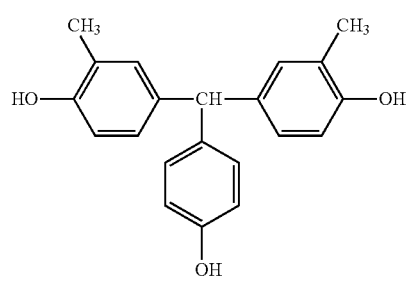
(B-17)
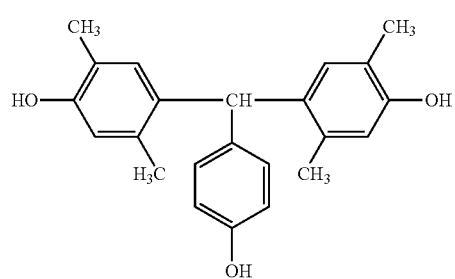
(B-18)
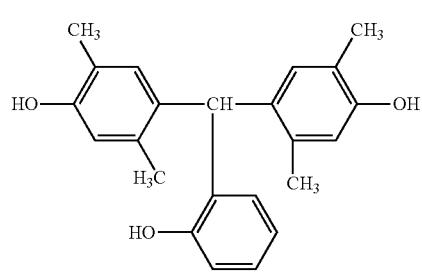
(B-19)
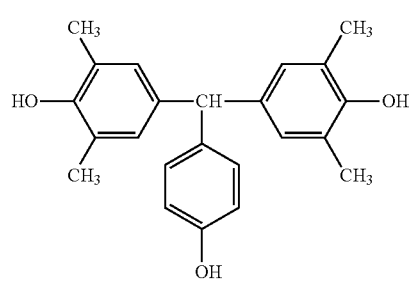
(B-20)
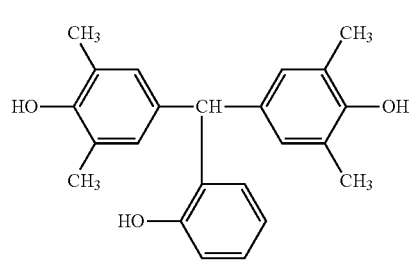
(B-21)
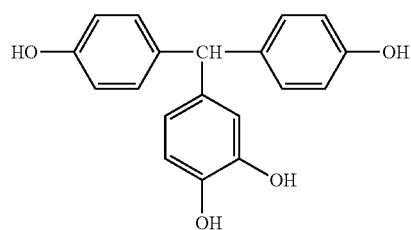
(B-22)
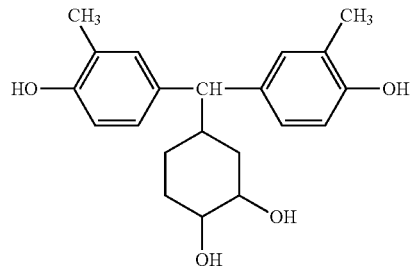
(B-23)
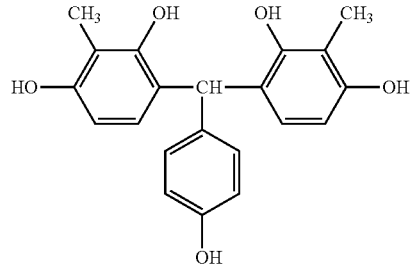
(B-24)
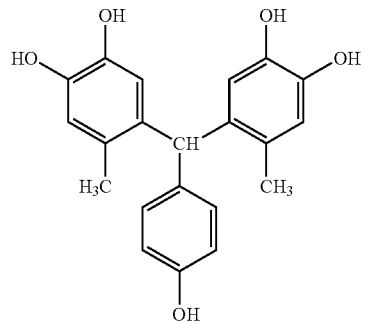
(B-25)
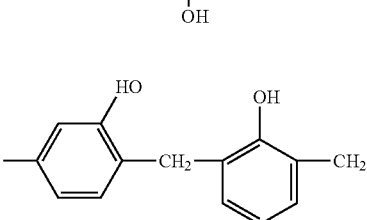
(B-26)
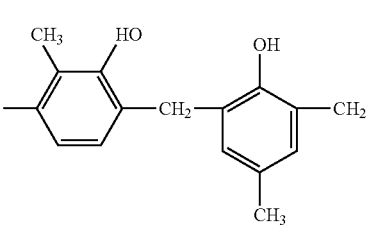
(B-27)

(B-28) 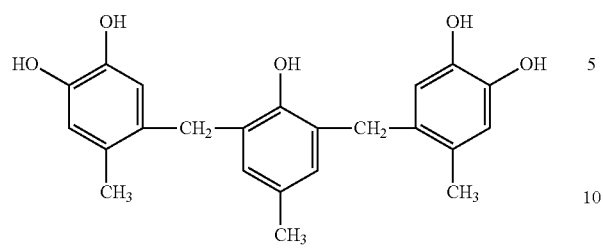
(B-29) 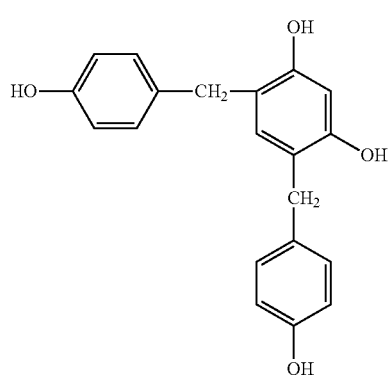
(B-30) 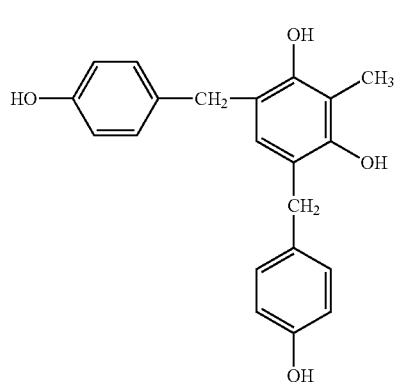
(B-31) 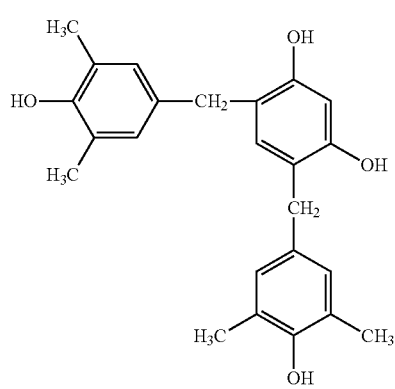
(B-32) 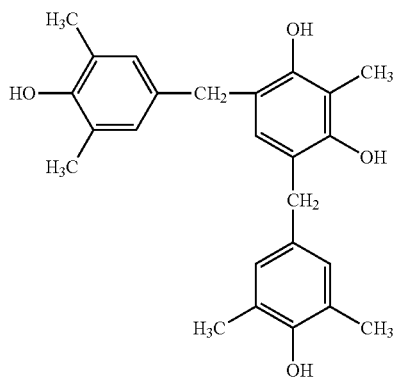
(B-33) 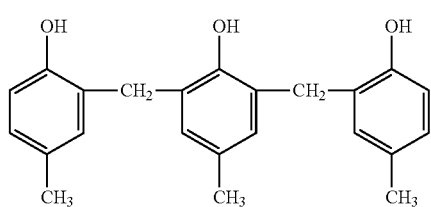
(B-34) 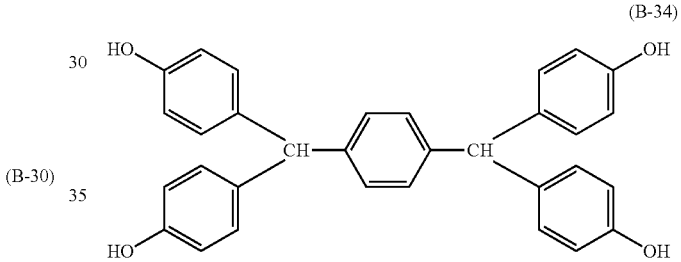
(B-35) 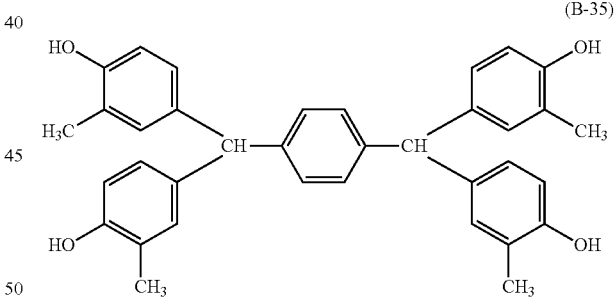
(B-36) 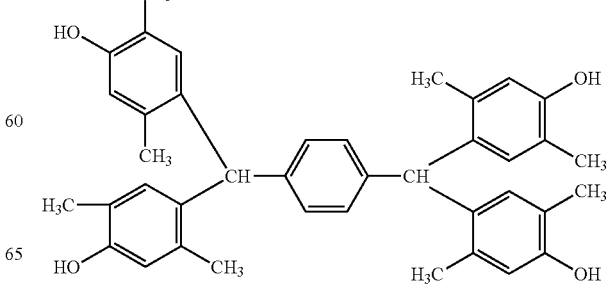

(B-37)
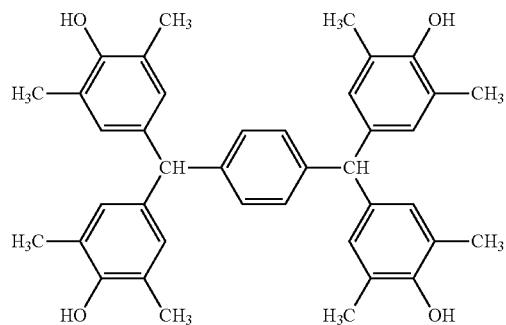

(B-38)
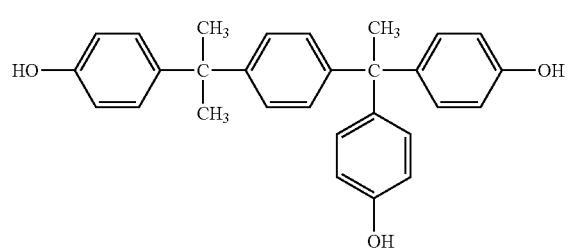

(B-39)
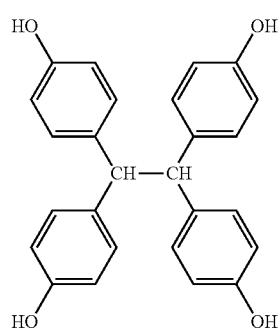

(B-40)
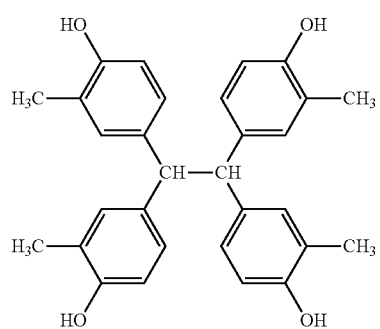

(B-41)
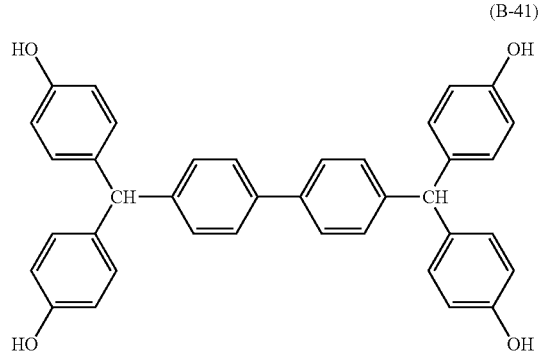

(B-42)
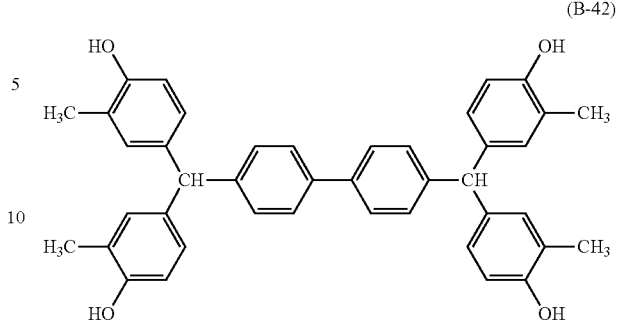

(B-43)
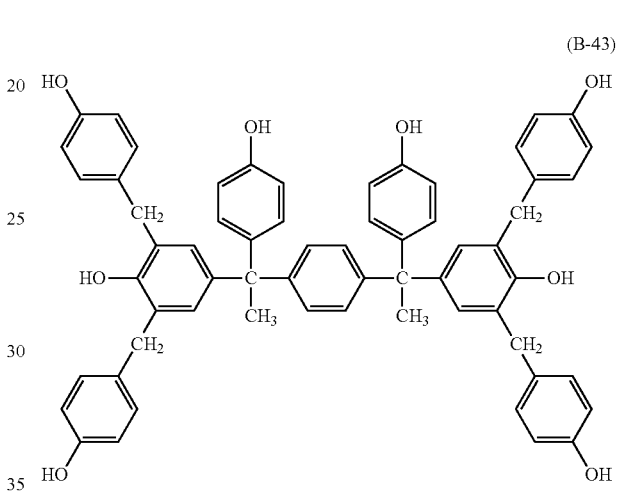

(B-44)
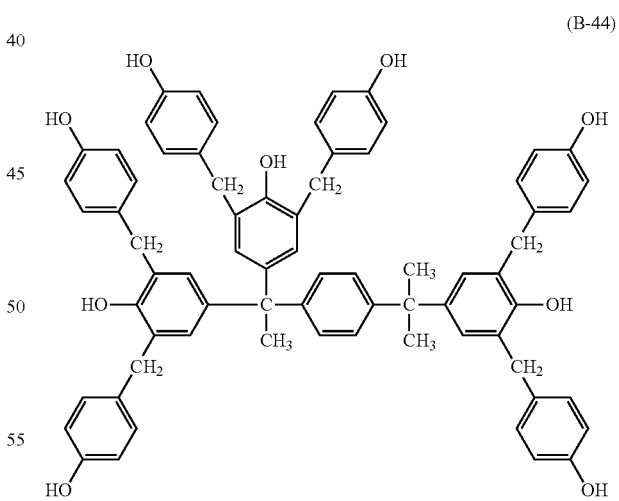

Among the low nuclear compounds (ballast molecules) shown above, (B-3), (B-29), (B-33), and (B-38) are preferable, and a compound obtained by substituting a hydrogen atom of a phenolic hydroxyl group of these ballast molecules with a 1,2-naphthoquinone diazide sulfonyl group is preferably used for the photosensitive material of component (B) in the positive photosensitive resin composition of the present invention.

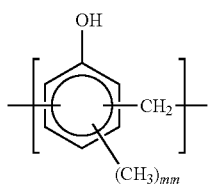

(37)

wherein mm represents an integer of 0 to 3.

The novolac resin having the repeating unit shown by the formula (37) can be synthesized by condensation of phenol shown by the formula (38), specifically, at least one phenol compound selected from o-cresol, m-cresol, p-cresol, and 3,5-xylenol, with aldehyde according to a usual method.

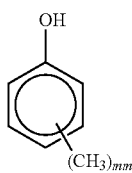

(38)

wherein mm represents an integer of 0 to 3.

Examples of the aldehyde used in this reaction include formaldehyde, paraformaldehyde, acetaldehyde, and benzaldehyde, and formaldehyde is preferable.

The mole ratio of the aldehyde to the phenol shown by the formula (38) preferably ranges from 0.2 to 2, more preferably from 0.3 to 2.

A preferable method for introducing a 1,2-naphthoquinone diazide sulfonyl group into the parent compound is dehydrochlorination condensation reaction of 1,2-naphthoquinone diazide sulfonyl chloride with phenolic hydroxyl groups in the presence of a base catalyst. In the case that the ballast molecule shown by the formula (32), trihydroxy benzophenone, or tetrahydroxy benzophenone is used, a hydrogen atom of its phenolic hydroxyl group is preferably substituted with a 1,2-naphthoquinone diazide sulfonyl group in a proportion of 10 to 100 mol %, more preferably 50 to 100 mol %. In the case that the novolac resin shown by the formula (37) is used, a hydrogen atom of its phenolic hydroxyl group is preferably substituted with 1,2-naphthoquinone diazide sulfonyl group in a proportion of 2 to 50 mol %, more preferably 3 to 27 mol %.

The adding amount of the photosensitive material of component (B) is preferably 1 to 50 parts by mass, more preferably 10 to 40 parts by mass, based on 100 parts by bass of the component (A) constituting the base resin. The photosensitive material of component (B) to be used may be one kind or a combination of two or more kinds.

When such component (B) is blended, the solubility in an aqueous alkaline solution before exposure is decreased due to the effect of dissolution inhibition by the component (B), and thus the system becomes alkali insoluble. On the other hand, once exposure is carried out, the component (B) generates an acid and increases the dissolution rate in an aqueous alkaline solution, and thus the system becomes alkali soluble.

That is, when an aqueous alkaline solution is used as a developer, an exposed part dissolves in the developer, while an unexposed part does not dissolve therein. This allows a positive pattern to be formed.

<Component (C)>

Next, the crosslinking agent, which is the component (C) used in the positive photosensitive resin composition of the present invention, will be described. The component (C) is one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group and shown by the following formula (C-2),

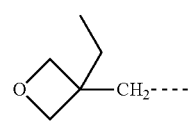

(C-1)

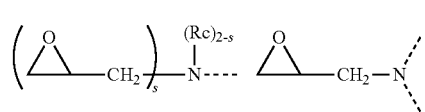

(C-2)

wherein the dotted line represents a bond; Rc represents a linear, branched, or cyclic alkyl group having 1 to 6 carbon atoms; and "s" represents 1 or 2.

Examples of the amino condensate modified with formaldehyde or formaldehyde-alcohol include melamine condensates modified with formaldehyde or formaldehyde-alcohol and urea condensates modified with formaldehyde or formaldehyde-alcohol.

The melamine condensate modified with formaldehyde or formaldehyde-alcohol can be prepared by the following procedure, for example. First, a melamine monomer is modified with formalin into a methylol form, and optionally, the resultant compound is further modified with alcohol into an alkoxy form, according to a known method, to obtain a modified melamine shown by the general formula (39). The alcohol is preferably a lower alcohol, for example, an alcohol having 1 to 4 carbon atoms.

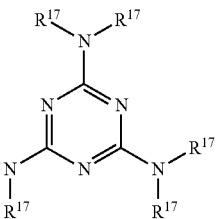

(39)

wherein each $R^{17}$ is the same or different and represents a methylol group, an alkoxymethyl group containing an alkoxy group having 1 to 4 carbon atoms, or a hydrogen atom, provided that one or more of $R^{17}$ is a methylol group or an alkoxymethyl group.

Examples of $R^{17}$ include a hydrogen atom, a methylol group, and alkoxymethyl groups such as a methoxymethyl group and an ethoxymethyl group.

Illustrative examples of the modified melamine shown by the general formula (39) include trimethoxymethyl monomethylol melamine, dimethoxymethyl monomethylol melamine, trimethylol melamine, hexamethylol melamine, and hexamethoxymethylol melamine.

Then, the modified melamine shown by the formula (39) or a multimeric compound thereof (e.g. an oligomer such as a dimer and a trimer) is polymerized by addition condensation with formaldehyde until a desired molecular weight is achieved according to a known method, to obtain the melamine condensate modified with formaldehyde or formaldehyde-alcohol.

The urea condensate modified with formaldehyde or formaldehyde-alcohol can be prepared by modifying a urea condensate having a desired molecular weight with formaldehyde into a methylol form, and optionally, further modifying the resultant compound with alcohol into an alkoxy form, according to a known method.

Illustrative examples of the urea condensate modified with formaldehyde or formaldehyde-alcohol include a methoxymethylated urea condensate, an ethoxymethylated urea condensate, and a propoxymethylated urea condensate.

These modified melamine condensates and modified urea condensates may be used solely or as a mixture of two or more kinds.

Examples of the phenol compound having on average two or more methylol groups or alkoxymethylol groups per molecule include (2-hydroxy-5-methyl)-1,3-benzenedimethanol, 2,2',6,6'-tetramethoxymethyl bisphenol A, and compounds shown by the formulae (C-3) to (C-7).

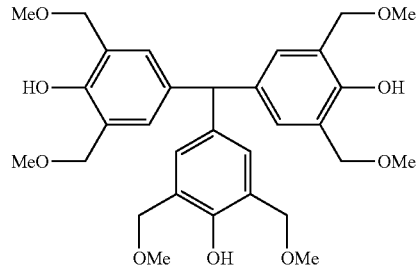

C-3

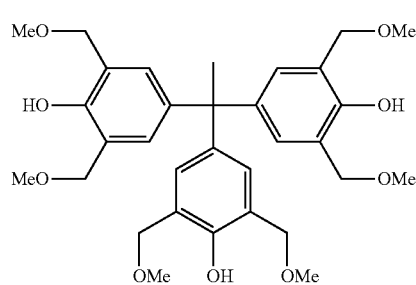

C-4

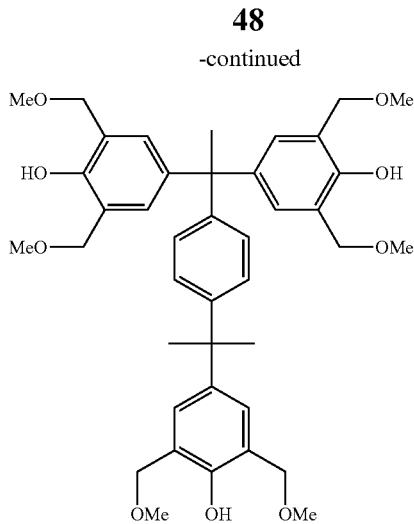

C-5

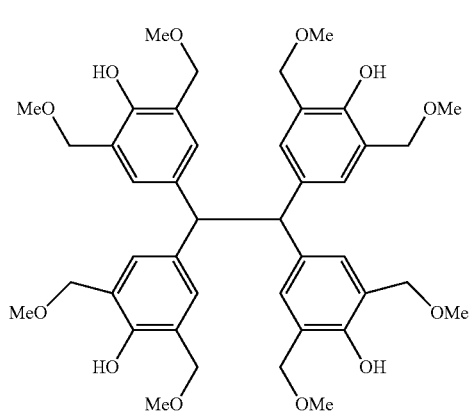

C-6

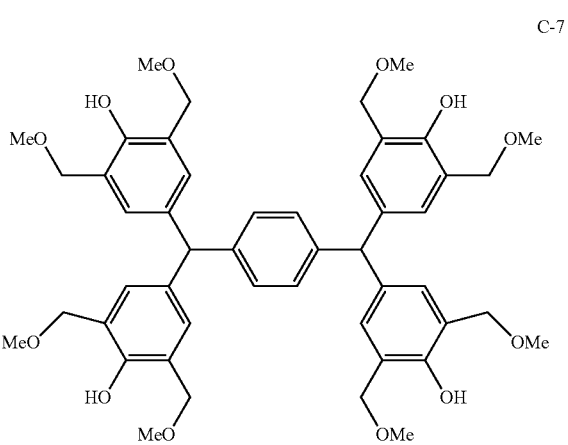 [SMILES: COCc1cc(C(c2ccc(C(c3cc(COC)c(O)c(COC)c3)c3cc(COC)c(O)c(COC)c3)cc2)c2cc(COC)c(O)c(COC)c2)cc(COC)c1O]

C-7

Examples of the polyhydric phenol compound in which a hydrogen atom of a phenolic hydroxyl group is substituted with a glycidyl group include compounds obtained by reacting a hydroxyl group of bisphenol A, tris(4-hydroxyphenyl)methane, or 1,1,1-tris(4-hydroxyphenyl)ethane with epichlorohydrin in the presence of a base catalyst. Specifically, the polyhydric phenol compound in which a hydrogen atom of a phenolic hydroxyl group is substituted with a glycidyl group is preferably, for example, a compounds shown by the formula (C-8) to (C-14).

C-8

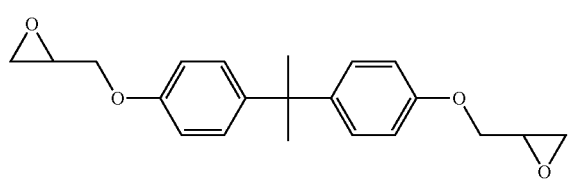

C-9

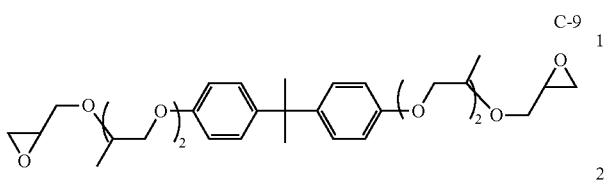

C-10

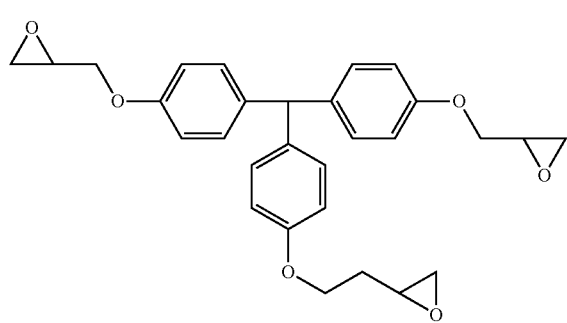

C-11

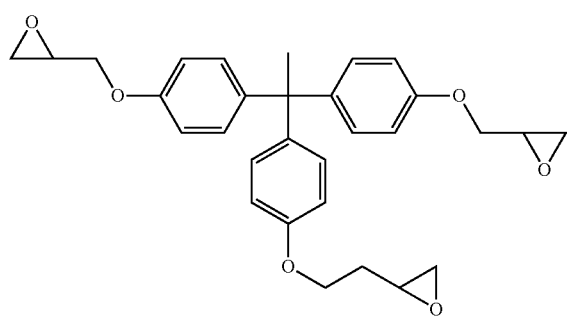

C-12

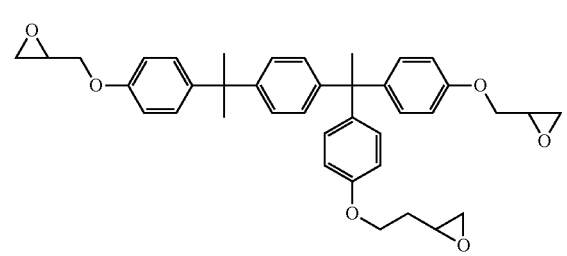

C-13

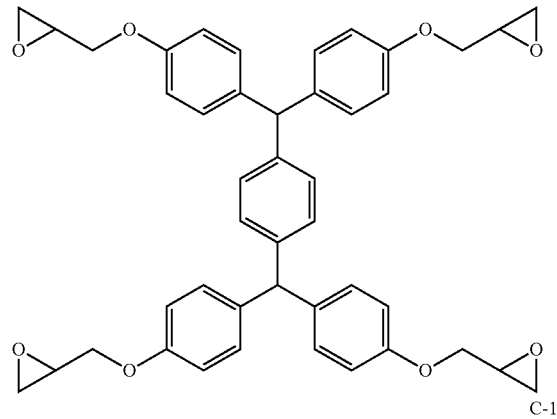

C-14

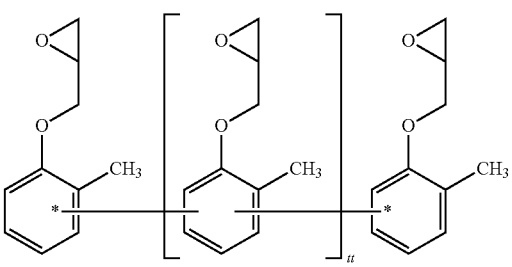

wherein 2≤tt≤3.

These polyhydric phenol compounds in which a hydrogen atom of a phenolic hydroxyl group is substituted by a glycidyl group may be used as a crosslinking agent solely or as a mixture of two or more kinds.

Examples of the polyhydric phenol compound in which a hydrogen atom of a phenolic hydroxyl group is substituted with a substituent shown by the formula (C-1) include a compound having two or more of the substituents and shown by the formula (C-15), (C-1)

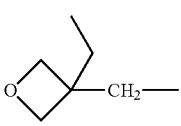

wherein the dotted line represents a bond, (C-15)

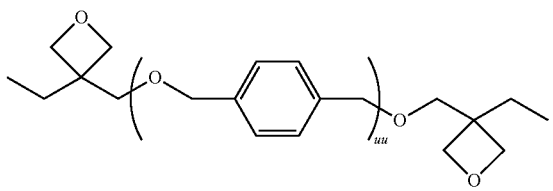

wherein 1≤uu≤3.

Examples of the compound containing two or more nitrogen atoms having a glycidyl group and shown by the formula (C-2) include compounds shown by the formula (C-16),

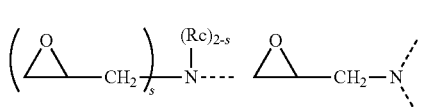
(C-2)

wherein the dotted line represents a bond; Rc represents a linear, branched, or cyclic alkyl group having 1 to 6 carbon atoms; and "s" represents 1 or 2,

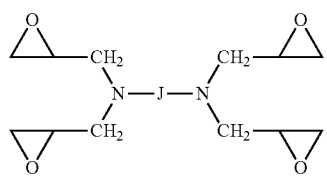
(C-16)

wherein J represents a linear, branched, or cyclic alkylene group having 2 to 12 carbon atoms or a divalent aromatic group.

Examples of the compound shown by the formula (C-16) include compounds shown by the formulae (C-17) to (C-20).

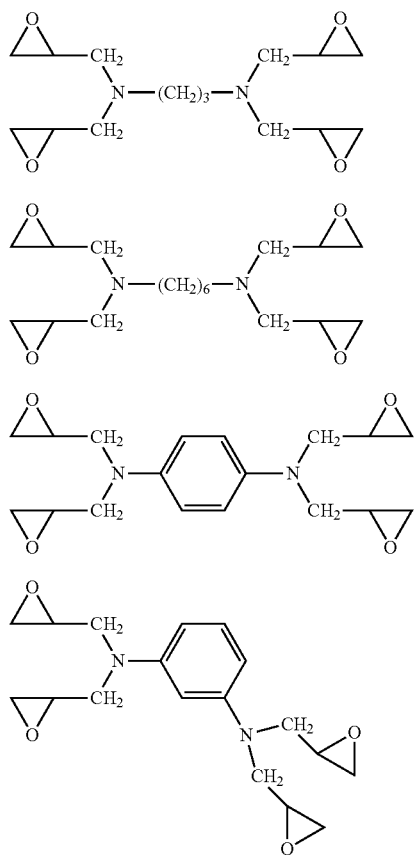

Alternatively, a compound shown by the formula (C-21) may be suitably used as the compound containing two or more nitrogen atoms having a glycidyl group and shown by the formula (C-2).

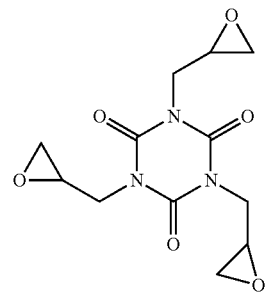
C-21

These compounds containing two or more nitrogen atoms having a glycidyl group and shown by the formula (C-2) may be used as a crosslinking agent solely or as a mixture of two or more kinds.

The above crosslinking agents serve to initiate the curing reaction with (A) the polymer compound, facilitate pattern formation, and further improve the strength of a cured product. The weight average molecular weight of the crosslinking agent is preferably 150 to 10,000, particularly preferably 200 to 3,000, in view of photo-curability and heat resistance.

The crosslinking agent to be used may be one kind or a combination of two or more kinds.

The formulation amount of the crosslinking agent is preferably 0.5 to 50 parts by mass, more preferably 1 to 30 parts by mass, based on 100 parts by mass of (A) the polymer compound, in view of photo-curability and reliability as the top coat to protect electric and electronic parts after post-curing.

<Component (D)>

As the component (D), a solvent capable of dissolving (A) the polymer compound, (B) the photosensitive material, and (C) the crosslinking agent can be used.

Illustrative examples of the solvent include ketones such as cyclohexanone, cyclopentanone, and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, and γ-butyrolactone. These solvents may be used one or more kinds. In particular, ethyl lactate, cyclohexanone, cyclopentanone, propylene glycol monomethyl ether acetate, and γ-butyrolactone, or a mixture thereof are preferred because these materials have the utmost solubility to the photosensitive material of component (B).

The formulation amount of (D) the solvent is preferably 50 to 2,000 parts by mass, more preferably 100 to 1,000 parts by mass, based on 100 parts by mass of the total amount of (A) the polymer compound, (B) the photosensitive material, and (C) the crosslinking agent, in view of compatibility, viscosity, and coating property of the positive photosensitive resin composition.

<Other Additive>

In addition to the components (A) to (D), the positive photosensitive resin composition of the present invention may contain other additives. Examples of the additives include a surfactant which is commonly used to enhance coating property.

The surfactant is preferably nonionic. Examples thereof include fluorinated surfactants, specifically, perfluoroalkyl polyoxyethylene ethanol, fluorinated alkyl ester, perfluoroalkylamine oxide, and a fluorine-containing organosiloxane compound.

The surfactant may be commercially available products, and illustrative examples thereof include Flolade "FC-4430" (available from Sumitomo 3M Ltd.), Surflon "S-141" and "S-145" (both are available from Asahi Glass Co., Ltd.), Unidyne "DS-401", "DS-4031", and "DS-451" (all are available from Daikin Industries, Ltd.), Megafac "F-8151" (available from DIC Co.), and "X-70-093" (available from Shin-Etsu Chemical Co., Ltd.). Among them, Flolade "FC-4430" (available from Sumitomo 3M Ltd.) and "X-70-093" (available from Shin-Etsu Chemical Co., Ltd.) are preferable.

The positive photosensitive resin composition of the present invention can be prepared by a usual method. After the respective components are stirred and mixed, the resulting mixture is filtered through a filter or the like to prepare the positive photosensitive resin composition. Similarly, a photo-curable dry film, which will be described later, may be prepared by using this positive photosensitive resin composition.

(Patterning Process)

The patterning using the positive photosensitive resin composition of the present invention as prepared above may be performed by a well-known lithography technology. For example, the positive photosensitive resin composition is applied by the spin coating method onto a silicon wafer, a $SiO_2$ substrate, a SiN substrate, or a substrate formed with a pattern of a copper wiring or the like, and then prebaked at 80 to 130° C. for 50 to 600 seconds approximately to form a photosensitive film having a thickness of 1 to 50 µm, preferably 1 to 30 µm, more preferably 5 to 20 µm.

The spin coating method is to dispense about 5 mL of the positive photosensitive resin composition on a silicon substrate and then rotate the substrate, thereby applying the positive photosensitive resin composition on the substrate. By adjusting the rotational speed during this operation, the thickness of the photosensitive film on the substrate can be easily controlled.

Then, a mask for forming an intended pattern is put over the photosensitive film, and the film is irradiated with a high energy beam having a wavelength of 190 to 500 nm such as i-line beam and g-line beam with an exposure dose of about 1 to 5,000 mJ/cm$^2$, preferably about 100 to 2,000 mJ/cm$^2$. Then, if necessary, post exposure baking (PEB) may be carried out on a hot plate at 60 to 150° C. for 1 to 10 minutes, preferably at 80 to 120° C. for 1 to 5 minutes.

Thereafter, development is carried out with a developer. Preferable aqueous alkaline developer for the positive photosensitive resin composition of the present invention is a 2.38% tetramethylammonium hydroxide (TMAH) aqueous solution. The development can be carried out by a usual method, for example, by soaking the substrate on which a pattern has been formed by exposure into a developer. Then, if necessary, washing, rinsing, drying, and so forth may be performed to obtain a film having an intended pattern. Meanwhile in the case that patterning is not necessary, for example, in the case that a uniform film is merely required, the same procedure may be employed as the above-mentioned patterning process except that no photomask is used.

The obtained pattern is preferably post-cured with an oven or a hot plate at 100 to 250° C., preferably 150 to 220° C., more preferably 170 to 190° C. When the post-cure temperature ranges from 100 to 250° C., the crosslinking density of the photosensitive film can be increased, and remaining volatile components can be removed. Thus, this temperature range is preferable in view of adhesiveness to a substrate, heat resistance, strength, and electronic characteristics. The time for the post-curing can be 10 minutes to 10 hours.

The cured film thus obtained has excellent flexibility, adhesiveness to a substrate, heat resistance, electric characteristics, mechanical strength, and chemical resistance to a soldering flux liquid, and a semiconductor device using this cured film as a top coat has excellent reliability, and especially, generation of cracks during a thermal cycle test can be prevented. Therefore, this cured film is useful for the top coat to protect electric and electronic parts, a semiconductor device, and the like.

[Photo-Curable Dry Film]

Furthermore, the present invention provides a photo-curable dry film produced by using the above-mentioned positive photosensitive resin composition.

First, the structure of the photo-curable dry film of the present invention will be described. The photo-curable dry film includes a supporting film, a protective film, and a photo-curable resin layer sandwiched therebetween. The photo-curable resin layer is formed from the positive photosensitive resin composition of the present invention, which is effective for forming a top coat to protect electric and electronic parts. Such a photo-curable dry film allows a fine pattern to be formed in wide ranges of film thickness and wavelength, and can be post-cured at low temperature into a cured film having excellent flexibility, heat resistance, electric characteristics, adhesiveness, reliability, and chemical resistance.

In the present invention, the photo-curable resin layer of the photo-curable dry film obtained from the positive photosensitive resin composition is solid, and the photo-curable resin layer contains no solvent. Thus, there is no fear that bubbles due to a volatile solvent remain inside the photo-curable resin layer as well as between the photo-curable resin layer and an uneven substrate. In addition, the inter-layer insulator film tends to be thinner as a semiconductor device progresses toward downsizing, thinning, and increasing layers; and the insulator film has an appropriate range of the film thickness in view of planarity and step coverage for an uneven substrate. Thus, the photo-curable resin layer preferably has a thickness of 10 to 100 µm, more preferably 10 to 70 µm, particularly preferably 10 to 50 µm in view of planarity and step coverage.

In the photo-curable resin layer, viscosity and fluidity are closely interrelated. The photo-curable resin layer can express appropriate fluidity in an appropriate range of viscosity, enabling deep penetration into a narrow space.

The photo-curable dry film of the present invention allows the photo-curable resin layer that is brought into close contact with an uneven substrate to cover the substrate in accordance with its unevenness, thereby achieving high flatness. In particular, the polymer compound of component (A), which is a main component of the photo-curable resin layer, contains a siloxane chain, and thus the surface tension thereof is so low that higher flatness can be achieved. Furthermore, when the photo-curable resin layer is brought into close contact with the substrate under a vacuum environment, generation of voids therebetween can be more effectively prevented.

Next, the method for producing the photo-curable dry film of the present invention will be described.

In the photo-curable dry film of the present invention, the positive photosensitive resin composition used for forming the photo-curable resin layer is obtained by mixing and stirring the components and filtering the mixture through a filter or the like, as described above. This positive photosensitive resin composition can be used as a material for forming the photo-curable resin layer.

The supporting film used in the photo-curable dry film of the present invention may be a monolayer or a multilayer film having multiple polymer films that are laminated. The material thereof may be a synthetic resin film such as polyethylene, polypropylene, polycarbonate, polyethylene terephthalate, etc. Among these, polyethylene terephthalate is preferable because it has appropriate flexibility, mechanical strength, and heat resistance. These films may be variously subjected to, for example, corona treatment and coating treatment with a releasing agent. For this, many commercial films may be used. Illustrative examples thereof include Cerapeel WZ (RX) and Cerapeel BX8 (R) (both are available from Toray Advanced Film Co., Ltd.), E7302 and E7304 (both are available from Toyobo Co., Ltd.), Purex G31 and Purex G71T1 (both are available from Teijin DuPont Films Japan Ltd.), and PET38×1-A3, PET38×1-V8, and PET38×1-X08 (all available from Nippa Co., Ltd.).

The protective film used in the photo-curable dry film of the present invention may be the same film as the supporting film mentioned above, but polyethylene terephthalate and polyethylene, which have appropriate flexibility, are preferable. The film may be a commercially available product, and illustrative examples thereof include, besides the polyethylene terephthalates already exemplified, polyethylene such as GF-8 (available from Tamapoly Co., Ltd.) and PE Film 0-Type (available from Nippa Co., Ltd.).

The thicknesses of the supporting film and the protective film are preferably 10 to 200 μm, particularly preferably 25 to 50 μm each, in view of stable production of the photo-curable dry film and prevention of rolling habit around a roll axis, so-called curl.

As to an apparatus for producing the photo-curable dry film, a film coater for producing an adhesive product may be generally used. Illustrative examples of the film coater include a comma coater, a comma reverse coater, a multi coater, a die coater, a lip coater, a lip reverse coater, a direct gravure coater, an offset gravure coater, a 3-roll bottom reverse coater, and a 4-roll bottom reverse coater.

The dry film can be produced as follows. A supporting film is rolled-out from a roll-out axis of a film coater, and the positive photosensitive resin composition is continuously applied onto the supporting film with a prescribed thickness to form a photo-curable resin layer while the film passes through a coater head of the film coater. This film then passes through a hot-air circulating oven at a prescribed temperature for a prescribed period. The supporting film with the photo-curable resin layer thus continuously dried thereon passes through a laminate roll together with a protective film rolled-out from another roll-out axis of the film coater under a prescribed pressure to laminate the protective film to the photo-curable resin layer on the supporting film, and then the resultant film is rolled-up by a roll-up axis of the film coater. In this operation, the temperature of the hot-air circulating oven preferably ranges from 25 to 150° C., the period for passing through preferably ranges from 1 to 100 minutes, and the laminate roll pressure preferably ranges from 0.01 to 5 MPa.

Then, the patterning process using the photo-curable dry film of the present invention will be described.

In the patterning process using the photo-curable dry film of the present invention, first, the protective film is separated from the photo-curable dry film to bring the photo-curable resin layer thereby uncovered into close contact with a substrate. Then, exposure is performed, followed by post exposure baking (hereinafter, PEB). Subsequently, development is performed, and if necessary, post-curing is carried out to obtain a cured film with a pattern.

First, the photo-curable dry film is brought into close contact with a substrate by a film-bonding apparatus. Examples of the substrate include a silicon wafer, a silicon wafer for TSV, a circuit substrate made of plastics, ceramics, various metals, etc., and especially, a substrate including a trench and/or a hole having an aperture width of 10 to 100 μm and a depth of 10 to 120 μm. The film-bonding apparatus is preferably a vacuum laminator.

More specifically, the photo-curable dry film is attached to the film-bonding apparatus, and the protective film of the photo-curable dry film is separated therefrom. The photo-curable resin layer thereby uncovered is brought into close contact with the substrate on a table at a prescribed temperature by an adhering roll under a prescribed pressure in a vacuum chamber with a prescribed degree of vacuum. The temperature of the table is preferably 60 to 120° C. The pressure of the adhering roll is preferably 0 to 5.0 MPa. The degree of vacuum of the vacuum chamber is preferably 50 to 500 Pa.

After the close contact, patterning may be performed by a well-known lithography technology. At this time, if necessary, pre-baking may be performed in order to effectively progress the photo-curing reaction of the photo-curable resin layer and to improve adhesiveness between the photo-curable resin layer and the substrate. The pre-baking may be performed, for example, at 40 to 140° C. for 1 minute to 1 hour approximately.

Then, the photo-curable resin layer is cured by exposure to a light having a wavelength of 190 to 500 nm via a photomask either through the supporting film or after removing the supporting film. The photomask may be obtained by engraving a prescribed pattern. The photomask is preferably made of a material that can block the light having a wavelength of 190 to 500 nm. For example, a material such as chromium is preferably used, although not limited thereto.

Examples of the light having a wavelength of 190 to 500 nm include light having various wavelengths generated from, for example, a radiation-generating apparatus, including ultraviolet rays such as g-line beam and i-line beam and far ultraviolet rays (248 nm and 193 nm). The wavelength preferably ranges from 248 to 436 nm. The exposure dose is preferably, for example, in the range of 10 to 3,000 mJ/cm$^2$.

Then, post exposure baking (PEB) is carried out to enhance the development sensitivity. The post exposure baking may be performed, for example, at 40 to 140° C. for 0.5 to 10 minutes.

Thereafter, development is performed with a developer. Preferable aqueous alkaline developer for the positive photosensitive resin composition of the present invention is a 2.38% tetramethylammonium hydroxide (TMAH) aqueous solution. The development can be carried out by a usual method, for example, by soaking the substrate on which a pattern has been formed by exposure into a developer. Then, if necessary, washing, rinsing, drying, and so forth may be performed to obtain a film of the photo-curable resin layer having an intended pattern. Meanwhile in the case that patterning is not necessary, for example, in the case that a uniform film is merely required, the same procedure may be employed as the above-mentioned patterning process except that no photomask is used.

The obtained pattern is preferably post-cured with an oven or a hot plate at 100 to 250° C., preferably 150 to 220° C., more preferably 170 to 190° C. When the post-cure temperature ranges from 100 to 250° C., the crosslinking density of the film of the photo-curable resin layer can be increased, and remaining volatile components can be removed. Thus, this temperature range is preferable in view of adhesiveness to a substrate, heat resistance, strength, and electronic characteristics. The time for the post-curing can be 10 minutes to 10 hours.

The cured film thus obtained has excellent flexibility, adhesiveness to a substrate, heat resistance, electric characteristics, mechanical strength, and chemical resistance to a soldering flux liquid, and a semiconductor device using this cured film as a top coat has excellent reliability, and especially, generation of cracks during a thermal cycle test can be prevented. Therefore, this cured film can be used as the top coat to protect electric and electronic parts, a semiconductor device, and the like.

As described above, the photo-curable dry film of the present invention can be effectively used for the substrate including a trench and/or a hole. Thus, the present invention provides a laminate comprising a substrate including a trench and/or a hole each having an aperture width of 10 to 100 μm and a depth of 10 to 120 μm, and a cured layer of the photo-curable resin formed by the photo-curable dry film laminated on the substrate.

Furthermore, the present invention provides a top coat to protect electric and electronic parts, formed of a cured film obtained by the above-mentioned patterning process.

Furthermore, the present invention provides a substrate that is protected by a film obtained by curing a pattern formed by the above-mentioned patterning process.

This substrate is protected by a cured film excellent in flexibility, adhesiveness, heat resistance, electric characteristics, mechanical strength, chemical resistance, reliability, and crack resistance.

EXAMPLES

Hereinafter, the present invention will be specifically described with reference to Synthesis Examples and Examples, but the present invention is not limited to the following examples. Meanwhile, the term "parts" indicates parts by mass in the following examples.

I. Preparation of Positive Photosensitive Resin Composition

The structures of compounds (M-1) to (M-13) used in Synthesis Examples are shown below.

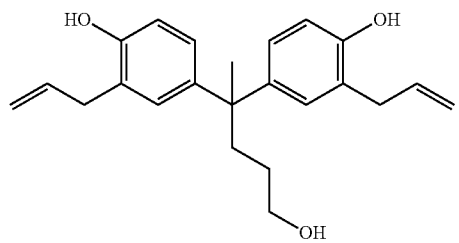
(M-1)

-continued

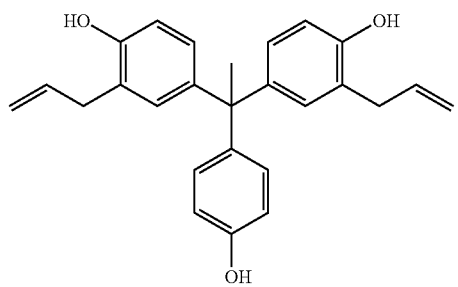
(M-2)

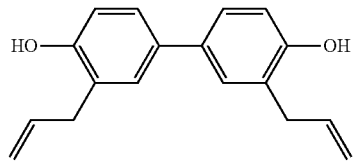
(M-3)

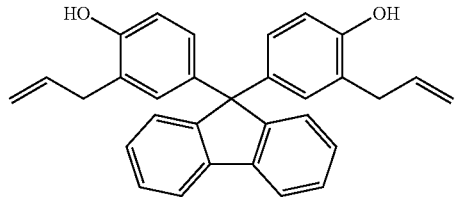
(M-4)

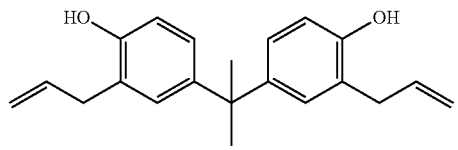
(M-5)

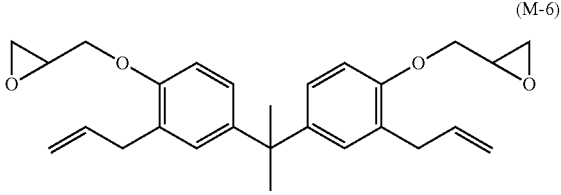
(M-6)

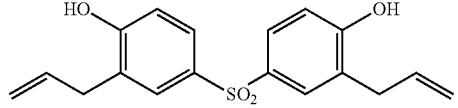
(M-7)

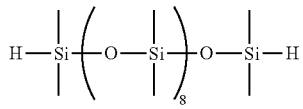
(M-8)

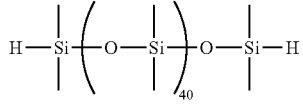
(M-9)

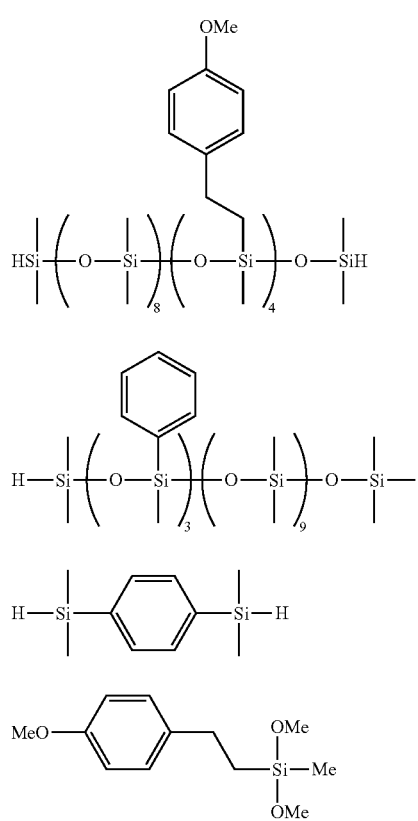
(M-10)

(M-11)

(M-12)

(M-13)

The component (A), the polymer compound having a repeating unit shown by the general formula (1) used in the positive photosensitive resin composition of the present invention is shown below.

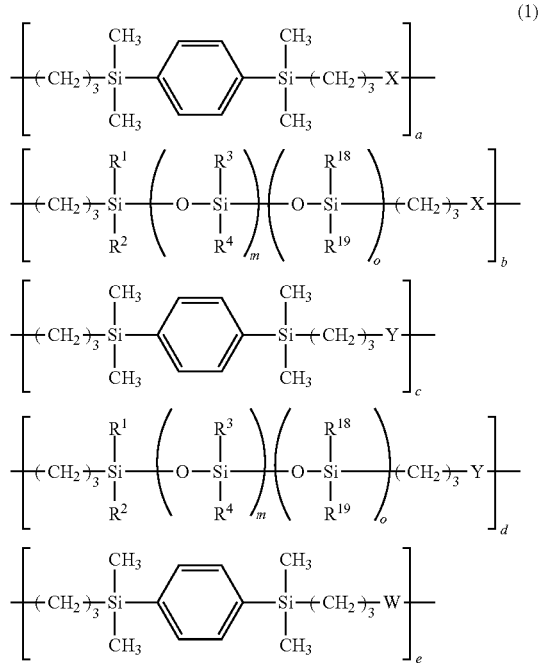

wherein $R^1$ to $R^4$, $R^{18}$, $R^{19}$, "a", "b", "c", "d", "e", "f", "g", "h", "i", "j", "m", "o", X, Y, W, U, and S have the same meanings as defined above.

[Synthesis Example 1] Synthesis of 4,4'-bis(4-hydroxy-3-allylphenyl)pentanol (M-1)

A 5-L flask equipped with a stirrer, thermometer, and nitrogen purge system was charged with 458 g of diphenolic acid, 884 g of potassium carbonate, and 2,000 g of dimethylacetamide. Then, 774 g of allylbromide was added dropwise thereto while stirring the mixture at room temperature under nitrogen atmosphere, followed by further stirring at 60° C. for 58 hours. To the resulting mixture was added dropwise 221 g of potassium carbonate, 193 g of allylbromide, and 500 g of dimethylacetamide while maintaining the temperature, and the mixture was further stirred at 60° C. for 20 hours. After 2,000 g of water was added dropwise under ice-cooling to terminate the reaction, 1,000 g of toluene, 1,000 g of hexane, and 2,000 g of water were added, and the organic layer was collected. The obtained organic layer was successively washed with 2,000 g of water, 500 g of water four times, and 500 g of saturated saline, and the solvent was distilled off to obtain 686 g of a crude material of allyl 4,4'-bis(4-allyloxyphenyl)pentanoate.

A 5-L flask equipped with a stirrer, thermometer, and nitrogen purge system under nitrogen atmosphere was charged with 655 g of the allyl 4,4'-bis(4-allyloxy-phenyl) pentanoate and 1,310 g of tetrahydrofuran to make a solution. Then, 605 g of sodium bis(2-methoxyethoxy)aluminum hydride (70 mass % toluene solution) was added dropwise thereto under ice-cooling. After stirring the mixture at room temperature for 3 hours, 1,526 g of 10 mass % hydrochloric acid was added dropwise under ice-cooling to terminate the reaction. To the reaction solution was added 250 g of ethyl acetate and 750 g of toluene, and the organic layer was collected and washed with 500 g of water 3 times. The solvent of the obtained organic layer was distilled off, and a remainder was dissolved in 1,000 g of toluene, and washed with 300 g of 4 mass % sodium hydroxide aqueous solution 5 times, 330 g of 2 mass % hydrochloric acid and 300 g of water 4 times. Thereafter, the solvent of the obtained organic layer was distilled off to obtain 555 g of a crude material of 4,4'-bis(4-allyloxyphenyl)pentanol.

Then, a 5-L flask equipped with a stirrer, thermometer, and nitrogen purge system under nitrogen atmosphere was charged with 500 g of the 4,4'-bis(4-allyloxyphenyl)pentanol and 500 g of N,N-diethylaniline to make a solution, and the solution was heated at 180° C. and stirred for 18 hours. After cooling the solution to room temperature, 1,460 g of 10 mass % hydrochloric acid was added dropwise under ice-cooling, and 2,400 g of ethyl acetate was added to the reaction mixture. Then, the organic layer was collected and washed with 2,400 g of water 4 times. The solvent of the obtained organic layer was distilled off, and a remainder was dissolved in 500 g of ethyl acetate, and 2,000 g of hexane was added dropwise thereto under stirring. Thereafter, the hexane layer was removed, and the remaining oily material was dissolved in 500 g of ethyl acetate and collected. Then, the solvent of the obtained organic layer was distilled off to obtain 466 g of 4,4'-bis(4-hydroxy-3-allylphenyl)pentanol (M-1) with a yield of 93%. The compound (M-1) was identified by $^1$H-NMR (600 MHz) (JEOL-600 spectrometer manufactured by JEOL, Ltd.).

[Synthesis Example 2] Synthesis of bis(4-hydroxy-3-allylphenyl)-(4-hydroxyphenyl)-methane (M-2)

A 3-necked 1-L flask inside which was replaced with nitrogen was charged with 50.0 g (409 mmol) of 4-hydroxybenzaldehyde and 330.0 g (2,457 mmol) of 2-allylphenol. The mixture was stirred at room temperature to dissolve the 4-hydroxybenzaldehyde, and transferred to an ice bath. Then, 7.9 g of methanesulfonic acid was added dropwise slowly while maintaining the reaction solution at 10° C. or lower. After dropwise addition, the reaction solution was aged for 10 hours at room temperature, and 400 g of toluene and 400 g of saturated sodium hydrogen carbonate in aqueous solution were added thereto, and this mixture was transferred to a 2-L separatory funnel. The aqueous layer was removed therefrom, and 400 g of saturated sodium hydrogen carbonate in aqueous solution was added thereto for liquid separation followed by water-washing with 400 g of ultrapure water twice. After the collected organic layer was crystallized by 4,400 g of hexane, supernatant was removed, and a remainder was dissolved in 300 g of toluene to crystallize it again by 2,000 g of hexane. This procedure was repeated once again, and the precipitated crystal was collected by filtration and dried to obtain 95 g of bis(4-hydroxy-3-allylphenyl)-(4-hydroxyphenyl)-methane (M-2) with a yield of 58%. The compound (M-2) was identified by $^1$H-NMR (600 MHz) (JEOL-600 spectrometer manufactured by JEOL, Ltd.).

[Synthesis Example 3] Synthesis of 3,3'-diallyl-4,4'-dihydroxy-1,1'-biphenyl (M-3)

A 4-necked 3-L flask equipped with a stirrer, thermometer, and nitrogen purge system was charged with 300 g of 4,4'-biphenol, 534 g of potassium carbonate, and 1,200 g of acetone. Then, 468 g of allylbromide was added dropwise thereto while stirring the mixture at room temperature under nitrogen atmosphere, followed by further stirring at 50° C. for 24 hours. After cooling the mixture to room temperature, 1,200 g of water was added to terminate the reaction, and the precipitated crystal was collected by filtration. Further, the obtained crystal was washed with 1,200 g of water 3 times, and the solvent was then distilled off to obtain 429 g of a crude material of 4,4'-bis(allyloxy)-1,1'-biphenyl.

Then, a 3-L flask equipped with a stirrer, thermometer, and nitrogen purge system under nitrogen atmosphere was charged with 429 g of the 4,4'-bis(allyloxy)-1,1'-biphenyl and 858 g of N,N-diethylaniline to make a solution, and the solution was heated at 180° C. and stirred for 24 hours. After cooling the solution to room temperature, 2,300 g of 10 mass % hydrochloric acid was added dropwise under ice-cooling, and 1,500 g of ethyl acetate was added to the reaction mixture. Then, the organic layer was collected and washed with 1,500 g of water 5 times. The solvent of the obtained organic layer was distilled off, and 93 g of ethyl acetate and 2,800 g of hexane were added thereto. The resulting solution was stirred at room temperature for a while to precipitate a crystal, and the crystal was collected by filtration. Thereafter, the crystal was washed with 1,000 g of hexane twice to obtain 370 g of 3,3'-diallyl-4,4'-dihydroxy-1,1'-biphenyl (M-3) with a two-step yield of 86%. The compound (M-3) was identified by $^1$H-NMR (600 MHz) (JEOL-600 spectrometer manufactured by JEOL, Ltd.).

[Synthesis Example 4] Synthesis of Compound (M-13)

A 3-necked 1-L flask equipped with a stirrer, thermometer, and nitrogen purge system was charged with 348 g (3.28 mol) of dimethoxymethylsilane and 2.1 g of toluene solution containing chloroplatinic acid (5 mass %) and heated at 60° C. Then, 400 g (2.98 mol) of 4-methoxystyrene was added dropwise thereto over 7 hours. At this time, the heating temperature was increased to 100° C. with the increase of the reaction system temperature. After dropwise addition, the mixture was cooled to room temperature and purified by distillation to obtain 583 g of compound (M-13) with a yield of 81.4%. The compound (M-13) was identified by $^1$H-NMR (600 MHz) (JEOL-600 spectrometer manufactured by JEOL, Ltd.).

[Synthesis Example 5] Synthesis of Compound (M-10)

A 3-necked 1-L flask was charged with 212 g of the compound (M-13), and 162 g of 7.5 mass % aqueous potassium hydroxide solution was added thereto under stirring at room temperature. After addition, the mixture was heated at 100° C. while removing generated methanol from the system and aged for 6 hours. Then, the mixture was cooled to room temperature, and 200 g of toluene and 68 g of 10 mass % hydrochloric acid were added. This mixture was transferred to a 1-L separatory funnel, and the lower aqueous layer was removed. Further, liquid separation and water-washing operation was repeated 3 times with 50 g of ultrapure water, and the organic layer was concentrated under reduced pressure to obtain 166 g of hydrolysis condensate of the compound (M-13).

A 3-necked 1-L flask inside which was replaced with nitrogen was charged with 164 g of the obtained hydrolysis condensate (0.84 mol when assuming that one condensation unit corresponds to its molecular weight), 125 g of cyclic tetramer of dimethylsiloxane (1.69 mol when assuming that one condensation unit corresponds to its molecular weight), and 37.4 g (0.28 mol) of 1,1,3,3-tetramethyldisiloxane, and the mixture was stirred at room temperature. Then, 1.5 g of trifluoromethanesulfonic acid was added dropwise thereto under stirring. After dropwise addition, the mixture was heated at 60° C. and aged for 3 hours. The mixture was then cooled to room temperature, and 300 g of toluene and 208 g of 4 mass % aqueous sodium hydrogencarbonate solution were added thereto, followed by stirring for 1 hour. This mixture was transferred to a 1-L reparatory funnel, and the lower aqueous layer was removed. Further, liquid separation and water-washing operation was repeated twice with 200 g of ultrapure water, and the organic layer was concentrated under reduced pressure to obtain compound (M-10). The compound (M-10) was identified by $^1$H-NMR (600 MHz) (JEOL-600 spectrometer manufactured by JEOL, Ltd.).

[Synthesis Example 6] Synthesis of Polymer Compound (A-1)

A 3-L flask equipped with a stirrer, thermometer, nitrogen purge system, and reflux condenser was charged with 350 g of toluene and 120 g of compound (M-1) to make a solution. To the solution were added 39 g of compound (M-3) and 85 g of compound (M-8), and the resulting mixture was heated at 60° C. Thereafter, 1.1 g of carbon carried platinum catalyst (5 mass %) was added thereto, and the mixture was heated at 90° C. and aged for 3 hours. Then, the mixture was cooled to 60° C., 1.1 g of carbon carried platinum catalyst (5 mass %) was added again, and 62 g of compound (M-12) was added dropwise into the flask over 30 minutes. At this time, the temperature inside the flask was increased to 65 to 67° C. After dropwise addition, the mixture was further aged at 90° C. for 3 hours and cooled to room temperature. Then, 780 g of methyl isobutyl ketone was added to the reaction solution, and this reaction solution was filtered under pressure through a filter to remove the platinum catalyst. Further, 780 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 750 g of tetrahydrofuran was added thereto, and the tetrahydrofuran solution was concentrated under reduced pressure so as to have a solid concentration of 30 mass %.

Then, a 3-L flask equipped with a stirrer, thermometer, nitrogen purge system, and reflux condenser was charged with 1,000 g of the tetrahydrofuran solution containing 30 mass % of the polymer compound; and 31 g of succinic anhydride and 32 g of triethylamine were added thereto, and the mixture was heated at 50° C. After stirring for 2 hours, the mixture was cooled to room temperature, and 900 g of saturated aqueous ammonium chloride solution and 1,500 g of ethyl acetate were added to terminate the reaction. Then, the aqueous layer was removed, and liquid separation and water-washing operation was repeated 5 times with 900 g of ultrapure water. The solvent of the collected organic layer was distilled off, and 600 g of cyclopentanone was added thereto. The resulting cyclopentanone solution was then concentrated under reduced pressure so as to have a solid concentration of 40 to 50 mass %, yielding a solution containing polymer compound (A-1) having carboxylic acid and cyclopentanone as the main solvent. The molecular weight of the polymer compound in this solution was measured by GPC, consequently finding a weight average molecular weight of 10,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

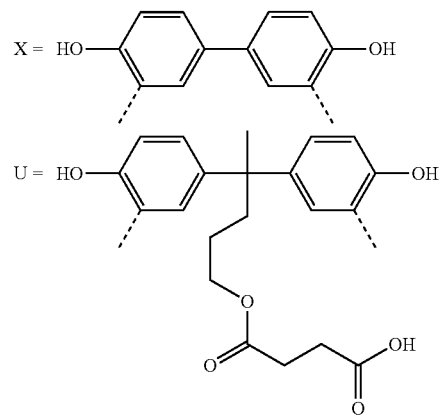

[Synthesis Example 7] Synthesis of Polymer Compound (A-2)

A 3-L flask equipped with a stirrer, thermometer, nitrogen purge system, and reflux condenser was charged with 497 g of toluene and 120 g of compound (M-1) to make a solution. To the solution were added 91 g of compound (M-3) and 119 g of compound (M-8), and the resulting mixture was heated at 60° C. Thereafter, 1.6 g of carbon carried platinum catalyst (5 mass %) was added thereto, and the mixture was heated at 90° C. and aged for 3 hours. Then, the mixture was cooled to 60° C., 1.6 g of carbon carried platinum catalyst (5 mass %) was added again, and 87 g of compound (M-12) was added dropwise into the flask over 30 minutes. At this time, the temperature inside the flask was increased to 65 to 67° C. After dropwise addition, the mixture was further aged at 90° C. for 3 hours and cooled to room temperature. Then, 780 g of methyl isobutyl ketone was added to the reaction solution, and this reaction solution was filtered under pressure through a filter to remove the platinum catalyst. Further, 780 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 1,078 g of tetrahydrofuran was added thereto, and the tetrahydrofuran solution was then concentrated under reduced pressure so as to have a solid concentration of 30 mass %.

Then, a 3-L flask equipped with a stirrer, thermometer, nitrogen purge system, and reflux condenser was charged with 1,400 g of the tetrahydrofuran solution containing 30 mass % of the polymer compound; and 31 g of succinic anhydride and 32 g of triethylamine were added thereto, and the mixture was heated at 50° C. After stirring for 2 hours, the mixture was cooled to room temperature, and 900 g of saturated aqueous ammonium chloride solution and 1,500 g of ethyl acetate were added to terminate the reaction. Then, the aqueous layer was removed, and liquid separation and water-washing operation was repeated 5 times with 900 g of ultrapure water. The solvent of the collected organic layer was distilled off, and 600 g of cyclopentanone was added thereto. The resulting cyclopentanone solution was then concentrated under reduced pressure so as to have a solid concentration of 40 to 50 mass %, yielding a solution containing polymer compound (A-2) having carboxylic acid and cyclopentanone as the main solvent. The molecular weight of the polymer compound in this solution was measured by GPC, consequently finding a weight average molecular weight of 13,000 in terms of polystyrene. The polymer compound corresponds to the general formula (1) wherein a=0.367, b=0.133, c=0, d=0, e=0, f=0, g=0.367, h=0.133, i=0, j=0, and X and U are as follows.

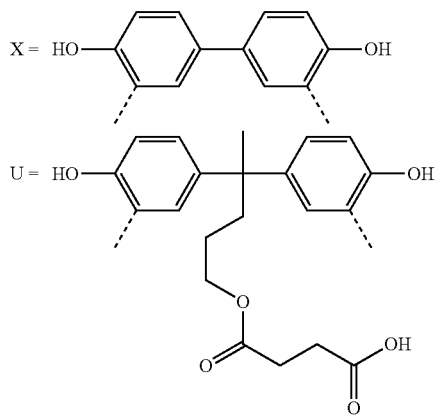

[Synthesis Example 8] Synthesis of Polymer Compound (A-3)

A polymer compound was synthesized in the same manner as in Synthesis Example 6 except that 362 g of compound (M-9) was used in place of 85 g of compound (M-8), and cyclopentanone was added thereto as the main solvent to obtain a solution containing polymer compound (A-3). The molecular weight of the polymer compound in this solution was measured by GPC, consequently finding a weight average molecular weight of 30,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

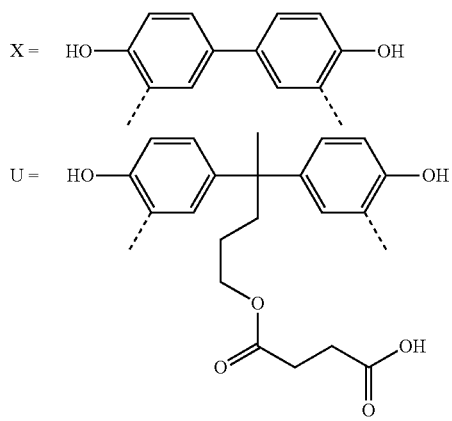

[Synthesis Example 9] Synthesis of Polymer Compound (A-4)

A polymer compound was synthesized in the same manner as in Synthesis Example 6 except that 188 g of compound (M-10) was used in place of 85 g of compound (M-8), and cyclopentanone was added thereto as the main solvent to obtain a solution containing polymer compound (A-4). The molecular weight of the polymer compound in this solution was measured by GPC, consequently finding a weight average molecular weight of 26,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

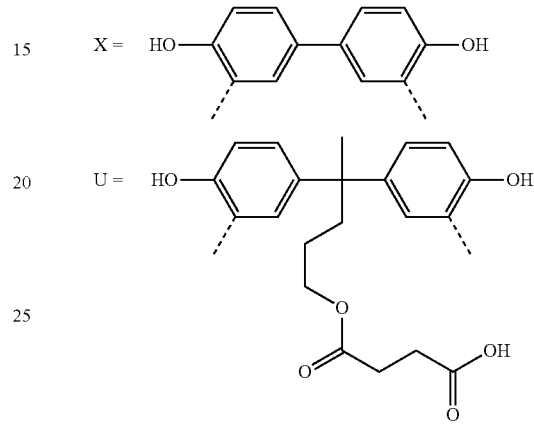

[Synthesis Example 10] Synthesis of Polymer Compound (A-5)

A polymer compound was synthesized in the same manner as in Synthesis Example 6 except that 141 g of compound (M-11) was used in place of 85 g of compound (M-8), and cyclopentanone was added thereto as the main solvent to obtain a solution containing polymer compound (A-5). The molecular weight of the polymer compound in this solution was measured by GPC, consequently finding a weight average molecular weight of 10,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

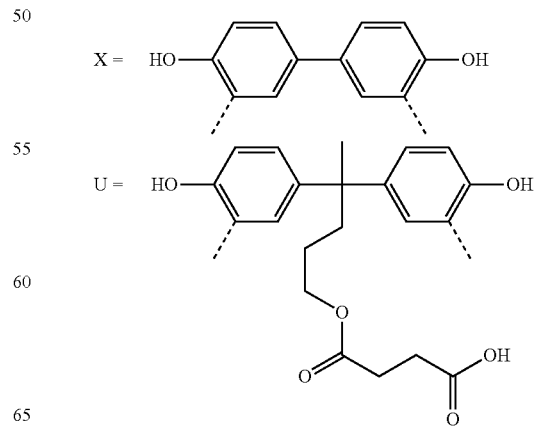

[Synthesis Example 11] Synthesis of Polymer Compound (A-6)

A 3-L flask equipped with a stirrer, thermometer, nitrogen purge system, and reflux condenser was charged with 411 g of toluene and 120 g of compound (M-1) to make a solution. To the solution were added 45 g of compound (M-3), 24 g of compound (M-4), and 219 g of compound (M-10), and the resulting mixture was heated at 60° C. Thereafter, 1.3 g of carbon carried platinum catalyst (5 mass %) was added thereto, and the mixture was heated at 90° C. and aged for 3 hours. Then, the mixture was cooled to 60° C., 1.3 g of carbon carried platinum catalyst (5 mass %) was added again, and 73 g of compound (M-12) was added dropwise into the flask over 30 minutes. At this time, the temperature inside the flask was increased to 65 to 67° C. After dropwise addition, the mixture was further aged at 90° C. for 3 hours and cooled to room temperature. Then, 780 g of methyl isobutyl ketone was added to the reaction solution, and this reaction solution was filtered under pressure through a filter to remove the platinum catalyst. Further, 780 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 1,050 g of tetrahydrofuran was added thereto. The tetrahydrofuran solution was then concentrated under reduced pressure so as to have a solid concentration of 30 mass %.

Then, a 3-L flask equipped with a stirrer, thermometer, nitrogen purge system, and reflux condenser was charged with 1,500 g of the tetrahydrofuran solution containing 30 mass % of the polymer compound; and 31 g of succinic anhydride and 32 g of triethylamine were added thereto, and the mixture was heated at 50° C. After stirring for 2 hours, the mixture was cooled to room temperature, and 900 g of saturated aqueous ammonium chloride solution and 1,500 g of ethyl acetate were added to terminate the reaction. Then, the aqueous layer was removed, and liquid separation and water-washing operation was repeated 5 times with 900 g of ultrapure water. The solvent of the collected organic layer was distilled off, and 600 g of cyclopentanone was added thereto. The resulting cyclopentanone solution was then concentrated under reduced pressure so as to have a solid concentration of 40 to 50 mass %, yielding a solution containing polymer compound (A-6) having carboxylic acid and cyclopentanone as the main solvent. The molecular weight of the polymer compound in this solution was measured by GPC, consequently finding a weight average molecular weight of 24,000 in terms of polystyrene. The polymer compound corresponds to the general formula (1) wherein a=0.293, b=0.107, c=0, d=0, e=0, f=0, g=0.440, h=0.160, i=0, j=0, and X and U are as follows.

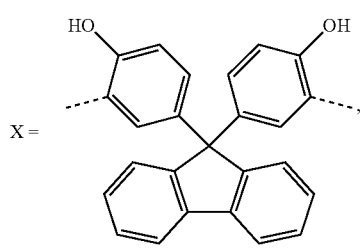

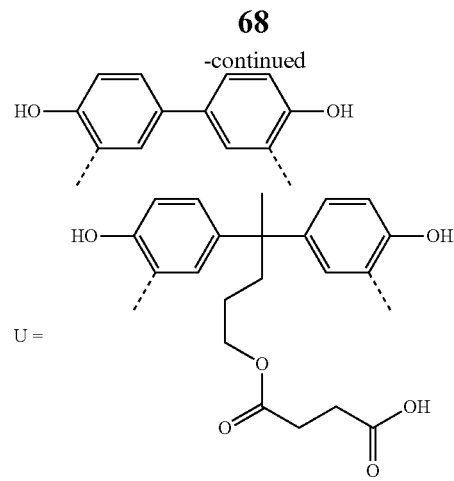

[Synthesis Example 12] Synthesis of Polymer Compound (A-7)

A polymer compound was synthesized in the same manner as in Synthesis Example 11 except that 17 g of compound (M-5) was used in place of 24 g of compound (M-4), and cyclopentanone was added thereto as the main solvent to obtain a solution containing polymer compound (A-7). The molecular weight of the polymer compound in this solution was measured by GPC, consequently finding a weight average molecular weight of 23,000 in terms of polystyrene. The polymer compound corresponds to the general formula (1) wherein a=0.293, b=0.107, c=0, d=0, e=0, f=0, g=0.440, h=0.160, i=0, j=0, and X and U are as follows.

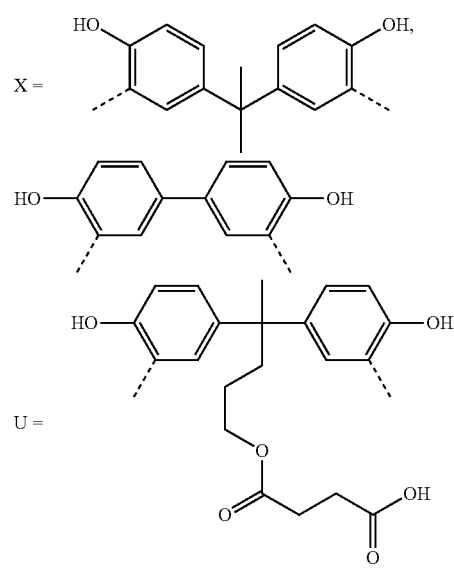

[Synthesis Example 13] Synthesis of Polymer Compound (A-8)

A polymer compound was synthesized in the same manner as in Synthesis Example 11 except that 24 g of compound (M-6) was used in place of 24 g of compound (M-4), and cyclopentanone was added thereto as the main solvent to obtain a solution containing polymer compound (A-8). The molecular weight of the polymer compound in this solution was measured by GPC, consequently finding a weight average molecular weight of 23,000 in terms of polystyrene. The polymer compound corresponds to the general formula (1) wherein a=0.220, b=0.080, c=0.073, d=0.027, e=0, f=0, g=0.440, h=0.160, i=0, j=0, and X, Y, and U are as follows.

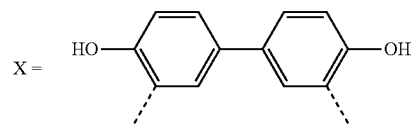

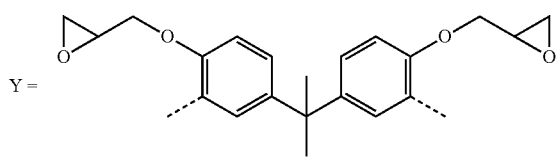

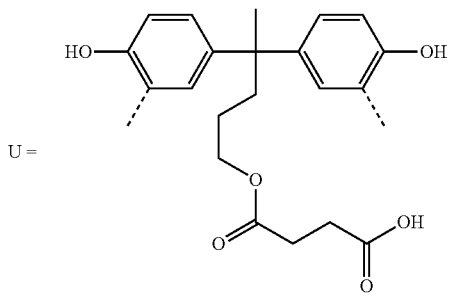

[Synthesis Example 14] Synthesis of Polymer Compound (A-9)

A polymer compound was synthesized in the same manner as in Synthesis Example 6 except that 131 g of compound (M-2) was used in place of 120 g of compound (M-1), and cyclopentanone was added thereto as the main solvent to obtain a solution containing polymer compound (A-9). The molecular weight of the polymer compound in this solution was measured by GPC, consequently finding a weight average molecular weight of 10,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

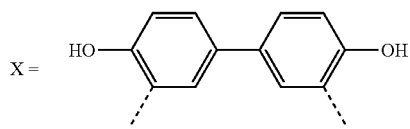

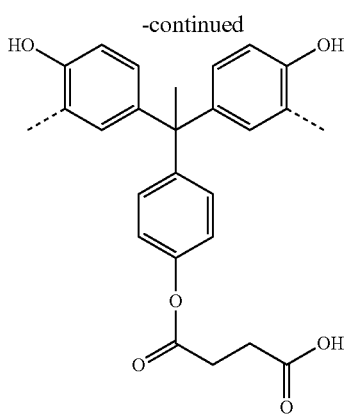

[Synthesis Example 15] Synthesis of Polymer Compound (A-10)

A polymer compound was synthesized in the same manner as in Synthesis Example 6 except that 48 g of cyclohexyldicarboxylic anhydride was used in place of 31 g of succinic anhydride, and cyclopentanone was added thereto as the main solvent to obtain a solution containing polymer compound (A-10). The molecular weight of the polymer compound in this solution was measured by GPC, consequently finding a weight average molecular weight of 10,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

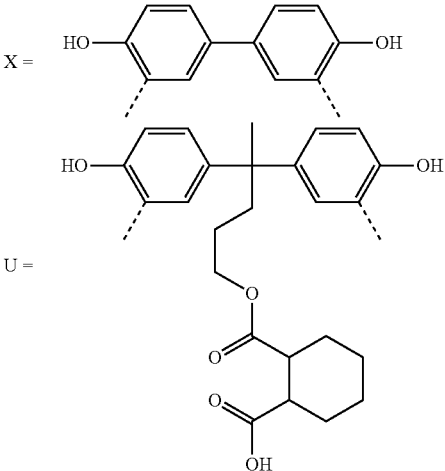

[Synthesis Example 16] Synthesis of Polymer Compound (A-11)

A polymer compound was synthesized in the same manner as in Synthesis Example 6 except that 51 g of 5-norbornene-2,3-dicarboxylic anhydride was used in place of 31 g of succinic anhydride, and cyclopentanone was added thereto as the main solvent to obtain a solution containing polymer compound (A-11). The molecular weight of the polymer compound in this solution was measured by GPC, consequently finding a weight average molecular weight of 10,000 in terms of polystyrene. The polymer compound corresponds to the general formula (1) wherein a=0.220, b=0.080, c=0, d=0, e=0, f=0, g=0.513, h=0.187, i=0, j=0, and X and U are as follows.

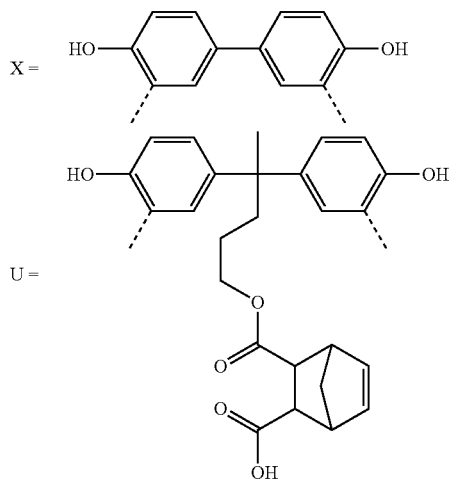

[Synthesis Example 17] Synthesis of Polymer Compound (A-12)

A 3-L flask equipped with a stirrer, thermometer, nitrogen purge system, and reflux condenser was charged with 350 g of toluene and 171 g of compound (M-1) to make a solution. To the solution was added 85 g of compound (M-7), and the resulting mixture was heated at 60° C. Thereafter, 1.1 g of carbon carried platinum catalyst (5 mass %) was added thereto, and the mixture was heated at 90° C. and aged for 3 hours. Then, the mixture was cooled to 60° C., 1.1 g of carbon carried platinum catalyst (5 mass %) was added again, and 62 g of compound (M-11) was added dropwise into the flask over 30 minutes. At this time, the temperature inside the flask was increased to 65 to 67° C. After dropwise addition, the mixture was further aged at 90° C. for 3 hours and cooled to room temperature. Then, 780 g of methyl isobutyl ketone was added to the reaction solution, and this reaction solution was filtered under pressure through a filter to remove the platinum catalyst. Further, 780 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 750 g of tetrahydrofuran was added thereto. The tetrahydrofuran solution was then concentrated under reduced pressure so as to have a solid concentration of 30 mass %.

Then, a 3-L flask equipped with a stirrer, thermometer, nitrogen purge system, and reflux condenser was charged with 1,000 g of the tetrahydrofuran solution containing 30 mass % of the polymer compound; and 32 g of succinic anhydride and 33 g of triethylamine were added thereto, and the mixture was heated at 50° C. After stirring for 2 hours, the mixture was cooled to room temperature, and 900 g of saturated aqueous ammonium chloride solution and 1,500 g of ethyl acetate were added to terminate the reaction. Then, the aqueous layer was removed, and liquid separation and water-washing operation was repeated 5 times with 900 g of ultrapure water. The solvent of the collected organic layer was distilled off, and 600 g of cyclopentanone was added thereto. The resulting cyclopentanone solution was then concentrated under reduced pressure so as to have a solid concentration of 40 to 50 mass %, yielding a solution containing polymer compound (A-12) having carboxylic acid and cyclopentanone as the main solvent. The molecular weight of the polymer compound in this solution was measured by GPC, consequently finding a weight average molecular weight of 10,000 in terms of polystyrene. The polymer compound corresponds to the general formula (1) wherein a=0, b=0, c=0, d=0, e=0.220, f=0.080, g=0.513, h=0.187, i=0, j=0, and W and U are as follows.

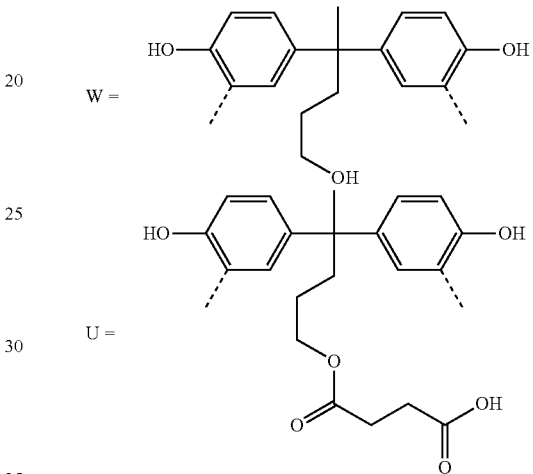

[Synthesis Example 18] Synthesis of Polymer Compound (A-13)

A polymer compound was synthesized in the same manner as in Synthesis Example 17 except that 46 g of succinic anhydride and 46 g of triethylamine were used in place of 32 g of succinic anhydride and 33 g of triethylamine respectively, and cyclopentanone was added thereto as the main solvent to obtain a solution containing polymer compound (A-13). The molecular weight of the polymer compound in this solution was measured by GPC, consequently finding a weight average molecular weight of 10,000 in terms of polystyrene. The polymer compound corresponds to the general formula (1) wherein a=0, b=0, c=0, d=0, e=0, f=0, g=0.733, h=0.267, i=0, j=0, and U is as follows.

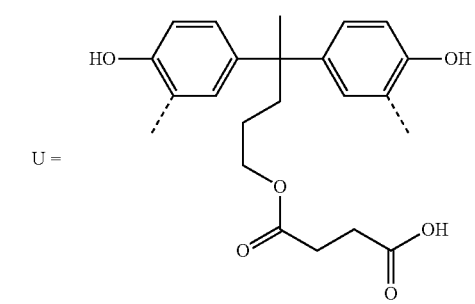

[Synthesis Example 19] Synthesis of Polymer Compound (A-14)

A 500-mL flask equipped with a stirrer, thermometer, nitrogen purge system, and reflux condenser was charged with 30 g of component (M-7), 13.2 g of component (M-8), 13 g of toluene, and 45 g of propylene glycol monomethyl ether acetate, and the mixture was stirred and heated at 60° C. Thereafter, 0.2 g of carbon carried platinum catalyst (5 mass %) was added thereto, and the mixture was heated at 90° C. and aged for 3 hours. Then, the mixture was cooled to 60° C., 0.2 g of carbon carried platinum catalyst (5 mass %) was added again, and 14 g of compound (M-12) was added dropwise into the flask over 30 minutes. At this time, the temperature inside the flask was increased to 65 to 67° C. After dropwise addition, the mixture was further aged at 90° C. for 3 hours and cooled to room temperature. Then, 130 g of methyl isobutyl ketone was added to the reaction solution, and this reaction solution was filtered under pressure through a filter to remove the platinum catalyst. Further, 130 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 150 g of cyclopentanone was added thereto. The cyclopentanone solution was then concentrated under reduced pressure so as to have a solid concentration of 40 to 50 mass %, yielding a solution containing polymer compound (A-14) having acidic phenol and cyclopentanone as the main solvent. The molecular weight of the polymer compound in this solution was measured by GPC, consequently finding a weight average molecular weight of 10,000 in terms of polystyrene. The polymer compound corresponds to the general formula (1) wherein a=0, b=0, c=0, d=0, e=0, f=0, g=0, h=0, i=0.8, j=0.2, and S is as follows.

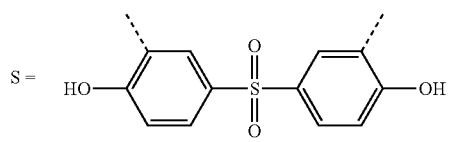

[Synthesis Example 20] Synthesis of Polymer Compound (A-15)

A 500-mL flask equipped with a stirrer, thermometer, nitrogen purge system, and reflux condenser was charged with 50 g of component (M-7), 17.3 g of component (M-3), 31.9 g of component (M-8), 50 g of toluene, and 75 g of propylene glycol monomethyl ether acetate, and the mixture was stirred and heated at 60° C. Thereafter, 0.4 g of carbon carried platinum catalyst (5 mass %) was added thereto, and the mixture was heated at 90° C. and aged for 3 hours. Then, the mixture was cooled to 60° C., 0.4 g of carbon carried platinum catalyst (5 mass %) was added again, and 33.5 g of compound (M-12) was added dropwise into the flask over 30 minutes. At this time, the temperature inside the flask was increased to 65 to 67° C. After dropwise addition, the mixture was further aged at 90° C. for 3 hours and cooled to room temperature. Then, 330 g of methyl isobutyl ketone was added to the reaction solution, and this reaction solution was filtered under pressure through a filter to remove the platinum catalyst. Further, 330 g of pure water was added to the obtained polymer compound solution, and the mixture was stirred and allowed to stand for liquid separation to remove the lower aqueous layer. This liquid separation and water-washing operation was repeated 6 times to remove trace amounts of acid component in the polymer compound solution. The solvent in the resulting polymer compound solution was distilled off under reduced pressure, and 200 g of cyclopentanone was added thereto. The cyclopentanone solution was then concentrated under reduced pressure so as to have a solid concentration of 40 to 50 mass %, yielding a solution containing polymer compound (A-15) having acidic phenol and cyclopentanone as the main solvent. The molecular weight of the polymer compound in this solution was measured by GPC, consequently finding a weight average molecular weight of 10,000 in terms of polystyrene. The polymer compound corresponds to the general formula (1) wherein a=0.16, b=0.04, c=0, d=0, e=0, f=0, g=0, h=0, i=0.64, j=0.16, and X and S are as follows.

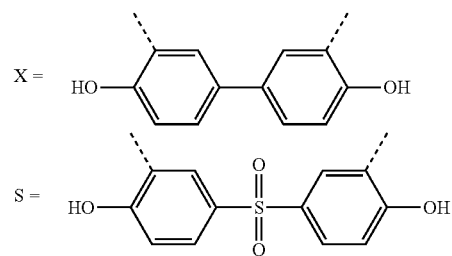

[Synthesis Example 21] Synthesis of Polymer Compound (A-16)

A polymer compound was synthesized in the same manner as in Synthesis Example 20 except that 28 g of compound (M-4) were used in place of 17.3 g of compound (M-3), and cyclopentanone was added thereto as the main solvent to obtain a solution containing polymer compound (A-16). The molecular weight of the polymer compound in this solution was measured by GPC, consequently finding a weight average molecular weight of 10,000 in terms of polystyrene. The polymer compound corresponds to the general formula (1) wherein a=0.16, b=0.04, c=0, d=0, e=0, f=0, g=0, h=0, i=0.64, j=0.16, and X and S are as follows.

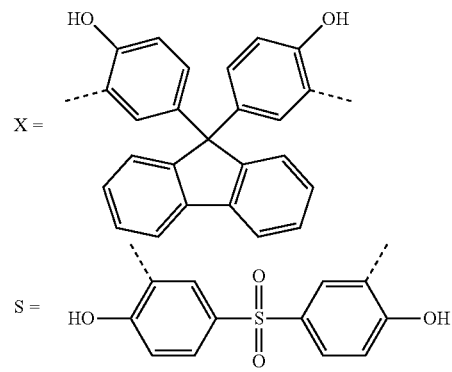

Each solution of the polymer compounds synthesized in Synthesis Examples 6 to 21 was mixed with a photosensitive material capable of generating an acid by light and increasing a dissolution rate in an aqueous alkaline solution, a crosslinking agent, and cyclopentanone as an additional solvent with the composition and the formulation amount as shown in Table 1 and Table 2 to prepare a resin composition with a concentration of 45 mass % in terms of the resin. Then, the composition was stirred, mixed, dissolved, and then filtered through a 0.5 μm filter made of Teflon (registered trade mark) for microfiltration to obtain a positive photosensitive resin composition.

TABLE 1

| Positive photosensitive resin composition | (A) Polymer compound | (B) Photosensitive material | (C) Crosslinking agent | | |
|---|---|---|---|---|---|
| Positive photosensitive resin composition 1 | A-1 (100 parts by mass) | B-38' (15 parts by mass) | C-22 (5 parts by mass) | C-12 (15 parts by mass) | — |
| Positive photosensitive resin composition 2 | A-2 (100 parts by mass) | B-38' (15 parts by mass) | C-22 (5 parts by mass) | C-12 (15 parts by mass) | — |
| Positive photosensitive resin composition 3 | A-3 (100 parts by mass) | B-38' (15 parts by mass) | C-22 (5 parts by mass) | C-12 (15 parts by mass) | — |
| Positive photosensitive resin composition 4 | A-4 (100 parts by mass) | B-38' (15 parts by mass) | C-22 (5 parts by mass) | C-12 (15 parts by mass) | — |
| Positive photosensitive resin composition 5 | A-5 (100 parts by mass) | B-38' (15 parts by mass) | C-22 (5 parts by mass) | C-12 (15 parts by mass) | — |
| Positive photosensitive resin composition 6 | A-6 (100 parts by mass) | B-38' (15 parts by mass) | C-22 (5 parts by mass) | C-12 (15 parts by mass) | — |
| Positive photosensitive resin composition 7 | A-7 (100 parts by mass) | B-38' (15 parts by mass) | C-22 (5 parts by mass) | C-12 (15 parts by mass) | — |
| Positive photosensitive resin composition 8 | A-8 (100 parts by mass) | B-38' (15 parts by mass) | C-22 (5 parts by mass) | C-12 (15 parts by mass) | — |
| Positive photosensitive resin composition 9 | A-9 (100 parts by mass) | B-38' (15 parts by mass) | C-22 (5 parts by mass) | C-12 (15 parts by mass) | — |
| Positive photosensitive resin composition 10 | A-10 (100 parts by mass) | B-38' (15 parts by mass) | C-22 (5 parts by mass) | C-12 (15 parts by mass) | — |
| Positive photosensitive resin composition 11 | A-11 (100 parts by mass) | B-38' (15 parts by mass) | C-22 (5 parts by mass) | C-12 (15 parts by mass) | — |
| Positive photosensitive resin composition 12 | A-12 (100 parts by mass) | B-38' (15 parts by mass) | C-22 (5 parts by mass) | C-12 (15 parts by mass) | — |
| Positive photosensitive resin composition 13 | A-13 (100 parts by mass) | B-38' (15 parts by mass) | C-22 (5 parts by mass) | C-12 (15 parts by mass) | — |
| Positive photosensitive resin composition 14 | A-14 (100 parts by mass) | B-38' (15 parts by mass) | C-22 (5 parts by mass) | C-12 (15 parts by mass) | — |
| Positive photosensitive resin composition 15 | A-15 (100 parts by mass) | B-38' (15 parts by mass) | C-22 (5 parts by mass) | C-12 (15 parts by mass) | — |
| Positive photosensitive resin composition 16 | A-16 (100 parts by mass) | B-38' (15 parts by mass) | C-22 (5 parts by mass) | C-12 (15 parts by mass) | — |
| Positive photosensitive resin composition 17 | A-2 (100 parts by mass) | B-3' (15 parts by mass) | C-22 (5 parts by mass) | C-12 (15 parts by mass) | — |
| Positive photosensitive resin composition 18 | A-2 (100 parts by mass) | B-33' (15 parts by mass) | C-22 (5 parts by mass) | C-12 (15 parts by mass) | — |
| Positive photosensitive resin composition 19 | A-2 (100 parts by mass) | B-34' (15 parts by mass) | C-22 (5 parts by mass) | C-12 (15 parts by mass) | — |

TABLE 2

| Positive photosensitive resin composition | (A) Polymer compound | (B) Photosensitive material | (C) Crosslinking agent | | |
|---|---|---|---|---|---|
| Positive photosensitive resin composition 20 | A-15 (100 parts by mass) | B-3' (15 parts by mass) | C-22 (5 parts by mass) | C-12 (15 parts by mass) | — |
| Positive photosensitive resin composition 21 | A-15 (100 parts by mass) | B-33' (15 parts by mass) | C-22 (5 parts by mass) | C-12 (15 parts by mass) | — |
| Positive photosensitive resin composition 22 | A-15 (100 parts by mass) | B-34' (15 parts by mass) | C-22 (5 parts by mass) | C-12 (15 parts by mass) | — |
| Positive photosensitive resin composition 23 | A-6 (100 parts by mass) | B-38' (15 parts by mass) | C-22 (20 parts by mass) | — | — |
| Positive photosensitive resin composition 24 | A-6 (100 parts by mass) | B-38' (15 parts by mass) | C-22 (5 parts by mass) | C-3 (15 parts by mass) | — |
| Positive photosensitive resin composition 25 | A-6 (100 parts by mass) | B-38' (15 parts by mass) | C-22 (5 parts by mass) | C-4 (15 parts by mass) | — |
| Positive photosensitive resin composition 26 | A-6 (100 parts by mass) | B-38' (15 parts by mass) | C-22 (5 parts by mass) | C-5 (15 parts by mass) | — |
| Positive photosensitive resin composition 27 | A-6 (100 parts by mass) | B-38' (15 parts by mass) | C-22 (5 parts by mass) | C-6 (15 parts by mass) | — |
| Positive photosensitive resin composition 28 | A-6 (100 parts by mass) | B-38' (15 parts by mass) | C-22 (5 parts by mass) | C-7 (15 parts by mass) | — |
| Positive photosensitive resin composition 29 | A-6 (100 parts by mass) | B-38' (15 parts by mass) | C-22 (5 parts by mass) | C-8 (15 parts by mass) | — |
| Positive photosensitive resin composition 30 | A-6 (100 parts by mass) | B-38' (15 parts by mass) | C-22 (5 parts by mass) | C-9 (15 parts by mass) | — |
| Positive photosensitive resin composition 31 | A-6 (100 parts by mass) | B-38' (15 parts by mass) | C-22 (5 parts by mass) | C-10 (15 parts by mass) | — |
| Positive photosensitive resin composition 32 | A-6 (100 parts by mass) | B-38' (15 parts by mass) | C-22 (5 parts by mass) | C-13 (15 parts by mass) | — |
| Positive photosensitive resin composition 33 | A-6 (100 parts by mass) | B-38' (15 parts by mass) | C-22 (5 parts by mass) | C-14 (15 parts by mass) | — |
| Positive photosensitive resin composition 34 | A-6 (100 parts by mass) | B-38' (15 parts by mass) | C-22 (5 parts by mass) | C-12 (15 parts by mass) | C-15 (15 parts by mass) |
| Positive photosensitive resin composition 35 | A-6 (100 parts by mass) | B-38' (15 parts by mass) | C-22 (5 parts by mass) | C-12 (15 parts by mass) | C-21 (5 parts by mass) |
| Positive photosensitive resin composition 36 | A-6 (100 parts by mass) | B-38' (15 parts by mass) | C-22 (5 parts by mass) | C-5 (15 parts by mass) | C-21 (5 parts by mass) |

The photosensitive materials (B-3'), (B-33'), (B-38'), and (B-34') of component (B) listed in Table 1 and Table 2 are shown below.

The crosslinking agents (C-3) to (C-10), (C-12) to (C-15), (C-21), and (C-22) of component (C) listed in Table 1 and Table 2 are shown below.

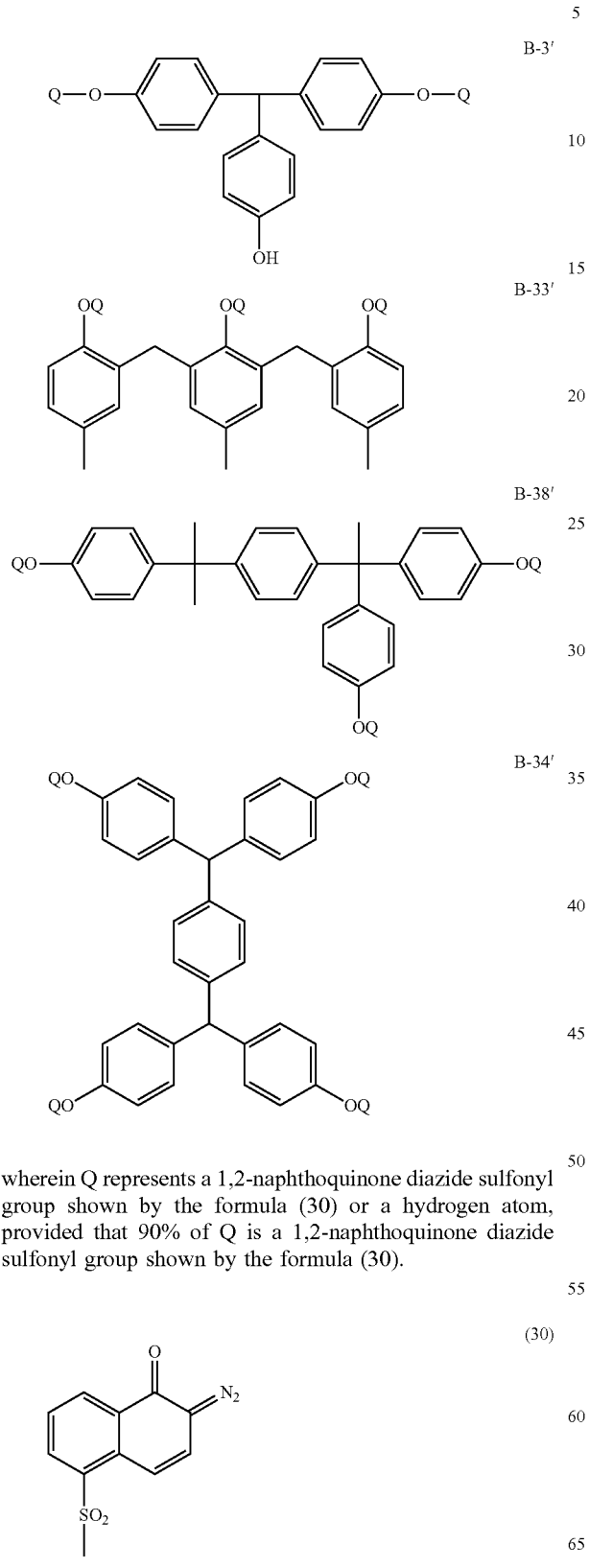

wherein Q represents a 1,2-naphthoquinone diazide sulfonyl group shown by the formula (30) or a hydrogen atom, provided that 90% of Q is a 1,2-naphthoquinone diazide sulfonyl group shown by the formula (30).

-continued
C-7
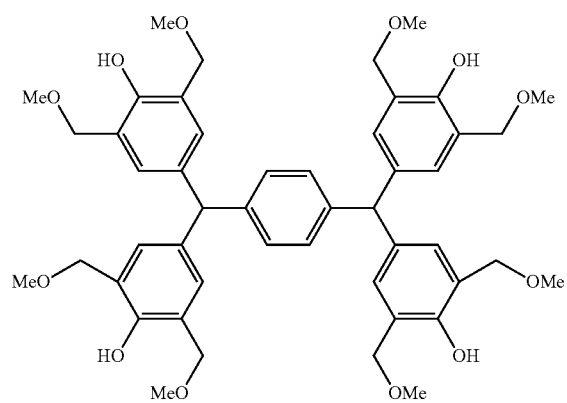
C-8
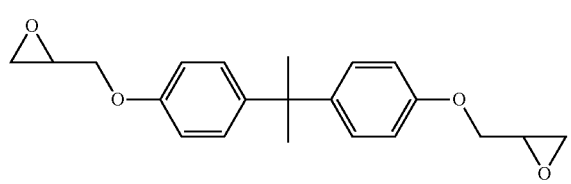
C-9
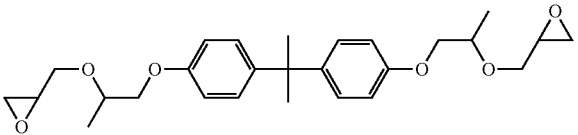
C-10
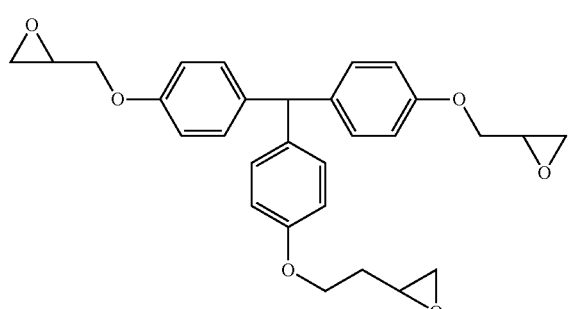
C-12
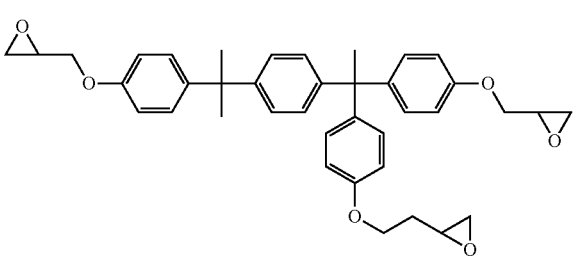
-continued
C-13
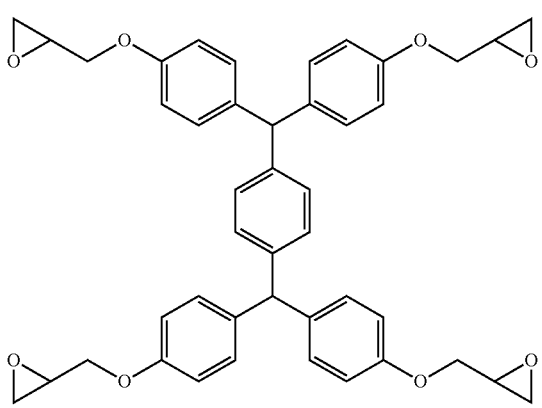
C-14
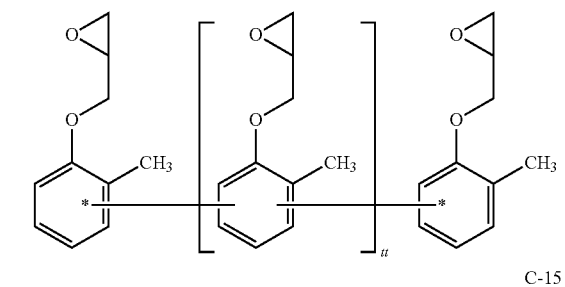
C-15
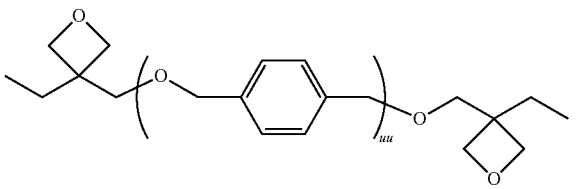
C-21
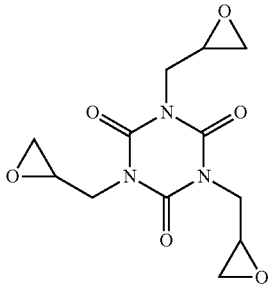
C-22
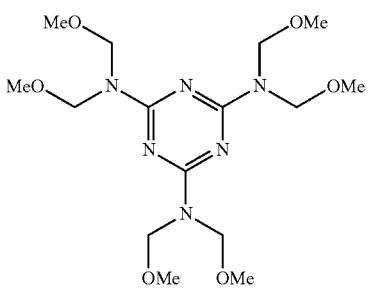
wherein 2≤tt≤3 and 1≤uu≤3.
II. Exposure and Patterning
5 mL of the positive photosensitive resin compositions 1 to 36 were each dispensed on a silicon substrate, and the substrate was rotated, i.e., each composition was applied by the spin coating method so as to give a film thickness of 20 µm.

Then, pre-baking was performed on a hot plate at 100° C. for 2 minutes. To the substrate was attached a mask for forming 20 µm holes arranged in 1:1 lengthwise and breadthwise, and exposure was performed with a broad band light by a mask aligner (product name: MA-8) manufactured by SUSS Micro Tec AG. After exposure, patterning was carried out by repeating one-minute puddle development three times with a 2.38% tetramethylammonium hydroxide aqueous solution as the developer. Then, the pattern formed on the substrate was post-cured with an oven at 180° C. for 2 hours in a nitrogen atmosphere.

In a similar manner, a pattern was respectively formed on a SiN substrate and on a Cu substrate in place of the silicon substrate.

Then, each substrate was cut so that the shape of the obtained hole pattern could be observed. The shape of the hole pattern was observed with a scanning electron microscope (SEM). An optimum exposure dose (exposure dose in terms of 365 nm light) by which the hole pattern could achieve the same aperture diameter as a mask size of 20 is shown in Table 3 and Table 4. The observed shape is also shown in Table 3 and Table 4.

TABLE 3

| Example | Positive photosensitive resin composition | Pattern profile and exposure dose (mJ) on silicon substrate | Pattern profile and exposure dose (mJ) on SiN substrate | Pattern profile and exposure dose (mJ) on Cu substrate |
| --- | --- | --- | --- | --- |
| Example 1 | Positive photosensitive resin composition 1 | Forward tapered 320 mJ | Forward tapered 360 mJ | Forward tapered 320 mJ |
| Example 2 | Positive photosensitive resin composition 2 | Forward tapered 380 mJ | Forward tapered 400 mJ | Forward tapered 380 mJ |
| Example 3 | Positive photosensitive resin composition 3 | Forward tapered 400 mJ | Forward tapered 460 mJ | Forward tapered 420 mJ |
| Example 4 | Positive photosensitive resin composition 4 | Forward tapered 460 mJ | Forward tapered 500 mJ | Forward tapered 460 mJ |
| Example 5 | Positive photosensitive resin composition 5 | Forward tapered 500 mJ | Forward tapered 500 mJ | Forward tapered 520 mJ |
| Example 6 | Positive photosensitive resin composition 6 | Forward tapered 500 mJ | Forward tapered 540 mJ | Forward tapered 500 mJ |
| Example 7 | Positive photosensitive resin composition 7 | Forward tapered 500 mJ | Forward tapered 520 mJ | Forward tapered 500 mJ |
| Example 8 | Positive photosensitive resin composition 8 | Forward tapered 520 mJ | Forward tapered 560 mJ | Forward tapered 520 mJ |
| Example 9 | Positive photosensitive resin composition 9 | Forward tapered 500 mJ | Forward tapered 540 mJ | Forward tapered 500 mJ |
| Example 10 | Positive photosensitive resin composition 10 | Forward tapered 520 mJ | Forward tapered 560 mJ | Forward tapered 520 mJ |
| Example 11 | Positive photosensitive resin composition 11 | Forward tapered 540 mJ | Forward tapered 600 mJ | Forward tapered 560 mJ |
| Example 12 | Positive photosensitive resin composition 12 | Forward tapered 540 mJ | Forward tapered 600 mJ | Forward tapered 560 mJ |
| Example 13 | Positive photosensitive resin composition 13 | Forward tapered 520 mJ | Forward tapered 560 mJ | Forward tapered 520 mJ |
| Example 14 | Positive photosensitive resin composition 14 | Forward tapered 540 mJ | Forward tapered 600 mJ | Forward tapered 560 mJ |
| Example 15 | Positive photosensitive resin composition 15 | Forward tapered 500 mJ | Forward tapered 540 mJ | Forward tapered 500 mJ |
| Example 16 | Positive photosensitive resin composition 16 | Forward tapered 540 mJ | Forward tapered 560 mJ | Forward tapered 560 mJ |
| Example 17 | Positive photosensitive resin composition 17 | Forward tapered 520 mJ | Forward tapered 560 mJ | Forward tapered 520 mJ |
| Example 18 | Positive photosensitive resin composition 18 | Forward tapered 480 mJ | Forward tapered 520 mJ | Forward tapered 480 mJ |

TABLE 3-continued

| Example | Positive photosensitive resin composition | Pattern profile and exposure dose (mJ) on silicon substrate | Pattern profile and exposure dose (mJ) on SiN substrate | Pattern profile and exposure dose (mJ) on Cu substrate |
| --- | --- | --- | --- | --- |
| Example 19 | Positive photosensitive resin composition 19 | Forward tapered 480 mJ | Forward tapered 500 mJ | Forward tapered 480 mJ |

TABLE 4

| Example | Positive photosensitive resin composition | Pattern profile and exposure dose (mJ) on silicon substrate | Pattern profile and exposure dose (mJ) on SiN substrate | Pattern profile and exposure dose (mJ) on Cu substrate |
| --- | --- | --- | --- | --- |
| Example 20 | Positive photosensitive resin composition 20 | Forward tapered 520 mJ | Forward tapered 560 mJ | Forward tapered 520 mJ |
| Example 21 | Positive photosensitive resin composition 21 | Forward tapered 520 mJ | Forward tapered 560 mJ | Forward tapered 520 mJ |
| Example 22 | Positive photosensitive resin composition 22 | Forward tapered 520 mJ | Forward tapered 560 mJ | Forward tapered 520 mJ |
| Example 23 | Positive photosensitive resin composition 23 | Forward tapered 540 mJ | Forward tapered 560 mJ | Forward tapered 560 mJ |
| Example 24 | Positive photosensitive resin composition 24 | Forward tapered 560 mJ | Forward tapered 560 mJ | Forward tapered 560 mJ |
| Example 25 | Positive photosensitive resin composition 25 | Forward tapered 560 mJ | Forward tapered 560 mJ | Forward tapered 560 mJ |
| Example 26 | Positive photosensitive resin composition 26 | Forward tapered 500 mJ | Forward tapered 540 mJ | Forward tapered 500 mJ |
| Example 27 | Positive photosensitive resin composition 27 | Forward tapered 520 mJ | Forward tapered 560 mJ | Forward tapered 520 mJ |
| Example 28 | Positive photosensitive resin composition 28 | Forward tapered 560 mJ | Forward tapered 560 mJ | Forward tapered 560 mJ |
| Example 29 | Positive photosensitive resin composition 29 | Forward tapered 560 mJ | Forward tapered 580 mJ | Forward tapered 560 mJ |
| Example 30 | Positive photosensitive resin composition 30 | Forward tapered 540 mJ | Forward tapered 560 mJ | Forward tapered 540 mJ |
| Example 31 | Positive photosensitive resin composition 31 | Forward tapered 540 mJ | Forward tapered 560 mJ | Forward tapered 540 mJ |
| Example 32 | Positive photosensitive resin composition 32 | Forward tapered 560 mJ | Forward tapered 580 mJ | Forward tapered 560 mJ |
| Example 33 | Positive photosensitive resin composition 33 | Forward tapered 580 mJ | Forward tapered 580 mJ | Forward tapered 580 mJ |
| Example 34 | Positive photosensitive resin composition 34 | Forward tapered 560 mJ | Forward tapered 580 mJ | Forward tapered 560 mJ |
| Example 35 | Positive photosensitive resin composition 35 | Forward tapered 580 mJ | Forward tapered 600 mJ | Forward tapered 580 mJ |
| Example 36 | Positive photosensitive resin composition 36 | Forward tapered 580 mJ | Forward tapered 580 mJ | Forward tapered 580 mJ |

As shown in Tables 3 and 4, positive photosensitive resin compositions 1 to 36 of the present invention could form a pattern by using a 2.38% tetramethylammonium hydroxide aqueous solution as the developer. Moreover, the pattern profile of positive photosensitive resin compositions 1 to 36 was forward tapered, and very good pattern shape could be obtained. Furthermore, no delamination was observed even in the substrates such as SiN substrate and Cu substrate, which easily cause delamination during development.

III. Production of Photo-Curable Dry Film

For a photo-curable dry film, each solution of the polymer compounds synthesized in Synthesis Examples 6 to 21 was mixed with a photosensitive material capable of generating an acid by light and increasing a dissolution rate in an aqueous alkaline solution and a crosslinking agent with the composition and the formulation amount as shown in Table 1 in the same manner as above except that no additional cyclopentanone was used. Then, the composition was stirred, mixed, dissolved, and then filtered through a 1.0 μm filter made of Teflon (registered trade mark) for microfiltration to obtain positive photosensitive resin compositions 1' to 16'.

By using a die coater as a film coater and a polyethylene terephthalate film (thickness: 38 μm) as a supporting film, positive photosensitive resin composition 1' to 16' were each applied onto the supporting film so as to give a thickness of 50 Then, the film was caused to pass through a hot-air circulating oven (length: 4 m) at 100° C. over 5 minutes to form a photo-curable resin layer on the supporting film. Further, a polyethylene film (thickness: 50 μm) was laminated as a protective film on the photo-curable resin layer with a laminate roll under a pressure of 1 MPa to produce photo-curable dry films 1 to 16.

The thickness of the photo-curable resin layer was 50 μm. The film examples are summarized in Table 5.

IV. Exposure and Patterning

Each protective film of the photo-curable dry films 1 to 16 thus produced was separated, and the photo-curable resin layer on the supporting film was brought into close contact with a silicon substrate at 100° C. by a vacuum laminator (Product name: TEAM-100RF) manufactured by Takatori Corp., in a vacuum chamber with a vacuum degree of 100 Pa. After the pressure was resumed to normal pressure, the substrate was cooled to 25° C. and taken out from the vacuum laminator, and then the supporting film was removed. After removing the supporting film, pre-baking was carried out on a hot plate at 100° C. for 5 minutes.

To the substrate was attached a mask for forming 40 μm holes arranged in 1:1 lengthwise and breadthwise, and exposure was performed with a broad band light by a mask aligner (product name: MA-8) manufactured by SUSS Micro Tec AG. Thereafter, patterning was carried out by repeating one-minute puddle development five times by using a 2.38% tetramethylammonium hydroxide aqueous solution as the developer. Then, the pattern was post-cured with an oven at 180° C. for 2 hours in a nitrogen atmosphere.

In a similar manner, after laminating the photo-curable dry films 1 to 16 produced above, a pattern was respectively formed on a SiN substrate and on a Cu substrate in place of the silicon substrate.

Then, each substrate was cut so that the shape of the obtained hole pattern could be observed. The shape of the hole pattern was observed with a scanning electron microscope (SEM). An optimum exposure dose (exposure dose in terms of 365 nm light) by which the hole pattern could achieve the same aperture diameter as a mask size of 40 is shown in Table 5.

TABLE 5

| Example | Photo-curable dry film | Pattern profile and exposure dose (mJ) on silicon substrate | Pattern profile and exposure dose (mJ) on SiN substrate | Pattern profile and exposure dose (mJ) on Cu substrate |
| --- | --- | --- | --- | --- |
| Example 37 | Photo-curable dry film 1 | Forward tapered 400 mJ | Forward tapered 460 mJ | Forward tapered 440 mJ |
| Example 38 | Photo-curable dry film 2 | Forward tapered 580 mJ | Forward tapered 620 mJ | Forward tapered 620 mJ |
| Example 39 | Photo-curable dry film 3 | Forward tapered 540 mJ | Forward tapered 580 mJ | Forward tapered 540 mJ |
| Example 40 | Photo-curable dry film 4 | Forward tapered 560 mJ | Forward tapered 620 mJ | Forward tapered 580 mJ |
| Example 41 | Photo-curable dry film 5 | Forward tapered 580 mJ | Forward tapered 640 mJ | Forward tapered 620 mJ |
| Example 42 | Photo-curable dry film 6 | Forward tapered 640 mJ | Forward tapered 640 mJ | Forward tapered 640 mJ |
| Example 43 | Photo-curable dry film 7 | Forward tapered 620 mJ | Forward tapered 680 mJ | Forward tapered 620 mJ |
| Example 44 | Photo-curable dry film 8 | Forward tapered 620 mJ | Forward tapered 660 mJ | Forward tapered 600 mJ |
| Example 45 | Photo-curable dry film 9 | Forward tapered 640 mJ | Forward tapered 680 mJ | Forward tapered 640 mJ |
| Example 46 | Photo-curable dry film 10 | Forward tapered 620 mJ | Forward tapered 680 mJ | Forward tapered 620 mJ |
| Example 47 | Photo-curable dry film 11 | Forward tapered 640 mJ | Forward tapered 540 mJ | Forward tapered 620 mJ |
| Example 48 | Photo-curable dry film 12 | Forward tapered 620 mJ | Forward tapered 640 mJ | Forward tapered 600 mJ |
| Example 49 | Photo-curable dry film 13 | Forward tapered 640 mJ | Forward tapered 620 mJ | Forward tapered 580 mJ |
| Example 50 | Photo-curable dry film 14 | Forward tapered 660 mJ | Forward tapered 640 mJ | Forward tapered 580 mJ |
| Example 51 | Photo-curable dry film 15 | Forward tapered 620 mJ | Forward tapered 640 mJ | Forward tapered 600 mJ |
| Example 52 | Photo-curable dry film 16 | Forward tapered 640 mJ | Forward tapered 640 mJ | Forward tapered 640 mJ |

As shown in Table 5, the photo-curable dry film using the positive photosensitive resin composition of the present invention enabled development with an aqueous alkaline solution and patterning. Moreover, the pattern profile was excellent, and remarkable delamination did not occur on the SiN substrate and the Cu substrate.

V. Filling Property

A 6-inch (150 mm) silicon wafer having 200 circular holes each having an aperture diameter of 10 to 100 µm (10 µm pitch) and a depth of 10 to 120 µm (10 µm pitch) was prepared. With respect to the photo-curable dry films 3 to 5, 10, 14, and 15, each protective film was separated, and the photo-curable resin layer on the supporting film was brought into close contact with the substrate at 100° C. by a vacuum laminator (Product name: TEAM-100RF) manufactured by Takatori Corp., in a vacuum chamber with a vacuum degree of 100 Pa. After the pressure was resumed to normal pressure, the substrate was cooled to 25° C. and taken out from the vacuum laminator, and then the supporting film was removed. After removing the supporting film, pre-baking was carried out on a hot plate at 100° C. for 5 minutes.

Thereafter, without exposure, patterning was carried out by repeating one-minute puddle development five times by using a 2.38% tetramethylammonium hydroxide aqueous solution as the developer. Then, the pattern was post-cured with an oven at 180° C. for 2 hours in a nitrogen atmosphere. The obtained substrate was then diced to expose the cross section of the circular holes, and the cross section of the circular holes was observed with a scanning electron microscope (SEM) to evaluate whether defects were present. The result is given in Table 6.

TABLE 6

| Example | Photo-curable dry film | Observation result of cross section of circular hole |
|---|---|---|
| Example 39 | Photo-curable dry film 3 | No defect<br>Excellent filling property |
| Example 40 | Photo-curable dry film 4 | No defect<br>Excellent filling property |
| Example 41 | Photo-curable dry film 5 | No defect<br>Excellent filling property |
| Example 46 | Photo-curable dry film 10 | No defect<br>Excellent filling property |
| Example 50 | Photo-curable dry film 14 | No defect<br>Excellent filling property |
| Example 51 | Photo-curable dry film 15 | No defect<br>Excellent filling property |

As shown in Table 6, all the circular holes of the silicon wafer bonded with the photo-curable dry film of the present invention were filled without defects. Thus, these films had excellent filling property as the top coat to protect electric and electronic parts.

VI. Electric Characteristics (Dielectric Breakdown Strength)

Each protective film with a thickness of 50 µm was separated from the photo-curable dry films 3 to 5, 10, 14, and 15, and the photo-curable resin layer on the supporting film was brought into close contact with a substrate defined in JIS K 6249 at 100° C. The substrate was then cooled to room temperature, and the supporting film was removed. After removing the supporting film, pre-baking was carried out on a hot plate at 100° C. for 5 minutes. Further, without exposure, the substrate was heated at 110° C. for 5 minutes (PEB) and then cooled. Thereafter, one-minute puddle development was repeated three times by using a 2.38% tetramethylammonium hydroxide aqueous solution as the developer. Then, post-curing was performed with an oven at 180° C. for 2 hours while purging therein with nitrogen to obtain a substrate for measuring the dielectric breakdown strength. The dielectric breakdown strength was measured in accordance with the measurement method defined in JIS K 6249. The result is given in Table 7.

VII. Adhesiveness

Each protective film with a thickness of 50 µm was separated from the photo-curable dry films 3 to 5, 10, 14, and 15, and the photo-curable resin layer on the supporting film was brought into close contact with an untreated 6-inch (150 mm) silicon wafer at 100° C. by a vacuum laminator in a vacuum chamber with a vacuum degree of 100 Pa. After the pressure was resumed to normal pressure, the substrate was cooled to 25° C. and taken out from the vacuum laminator, and then the supporting film was removed. After removing the supporting film, pre-baking was carried out on a hot plate at 100° C. for 5 minutes.

Then, without exposure, the substrate was heated at 110° C. for 5 minutes (PEB) and then cooled. Thereafter, post-curing was carried out with an oven at 180° C. for 2 hours in a nitrogen atmosphere to obtain the wafer with a cured film.

This wafer was cut into a 1×1 cm square. Then, an aluminum pin with epoxy adhesive was fastened to the cut wafer with a dedicated jig. Thereafter, the assembly was heated with an oven at 150° C. for 1 hour to bond the aluminum pin to the wafer. After cooling to room temperature, initial adhesiveness was evaluated based on the resistance force by a thin-film adhesion strength measurement apparatus (Sebastian Five-A). The measurement was performed with a measurement rate of 0.2 kg/sec. FIG. 1 is an explanatory view showing an adhesiveness measurement method. In FIG. 1, reference number 1 denotes a silicon wafer (substrate), 2 denotes a cured film, 3 denotes an aluminum pin with adhesive, 4 denotes a support, 5 denotes a grip, and 6 denotes a tensile direction. The obtained value is an average of 12 measurement points, and a larger value indicates that the cured film has higher adhesion strength with respect to the substrate. The adhesiveness was evaluated by comparing the obtained values. The result is given in Table 7.

Furthermore, a soldering flux liquid was applied to the cured film on the substrate. The cured film was then heated at 220° C. for 30 seconds, cooled, washed with pure water, and dried at room temperature for 2 hours. This cured film was measured with the thin-film adhesion strength measurement apparatus to evaluate adhesiveness after degradation in the same manner as the initial adhesiveness was evaluated. The result is given in Table 7.

VIII. Crack Resistance

Each protective film with a thickness of 50 µm was separated from the photo-curable dry films 3 to 5, 10, 14, and 15, and the photo-curable resin layer on the supporting film was brought into close contact with the same substrate as used in the filling property test at 100° C. by a vacuum laminator in a vacuum chamber with a vacuum degree of 100 Pa. After the pressure was resumed to normal pressure, the substrate was cooled to 25° C. and taken out from the vacuum laminator, and then the supporting film was removed. After removing the supporting film, pre-baking was carried out on a hot plate at 100° C. for 5 minutes.

Thereafter, without exposure, one-minute puddle development was repeated three times by using a 2.38% tetramethylammonium hydroxide aqueous solution as the developer. Then, post-curing was performed with an oven at 180° C. for 2 hours while purging therein with nitrogen.

This substrate having the cured film formed thereon was put into a thermal cycle tester with a temperature profile of −55° C. to +150° C. as one cycle, and subjected to 1,000 cycles to examine whether cracks would be generated in the cured film. The result is given in Table 7.

IX. Resistance to Removing Liquid

Each protective film with a thickness of 50 μm was separated from the photo-curable dry films 3 to 5, 10, 14, and 15, and the photo-curable resin layer on the supporting film was brought into close contact with an untreated 6-inch (150 mm) silicon wafer at 100° C. by a vacuum laminator in a vacuum chamber with a vacuum degree of 100 Pa. After the pressure was resumed to normal pressure, the substrate was cooled to 25° C. and taken out from the vacuum laminator, and then the supporting film was removed.

After removing the supporting film, pre-baking was carried out on a hot plate at 100° C. for 5 minutes. Then, without exposure, the substrate was heated at 110° C. for 5 minutes (PEB) and then cooled. Thereafter, one-minute puddle development was repeated three times by using a 2.38% tetramethylammonium hydroxide aqueous solution as the developer. Then, post-curing was performed with an oven at 180° C. for 2 hours in a nitrogen atmosphere to obtain a 15 mm×15 mm square pattern cured film.

This substrate was soaked in N-methylpyrrolidone (NMP) at room temperature for 1 hour, and the changes in appearance and film thickness were examined to evaluate resistance to the removing liquid. The result is given in Table 7.

TABLE 7

| Example | Electric characteristics Dielectric breakdown strength (V/μm) | Adhesiveness Initial (mN) | Adhesiveness After degradation (mN) | Crack resistance (after thermal cycle test) | Resistance to removing liquid (after soaking in NMP) |
|---|---|---|---|---|---|
| Example 39 | 340 | 400 | 360 | No crack | No change in appearance and film thickness |
| Example 40 | 330 | 420 | 360 | No crack | No change in appearance and film thickness |
| Example 41 | 350 | 380 | 360 | No crack | No change in appearance and film thickness |
| Example 46 | 345 | 390 | 360 | No crack | No change in appearance and film thickness |
| Example 50 | 350 | 400 | 360 | No crack | No change in appearance and film thickness |
| Example 51 | 350 | 420 | 360 | No crack | No change in appearance and film thickness |

As shown in Table 7, the cured film obtained by the patterning process using the photo-curable dry film of the present invention was excellent in all of electric characteristics, adhesiveness, crack resistance, and resistance to removing liquid as the top coat to protect electric and electronic parts.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A positive photosensitive resin composition comprising:
    (A) a polymer compound containing a siloxane chain, the polymer compound having a repeating unit shown by the following general formula (1) and a weight average molecular weight of 3,000 to 500,000;
    (B) a photosensitive material capable of generating an acid by light and increasing a dissolution rate in an aqueous alkaline solution;
    (C) one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group and shown by the following formula (C-2); and
    (D) a solvent,

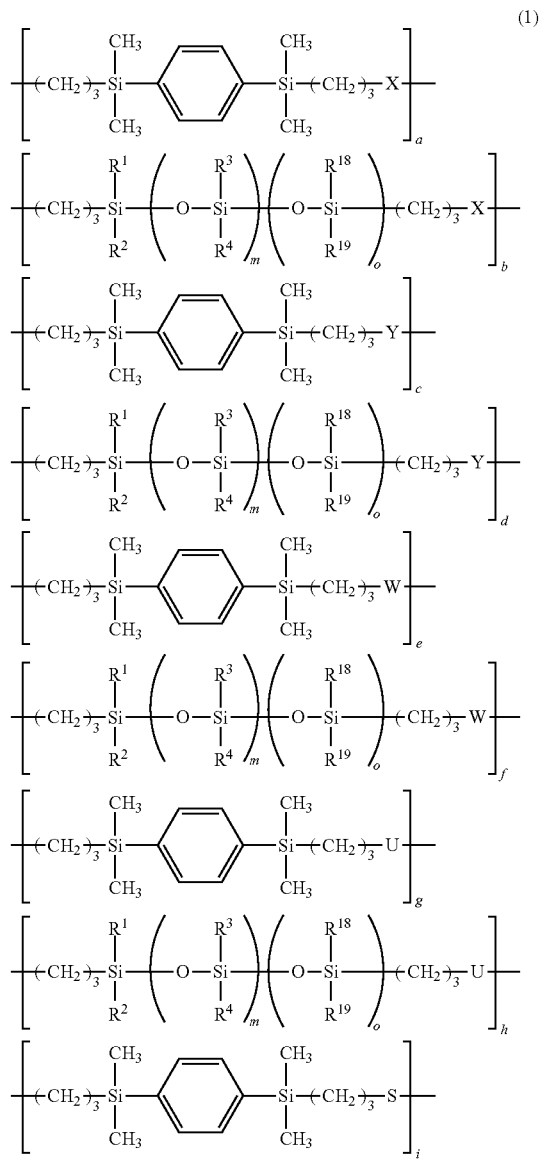

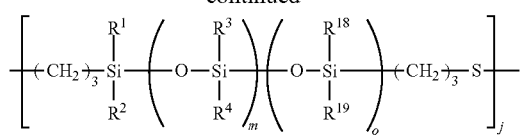

wherein $R^1$ to $R^4$ are the same or different and represent a monovalent organic group having 1 to 15 carbon atoms and optionally containing an oxygen atom; $R^{18}$ and $R^{19}$ are the same or different and represent a monovalent organic group having 1 to 28 carbon atoms and optionally containing an oxygen atom; "m" represents an integer of 1 to 100; "o" represents an integer of 0 to 100; "a", "b", "c", "d", "e" "f", "g", "h", "i", and "j" are each 0 or a positive number, provided that when "g" and "h" are 0, "i" and "j" are a positive number, and when "i" and "j" are 0, "g" and "h" are a positive number; a+b+c+d+e+f+g+h+i+j=1; X represents a divalent organic group shown by the following general formula (2) or the following general formula (3); Y represents a divalent organic group shown by the following general formula (4); W represents a divalent organic group shown by the following general formula (5); U represents a divalent organic group shown by the following general formula (6); and S represents a divalent organic group shown by the following general formula (7),

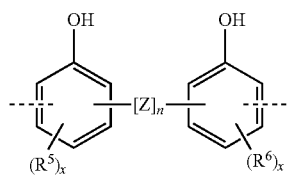

(2)

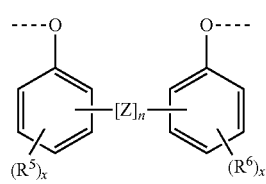

(3)

wherein Z represents a divalent organic group selected from any of

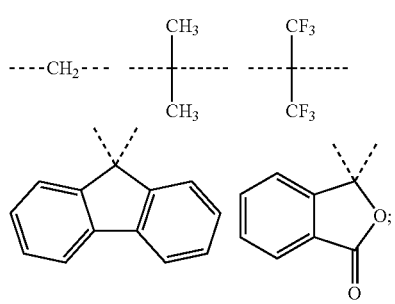

the dotted line represents a bond; "n" represents 0 or 1; $R^5$ and $R^6$ each represent an alkyl group or alkoxy group having 1 to 4 carbon atoms and are the same or different from each other; and "x" represents 0, 1, or 2;

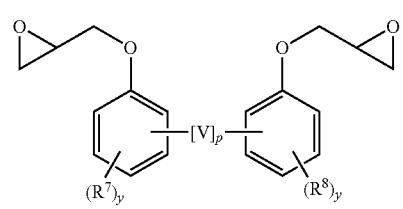

(4)

wherein V represents a divalent organic group selected from any of

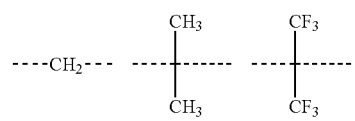

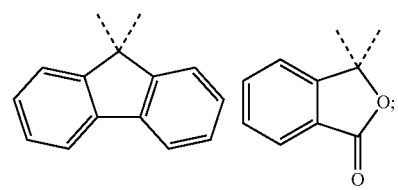

the dotted line represents a bond; "p" represents 0 or 1; $R^7$ and $R^8$ each represent an alkyl group or alkoxy group having 1 to 4 carbon atoms and are the same or different from each other; and "y" represents 0, 1, or 2;

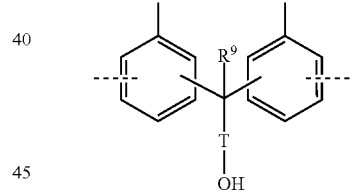

(5)

wherein the dotted line represents a bond; T represents an alkylene group having 1 to 10 carbon atoms or a divalent aromatic group; and $R^9$ represents a hydrogen atom or a methyl group;

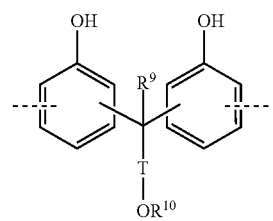

(6)

wherein the dotted line represents a bond; T and $R^9$ have the same meanings as defined above; and $R^{10}$ represents a monovalent carboxyl-containing organic group,

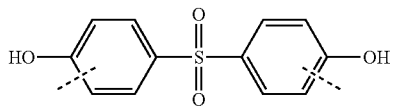

(7)

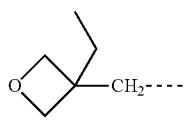

(C-1)

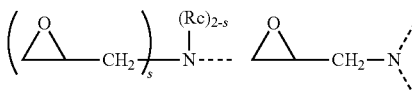

(C-2)

wherein the dotted line represents a bond; Rc represents a linear, branched, or cyclic alkyl group having 1 to 6 carbon atoms; and "s" represents 1 or 2.

2. The positive photosensitive resin composition according to claim 1, wherein $R^{10}$ in the general formula (6) is a monovalent carboxyl-containing organic group shown by the following general formula (8),

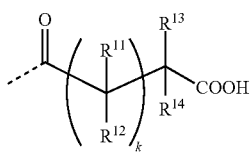

(8)

wherein the dotted line represents a bond; $R^{11}$ to $R^{14}$ are the same or different and represent a hydrogen atom, a halogen atom, a linear, branched, or cyclic alkyl group having 1 to 12 carbon atoms, or an aromatic group; $R^{11}$ and $R^{13}$ are optionally respectively bonded to $R^{12}$ and $R^{14}$ to form a substituted or unsubstituted ring structure having 1 to 12 carbon atoms; and "k" is any of 1 to 7.

3. The positive photosensitive resin composition according to claim 1, wherein in the general formula (1), $0 \leq a \leq 0.5$, $0 \leq b \leq 0.3$, $0 \leq c \leq 0.5$, $0 \leq d \leq 0.3$, $0 \leq e \leq 0.8$, $0 \leq f \leq 0.5$, $0 \leq g \leq 0.8$, $0 \leq h \leq 0.5$, $0 \leq i \leq 0.8$, and $0 \leq j \leq 0.5$.

4. The positive photosensitive resin composition according to claim 2, wherein in the general formula (1), $0 \leq a \leq 0.5$, $0 \leq b \leq 0.3$, $0 \leq c \leq 0.5$, $0 \leq d \leq 0.3$, $0 \leq e \leq 0.8$, $0 \leq f \leq 0.5$, $0 \leq g \leq 0.8$, $0 \leq h \leq 0.5$, $0 \leq i \leq 0.8$, and $0 \leq j \leq 0.5$.

5. The positive photosensitive resin composition according to claim 3, wherein in the general formula (1), $a=0$, $b=0$, $c=0$, $d=0$, $0 \leq e \leq 0.3$, $0 \leq f \leq 0.2$, $0 \leq g \leq 0.8$, $0 \leq h \leq 0.5$, $0 \leq i \leq 0.8$, and $0 \leq j \leq 0.5$.

6. The positive photosensitive resin composition according to claim 4, wherein in the general formula (1), $a=0$, $b=0$, $c=0$, $d=0$, $0 \leq e \leq 0.3$, $0 \leq f \leq 0.2$, $0 \leq g \leq 0.8$, $0 \leq h \leq 0.5$, $0 \leq i \leq 0.8$, and $0 \leq j \leq 0.5$.

7. The positive photosensitive resin composition according to claim 1, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

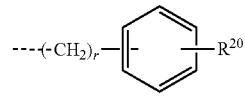

(27)

wherein "r" represents an integer of 0 to 10; and $R^{20}$ represents a hydroxyl group or a linear, branched, or cyclic alkoxy group having 1 to 12 carbon atoms.

8. The positive photosensitive resin composition according to claim 2, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

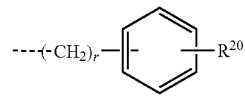

(27)

wherein "r" represents an integer of 0 to 10; and $R^{20}$ represents a hydroxyl group or a linear, branched, or cyclic alkoxy group having 1 to 12 carbon atoms.

9. The positive photosensitive resin composition according to claim 3, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

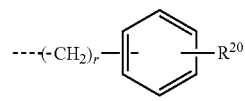

(27)

wherein "r" represents an integer of 0 to 10; and $R^{20}$ represents a hydroxyl group or a linear, branched, or cyclic alkoxy group having 1 to 12 carbon atoms.

10. The positive photosensitive resin composition according to claim 4, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

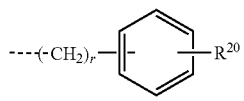

(27)

wherein "r" represents an integer of 0 to 10; and $R^{20}$ represents a hydroxyl group or a linear, branched, or cyclic alkoxy group having 1 to 12 carbon atoms.

11. The positive photosensitive resin composition according to claim 5, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

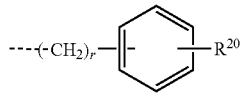

(27)

wherein "r" represents an integer of 0 to 10; and $R^{20}$ represents a hydroxyl group or a linear, branched, or cyclic alkoxy group having 1 to 12 carbon atoms.

12. The positive photosensitive resin composition according to claim 6, wherein in the general formula (1), "o" is an integer of 1 to 100; $R^1$ to $R^4$ are the same or different and represent a monovalent hydrocarbon group having 1 to 8 carbon atoms; $R^{18}$ represents a phenyl substituent containing a hydroxyl group or an alkoxy group and shown by the following general formula (27); and $R^{19}$ is the same as or different from $R^1$ to $R^4$ and represents a monovalent organic group having 1 to 10 carbon atoms and optionally containing an oxygen atom, or $R^{19}$ is the same as or different from $R^{18}$ and represents a phenyl substituent containing a hydroxyl group or an alkoxy group and shown by the general formula (27),

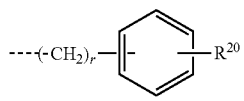

(27)

wherein "r" represents an integer of 0 to 10; and $R^{20}$ represents a hydroxyl group or a linear, branched, or cyclic alkoxy group having 1 to 12 carbon atoms.

13. The positive photosensitive resin composition according to claim 7, wherein the phenyl substituent shown by the general formula (27) is one group, or two or more groups selected from the following formulae (28),

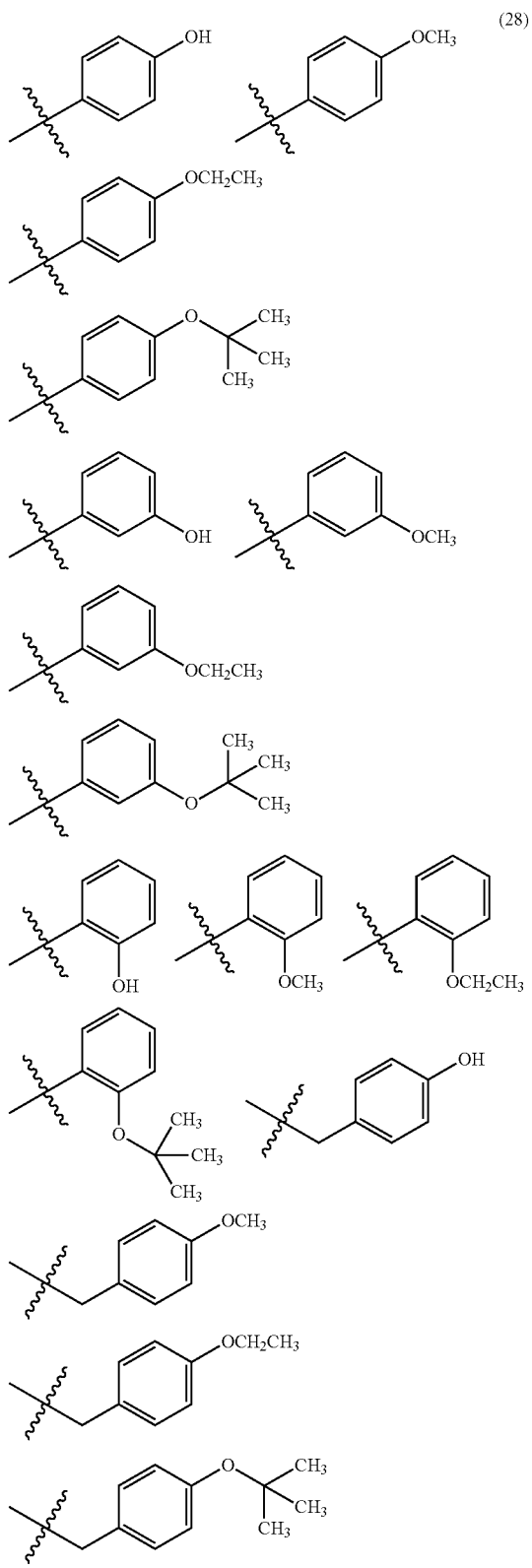

(28)

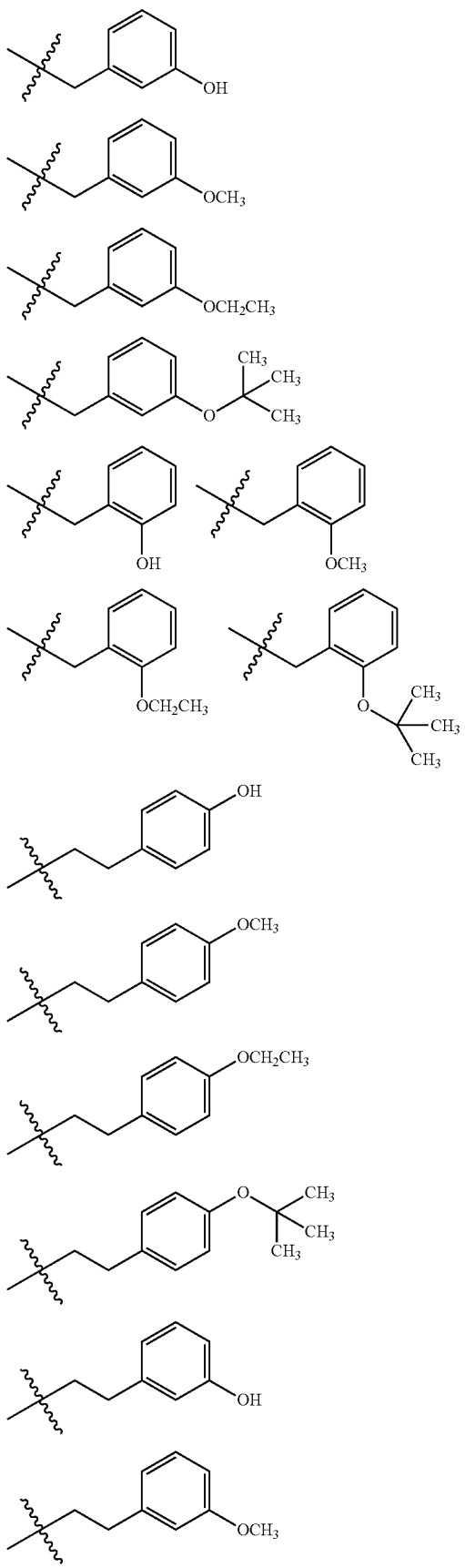
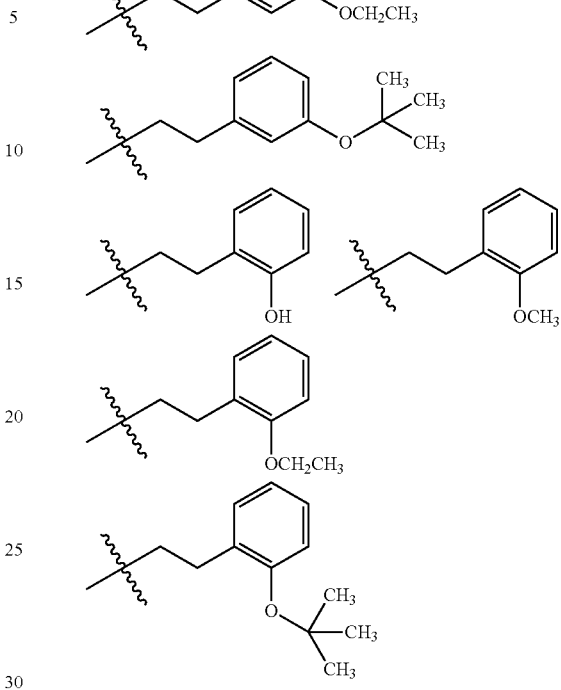

wherein the line with a wavy line represents a bonding arm.

14. A photo-curable dry film comprising a supporting film, a protective film, and a photo-curable resin layer having a thickness of 10 to 100 μm and sandwiched between the supporting film and the protective film, wherein the photo-curable resin layer is formed of the positive photosensitive resin composition according to claim 1.

15. A method for producing a photo-curable dry film, comprising:
(I) continuously applying the positive photosensitive resin composition according to claim 1 onto a supporting film to form a photo-curable resin layer,
(II) continuously drying the photo-curable resin layer, and further
(III) laminating a protective film on the photo-curable resin layer.

16. A patterning process comprising:
(1) applying the positive photosensitive resin composition according to claim 1 onto a substrate to form a photosensitive material film;
(2) exposing the photosensitive material film to a high energy beam having a wavelength of 190 to 500 nm or an electron beam via a photomask after a heat treatment; and
(3) performing development with a developer after a heat treatment.

17. A patterning process comprising:
(i) separating the protective film from the photo-curable dry film according to claim 14 and bringing the photo-curable resin layer thereby uncovered into close contact with a substrate;
(ii) exposing the photo-curable resin layer to a high energy beam having a wavelength of 190 to 500 nm or an electron beam via a photomask either through the supporting film or after removing the supporting film;

(iii) performing a heat treatment after the exposure; and
(iv) performing development with a developer.

18. The patterning process according to claim 16, further comprising post-curing a patterned film formed by the development at 100 to 250° C. after the development.

19. The patterning process according to claim 17, wherein the substrate includes a trench and/or a hole having an aperture width of 10 to 100 μm and a depth of 10 to 120 μm.

20. A laminate comprising a substrate including a trench and/or a hole having an aperture width of 10 to 100 μm and a depth of 10 to 120 μm, and the photo-curable resin layer of the photo-curable dry film according to claim 14 laminated on the substrate.

\* \* \* \* \*